US012576146B2

(12) United States Patent
Rockman et al.

(10) Patent No.: US 12,576,146 B2
(45) Date of Patent: Mar. 17, 2026

(54) METHOD FOR PRODUCING REASSORTANT INFLUENZA VIRUSES

(71) Applicant: Seqirus Pty Ltd., Victoria (AU)

(72) Inventors: Steven Rockman, Victoria (AU); Chi Ong, Victoria (AU); Erin Verity, Victoria (AU)

(73) Assignee: Seqirus UK Limited, Berkshire (GB)

( * ) Notice: Subject to any disclaimer, the term of this patent is extended or adjusted under 35 U.S.C. 154(b) by 772 days.

(21) Appl. No.: 17/775,475

(22) PCT Filed: Nov. 18, 2020

(86) PCT No.: PCT/EP2020/082587
§ 371 (c)(1),
(2) Date: May 9, 2022

(87) PCT Pub. No.: WO2021/099419
PCT Pub. Date: May 27, 2021

(65) Prior Publication Data
US 2023/0000971 A1     Jan. 5, 2023

(30) Foreign Application Priority Data
Nov. 18, 2019     (EP) ..................................... 19209839

(51) Int. Cl.
*A61K 39/145*          (2006.01)
*C12N 7/02*            (2006.01)
(52) U.S. Cl.
CPC ............ *A61K 39/145* (2013.01); *C12N 7/025* (2013.01); *C12N 2760/16121* (2013.01); *C12N 2760/16134* (2013.01); *C12N 2760/16152* (2013.01)

(58) Field of Classification Search
CPC .............. C07K 16/1003; C12N 5/0686; C12N 2760/16151; C12N 7/00; C12N 7/025; C12N 2760/16134; C12N 2760/16121; G01N 2333/165; G01N 2470/00; G01N 2470/04; G01N 33/543; G01N 33/56983; A61K 39/145; A61P 31/16
See application file for complete search history.

(56) References Cited

U.S. PATENT DOCUMENTS 4,338,296 A     7/1982  Löbmann et al.
8,715,940 B2    5/2014  Kawaoka et al.

FOREIGN PATENT DOCUMENTS

WO          WO 94/29439           12/1994
WO          WO 2008/153236 A1     12/2008
WO          WO 2011/145081 A1     11/2011
WO          WO 2014/115104        7/2014

OTHER PUBLICATIONS

Steel et al., "Live Attenuated Influenza Viruses Containing NS1 Truncations as Vaccine Candidates against H5N1 Highly Pathogenic Avian Influenza," Journal of Virology, 83(4):1742-1753 (2009).
International Search Report for International Application No. PCT/EP2020/082587, mailed Feb. 22, 2021.
Written Opinion of the International Searching Authority for International Application No. PCT/EP2020/082587.
International Preliminary Report on Patentability for International Application No. PCT/EP2020/082587, mailed Jun. 2, 2022, 10 pages.

*Primary Examiner* — Bao Q Li
(74) *Attorney, Agent, or Firm* — Finnegan, Henderson, Farabow, Garrett & Dunner, LLP

(57) ABSTRACT
A method for producing reassortant influenza viruses is provided. Also provided are reassortant influenza viruses produced according to the method, as well as vaccines based on said reassortant influenza viruses.

24 Claims, 3 Drawing Sheets
Specification includes a Sequence Listing.

NS1 Sequence Variation

PA Sequence Variation

METHOD FOR PRODUCING REASSORTANT INFLUENZA VIRUSES

TECHNICAL FIELD

The present invention is in the field of reassortant influenza viruses. It is concerned with methods of preparing reassortant influenza viruses, in particular reassortant viruses that can be used as seed viruses in the context of manufacturing influenza vaccines. Reassortant influenza viruses and vaccines produced by the methods of the invention are also aspects of the invention.

BACKGROUND ART

Reassortant influenza viruses have a genome that contains segments which are derived from two or more parent influenza strains. Such reassortant viruses are useful for manufacturing influenza vaccines because the properties of a high growth influenza strain can be harnessed to increase production of the hemagglutinin (HA) and/or neuraminidase (NA) antigens of a circulating strain, with the HA and/or NA antigens of the circulating strain being typical components of influenza vaccines. In vaccine manufacture, a reassortant virus (which may be referred to as a seed virus) typically contains the HA and NA segments of a circulating strain, and the backbone segments (i.e. PB1, PB2, PA, M, NS and NP) of a high growth influenza strain. This seed virus can be used to grow virus containing HA and NA more rapidly than simply propagating the circulating strain, which may have poor growth characteristics in the culture host platforms (e.g. eggs or cells) that are used in the influenza vaccine manufacturing process. For example, it has recently been shown that reassortant influenza A virus containing the HA and NA of the circulating strain and six backbone genes from the high growth parent A/Puerto Rico/8/34 (PR8) is a preferred seed virus for vaccine manufacture due to the high yield of circulating strain HA in the context of the PR8 backbone [1]. Two methods have been used to generate reassortant influenza viruses; classical reassortment and reverse genetics.

In classical reassortment, a culture host (typically an avian egg) is inoculated with both parent strains (i.e. the circulating strain and the high growth strain). Reassortant viruses that comprise the HA and/or NA of the circulating strain are then selected by growing the culture host in the presence of antibodies against the HA and/or NA of the high growth strain. Reassortant viruses containing the desired HA and NA surface genes can be isolated and used as seed viruses for vaccine manufacture.

However, one drawback associated with classical reassortment is that it does not allow for the controlled manipulation of gene sequences, which can be a problem when seeking to generate candidate seed viruses from highly pathogenic influenza viruses. For example, the HA of some H5 or H7 influenza strains contains a pathogenic determinant in the form of a polybasic cleavage site which cannot be deleted using the classical reassortment method. Classical reassortment can also produce of a mixture of reassortant viruses having 7:1, 6:2, 5:3 or 4:4 gene constellation ratios from each of the parent strains because the culture host is inoculated with two influenza strains, meaning that sixteen genes are present (i.e. eight from each parent strain). As a result, it can be time consuming to isolate the desired reassortant influenza virus for use as a seed virus in vaccine manufacture. For instance, it currently takes approximately 35 days from the arrival of a new influenza strain to obtain the final high-growth reassortant that is to be used as a seed virus in vaccine manufacture.

In reverse genetics, the genetic information required to produce the desired influenza virus is delivered to a cell, which is then able to generate influenza virus. Reverse genetics initially required the in vitro assembly and transfection of viral ribonucleoprotein (RNP) into cells infected with a helper virus [2,3]. Subsequent techniques involved the transfection of RNA polymerase I plasmids encoding all of the viral RNAs (vRNAs) together with protein expression constructs for the polymerase and NP genes [4]. More recently, reverse genetics methods involve the use of modified RNA polymerase I systems that allow the expression of both negative sense vRNA and positive mRNA from the same template [5]. In this method, each of the desired genes is cloned into the pHW2000 plasmid, which consists of the viral cDNA inserted between the RNA polymerase I promoter and termination sequences, and flanked by the CMV promoter and polyadenylation signal. After transfection of the eight plasmids into cells, synthesis of both vRNA and mRNA occurs, resulting in the production of virus. Further refinement has led to the development of systems in which linear DNA expression constructs are used instead of plasmids [6], and the use of a single expression construct [7].

In contrast to classical reassortment, reverse genetics allows manipulation of the gene sequences used to produce the virus. Thus, reverse genetics can be used to generate seed viruses for the production of live attenuated influenza vaccines because the viral gene sequences can be manipulated prior to transfection of the expression construct in the cell to produce a virus with an attenuated phenotype. Synthetic DNA sequences may also be used to produce seed viruses in reverse genetics, thereby negating the requirement to handle wild-type pandemic viruses [8]. Reverse genetics also allows for seed viruses to be produced in 4-7 days, which is substantially quicker than is provided by classical reassortment.

However, there are a number of drawbacks associated with reverse genetics. For instance, in reverse genetics the sequence of each influenza gene is pre-determined when the expression construct is prepared, meaning that the technique produces a more homogenous population of reassortant viruses compared to classical reassortment. This can be a problem if a circulating HA and NA are less compatible with the backbone genes that are used as standards in reverse genetics and so do not grow effectively. In this situation the HA and NA may grow more effectively with a different constellation of backbone genes, but it is time-consuming to identify and test for more appropriate backbone genes for use in reverse genetics. This can result in several passages of a reverse genetics derived reassortant influenza virus to enable the development of viruses having sequence variation in the backbone segments and selection of a seed virus with suitable growth characteristics. Another problem with some reverse genetics systems is that it can be difficult to introduce the required expression constructs into a culture host (due to low transfection efficiency, for example) which can make the reverse genetics system inefficient.

Methods of producing reassortant influenza viruses that combine elements of classical reassortment and reverse genetics have been discussed previously. For instance, a method in which a host cell is infected with a first influenza strain and transfected with one or more expression construct(s) encoding at least one segment from a second influenza strain are discussed in reference 11. This method is described only in the context of using an agent that inhibits translation and/or transcription of an influenza virus segment, such as siRNA, to produce a reassortant virus in which the segment targeted by the siRNA is absent.

It is therefore an object of the invention to provide improved methods of generating reassortant influenza viruses, which overcome the drawbacks associated with both classical reassortment and reverse genetics methods.

SUMMARY OF INVENTION

In a first aspect, the invention provides a method for generating reassortant influenza viruses comprising the steps of (i) contacting a culture host with a parent influenza virus strain comprising a first hemagglutinin (HA) gene and a first neuraminidase (NA) gene; (ii) introducing into the culture host one or more expression construct(s) comprising one or more influenza genes, wherein said influenza genes comprise a second HA gene or a second NA gene; (iii) culturing the culture host in order to produce reassortant viruses; (iv) selecting for reassortant viruses that comprise the second HA gene or the second NA gene; and optionally (v) isolating a reassortant influenza virus comprising the second HA gene or the second NA gene.

The invention also provides a population of reassortant influenza viruses produced by the methods of the invention.

The invention also provides an isolated reassortant influenza virus produced by the methods of the invention.

The methods of the invention are advantageous because the parent influenza virus strain that provides the first HA gene and the first NA gene, comprises a non-homogenous population of virions (i.e. sequence variants/quasi-species are present). This introduces sequence variability in backbone segments that are delivered to the culture host thereby enabling the methods of the invention to produce a wider diversity of reassortant viruses than reverse genetics techniques where clonal expression construct(s) (e.g. plasmids) are utilised. In contrast to reverse genetics systems, where the initially rescued virus may need to be passaged multiple times to introduce sequence variation and select for a virus with improved properties, the methods of the invention enable sequence variants to be present immediately in a reassorted virus produced by the methods of the invention (owing to the accumulated sequence variations that have accumulated naturally during propagation of a parent influenza strain). The greater diversity of reassortant viruses produced by the method also increases the likelihood of identifying a reassortant virus having one or more particularly desired properties (e.g. high HA yield and/or high growth).

Another advantage of the methods of the invention is that the methods inherently select against any sequences in the viral genome that have poor compatibility with the desired HA and/or NA that would otherwise result in a non-functional reassortant virus. These non-functional viruses will not propagate effectively in the culture host and be outcompeted by variants that have the desired high growth characteristics. This contrasts with reverse genetics techniques, in which sequence incompatibility would be identified only after the expression constructs had been produced and delivered to a culture host and there have been problems with the generation of a desired reassortant virus. In a related advantage, the methods of the invention also allow easier and more frequent identification of reassortant viruses containing combinations of mutations that synergize to provide improved growth properties. In fact, multiple mutations may not be identified at all using reverse genetics. For instance, in situations where a single mutation had a negative effect, this variant may be discarded, and thus not tested in the context of further sequence variants, which could rescue the negative effect and elicit further advantages in combination.

The invention is distinguished from classical reassortment because the second HA gene or the second NA gene is introduced into a culture host as part of an expression construct, instead of infection with a second influenza virus strain. Provision of the second HA gene or the second NA gene using an expression construct means that the HA gene or NA gene can be manipulated before it is provided to the culture host in a way that is not possible in classical reassortment. This ability to manipulate the HA sequence is particularly advantageous in the context of pandemic or potentially pandemic strains (such as H5 and H7 strains) because it allows deletion of pathogenic determinants, such as the polybasic cleavage site. Another advantage of delivering an HA gene or NA gene on an expression construct is that this allows for expression of a single HA or NA clone with a pre-determined sequence. This contrasts with methods in which the HA and NA genes are delivered in the context of a replicating virus (such as classical reassortment), where there is a risk that mutations are introduced into an HA or NA gene during replication, that may result in, for example, reduced antigenicity.

The method therefore allows the HA segment or NA segment that is to be present in the reassortant influenza virus to be controlled, as it may be in reverse genetics, but at the same time provides a pool of backbone segments with some intrinsic variability by introducing a population of backbone genes to the culture host through infection with a parent influenza virus strain. This is advantageous because the method allows an optimised seed virus for use in vaccine manufacture to be generated more quickly, particularly in situations where backbone genes that are typically used in reverse genetics (e.g. PR8) provide suboptimal properties when reassorted with the HA and/or NA of a circulating strain. In such situations, the virus that is initially rescued in a reverse genetics experiment requires multiple passages in a culture host in order to improve the growth of the virus. The same multiple passages are not necessarily required in the methods of the invention because a reassortant virus with strong growth properties can be selected from the diverse pool of reassortant viruses that are produced by the method. In other words, diversity of backbone genes in the parent strain, generated in the context of a replicating virus, combined with low-level selection against, and elimination of, non-viable or poorly growing reassortant viruses, allows for more efficient generation of high growth reassortant viruses.

A reassortant influenza virus produced by the methods of the invention may be particularly useful for the manufacture of an influenza vaccine. Accordingly, in a further aspect the invention provides a method of preparing a vaccine, comprising the steps of (a) preparing a reassortant influenza virus by the method of the invention, and (b) preparing a vaccine from the reassortant influenza virus. Also provided is a vaccine produced by the methods of the invention.

DETAILED DESCRIPTION

Reassortant Influenza Viruses

Figure 1:
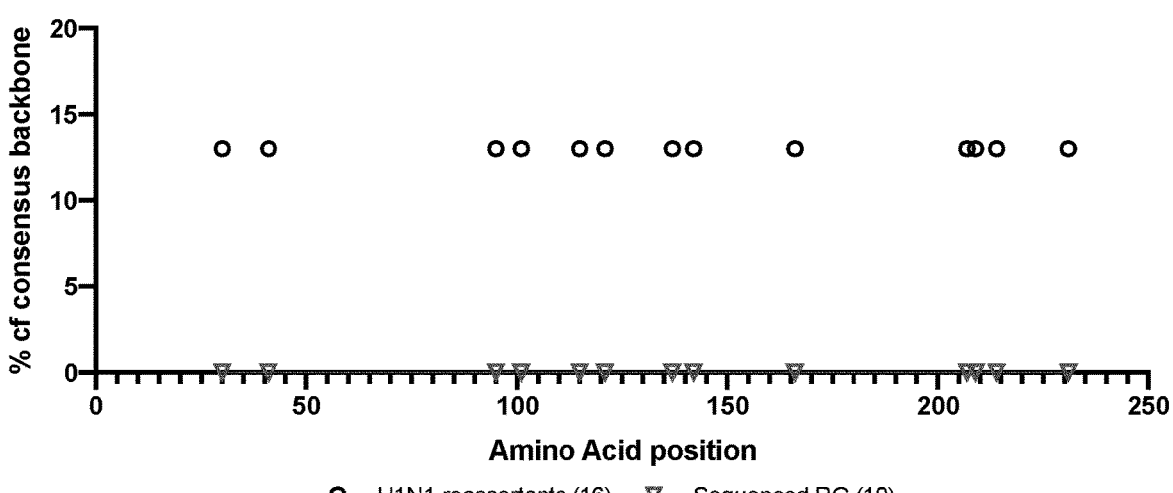
FIG. 1 is a graphical representation of the sequence variation present in M1 proteins of H1N1 viruses produced by classical reassortment and viruses produced by reverse genetics, as described in Table 1. A value of 0% cf consensus backbone indicates that there are no sequence variants present at that position relative to the consensus backbone sequence. There are no sequence variants in the M1 protein of the viruses produced by reverse genetics.

Influenza viruses are segmented negative strand RNA viruses. The influenza A and B virus genomes contain eight single-stranded viral RNA (vRNA) segments. The eight genomic segments of influenza A and B viruses are, in order of size, PB2, PB1, PA, HA, NP, NA, M, NS. The PB2, PB1, PA, NP, M and NS encode the internal and non-structural proteins, and may be referred to as the backbone segments. The HA and NA segments encode the surface glycoproteins. The methods of the invention may be used to produce reassortant influenza A viruses. Alternatively, the methods of the invention may be used to produce reassortant influenza B viruses.

For influenza A viruses the eight genome segments encode eleven proteins, as follows: haemagglutinin (HA), neuraminidase (NA), two matrix proteins (M1 and M2), a heterotrimeric RNA-dependent RNA polymerase (made up of one polymerase acidic subunit (PA), and two polymerase basic subunits (PB1 and PB2)), nucleoprotein (NP), and two non-structural proteins (NS1 and NS2; NS2 is also known as nuclear export protein (NEP)). Some influenza A viruses also express a pro-apoptotic peptide, PB1-F2. The PB2, PA, HA, NP and NA segments each encode a single expressed protein. The PB1, M and NS segments encode more than one protein. The PB1 segment encodes the PB1 protein, as well as the PB1-F2 protein (which is encoded in a +1 reading frame on the PB1 segment). The M segment encodes the M1 and M2 proteins. The NS segment encodes the NS1 and NS2/NEP proteins. The M2 and NS2/NEP protein are expressed from spliced mRNAs from the M and NS segments.

For influenza B viruses, the eight genome segments also encode eleven proteins, although there are a few differences from influenza A viruses. As for influenza A viruses, the PB2, PA, HA and NP segments each encode a single expressed protein, and the NS segment encodes the NS1 and NS2/NEP protein. The PB1-F2 protein is not present in influenza B viruses, meaning that the PB1 segment encodes the PB1 protein alone. In addition to the NA protein, the NA segment in influenza B viruses also encodes the NB matrix protein in an alternate −1 reading frame. The NB matrix protein corresponds to the M2 protein in influenza A. The M segment encodes the M1 protein, and in an alternate +2 reading frame, the BM2 protein.

A reassortant influenza virus comprises genome segments that are derived from two or more parent influenza virus strains. Reassortant influenza viruses produced by the methods of the invention comprise one or more gene segments from a first parent influenza virus strain (the donor strain), and one or more gene segments from a second parent influenza virus strain (the vaccine strain). Influenza donor strains are strains which typically provide the backbone segment in a reassortant influenza virus, even though they may sometimes also provide the NA segment of the virus. The vaccine strain is the influenza strain that provides the HA or NA segment. Typically, both the HA and the NA segment in a reassortant influenza virus will be from the vaccine strain. In the methods of the invention, the second HA gene or the second NA gene which is introduced into a culture host as part of an expression construct is derived from the vaccine strain. The vaccine strain is typically a circulating strain. The vaccine strain is different from the donor strain.

The genome segments that are present in a reassortant virus can be described using a gene constellation ratio, which indicates the number of segments that are provided by each parent influenza virus strain. For instance, when a reassortant virus contains genome segments from two parent influenza virus strains (such as a donor strain and a vaccine strain), it may have a gene constellation ratio of 1:7, 2:6, 3:5, 4:4, 5:3, 6:2, or 7:1. A reassortant virus may comprise genome segments from three parent influenza virus strains, where present. In these embodiments, the reassortant virus may have a gene constellation ratio of 1:1:6, 1:2:5, 1:3:4, 1:4:3, 1:5:2, 1:6:1, 2:1:5, 2:2:4, 2:3:3, 2:4:2, 2:5:1, 3:1:2, 3:2:1, 4:1:3, 4:2:2, 4:3:1, 5:1:2, 5:2:1, or 6:1:1.

The majority of genome segments of the reassortant viruses produced by the invention are typically from the donor strain because it is desirable to harness the properties of the donor strain through reassortment of the donor strains segments with segments from the vaccine strain. In certain such embodiments, the reassortant influenza virus produced by the methods of the invention has a gene constellation ratio of 5:3, 6:2, or 7:1, wherein the first number of the ratio indicates the number of segments from the donor strain and the second number of the ratio indicates the number of segments from the vaccine strain.

In preferred embodiments, the reassortant influenza virus has a gene constellation ratio of 6:2. In these embodiments the reassortant influenza virus comprises six backbone segments (i.e. PB1, PB2, PA, NP, M, and NS) from the donor strain and two segments (i.e. HA and NA) from the vaccine strain. In particularly preferred embodiments the reassortant influenza virus is a reassortant influenza A virus having a gene constellation ratio of 6:2.

In other embodiments, the reassortant influenza virus has a gene constellation ratio of 7:1. In some of these embodiments, the reassortant influenza virus comprises the six backbone segments from the donor strain, the HA segment from the vaccine strain, and the NA segment from the donor strain. In other words, the reassortant influenza virus comprises the HA segment from the vaccine strain and the remaining seven segments from the donor strain. In other embodiments, the reassortant influenza virus comprises the six backbone segments and the HA segment from the donor strain, and the NA segment from the vaccine strain. In other words, the reassortant influenza virus comprises the NA segment from the vaccine strain and the remaining seven segments from the donor strain. A 7:1 gene constellation ratio is preferred for reassortant influenza B viruses.

In other embodiments, the reassortant influenza virus has a gene constellation ratio of 5:3. In these embodiments, the reassortant virus comprises five backbone segments (i.e. five segments selected from the group consisting of: PB1, PB2, PA, NP, M, and NS) and three segments from the vaccine strain. In these embodiments the three segments from the vaccine strain are HA, NA and one backbone segment (i.e. one segment selected from the group consisting of: PB1, PB2, PA, NP, M and NS). In a preferred embodiment, the three segments from the vaccine strain are HA, NA and PB1 and the remaining five backbone segments (i.e. PB2, PA, NP, M and NS) are from the donor strain.

Influenza Virus Strains

In the methods of the invention, the parent influenza virus strain that the culture host is contacted with is the donor strain. The donor strain is replication-competent (i.e. it can propagate itself in the culture host following infection). Contacting the culture host with the donor strain causes the genome segments of the donor strain to be delivered to the culture host when the virus infects the culture host.

Any influenza virus strain that possesses a set of desired characteristics may be used as a donor strain. In certain embodiments, the donor strain is a strain which has good growth characteristics in cells and/or eggs. Typically, good growth characteristics are measured according to the yield of HA when the virus is propagated in a culture host. A donor strain that has good growth characteristics may be referred to as a high growth parent strain (HGP strain). Thus, in certain embodiments, the parent influenza virus strain that the culture host is contacted with is a high growth parent strain. Examples of high growth parent strains that may be used in the methods of the invention are A/Puerto Rico/8/1934 (PR8), A/Texas/1/1977, A/New York/55/2004, A/Ann Arbor/6/60, A/Leningrad/134/17/57, B/Ann Arbor/1/66, B/Florida/4/2006, B/Panama/45/1990 and B/Lee/1940. In a preferred embodiment, A/Puerto Rico/8/1934 is the donor strain for influenza A viruses. A strain which grows to similar or higher viral titres compared to a high growth parent strain may be used as the donor strain.

An influenza strain that may be used as the donor strain in the methods of the invention typically provides the culture host with a population of backbone segments that is not homogenous. This is because the donor strain comprises a population of virions that are not homogenous (i.e. sequence variants are present). These variant backbone segments may arise from spontaneous mutation in the influenza virus genome. The mutation rate may be expressed as substitutions per nucleotide per cell infection (s/n/c) and may range from $10^{-5}$ to $10^{-7}$ for influenza viruses. This means approximately 1 in 1000 influenza virions in a population of virions comprise a mutation in a genome segment. Thus, the donor strain that may be used in the methods of the invention comprises a population of closely-related quasi-species influenza viruses. The term "quasi-species" is used to denote influenza viruses that are derived from a single source but contain sequence variants. This differs from sequence variations between influenza viruses derived from different sources (which are considered separate species). The methods of the invention therefore involve contacting a culture host with a donor strain comprising a population of quasi-species of influenza viruses (i.e. influenza viruses having sequence variations that are derived from a single source). In this way, a population of variant backbone segments is delivered to the culture host.

The variation within a population of backbone segments (e.g. NP segments) may be expressed as a percentage according to the number of sequence positions that differ between the two most divergent sequences within the population of backbone segments when the sequences of backbone segments are aligned. A sequence difference may be a substitution, deletion or insertion. To identify the two most divergent sequences within a population, a multiple sequence alignment may be performed. Suitable tools for aligning multiple protein sequences are available (for example, the Clustal Omega tool using its default parameters, as mentioned in Maderia et al. *Nucleic Acids Research* 2019 (47) doi: 10.1093/nar/gkz268). For instance, as discussed in Example 5, the NP protein has a sequence of 498 amino acids and 44 mutations were identified in the NP protein amino acid sequences of H1N1 viruses produced by classical reassortment. This corresponds to about 9% variation across the NP protein when comparing the two most divergent NP protein sequences within the H1N1 reassortant group. A percentage sequence variation across the backbone protein may be calculated using the formula:

$$\frac{\text{Number of variant positions}}{\text{Total number of amino acids in protein}} \times 100$$

In some embodiments, the donor strain comprises a population of quasi-species of influenza viruses comprising at least 3%, at least 4%, at least 5%, at least 6%, at least 7%, at least 8%, at least 9%, at least 10%, at least 15% or at least 20% amino acid sequence variation in one or more of the backbone segments. The donor strain population of quasi-species may comprise no more than 30% amino acid sequence variation in any backbone segment.

In some embodiments, the donor strain comprises a population of quasi-species of influenza viruses comprising at least 5% amino acid sequence variation in the M1 protein.

In some embodiments, the donor strain comprises a population of quasi-species of influenza viruses comprising at least 5% amino acid sequence variation in the NP protein. In some embodiments, the donor strain comprises a population of quasi-species of influenza viruses comprising at least 8% amino acid sequence variation in the NP protein.

In some embodiments, the donor strain comprises a population of quasi-species of influenza viruses comprising at least 5% amino acid sequence variation in the NS1 protein. In some embodiments, the donor strain comprises a population of quasi-species of influenza viruses comprising at least 15% amino acid sequence variation in the NS1 protein.

In some embodiments, the donor strain comprises a population of quasi-species of influenza viruses comprising at least 5% amino acid sequence variation in the PA protein.

In some embodiments, the donor strain comprises a population of quasi-species of influenza viruses comprising at least 5% amino acid sequence variation in the PB2 protein.

In some embodiments, the donor strain comprises a population of quasi-species of influenza viruses comprising at least 5% amino acid sequence variation in the M1 protein, at least 5% amino acid sequence variation in the NP protein, at least 5% amino acid sequence variation in the NS1 protein, at least 5% amino acid sequence variation in the PA protein and least 5% amino acid sequence variation in the PB2 protein.

In some embodiments, the donor strain comprises a population of quasi-species of influenza viruses comprising at least 5% amino acid sequence variation in the M1 protein, at least 8% amino acid sequence variation in the NP protein, at least 15% amino acid sequence variation in the NS1 protein, at least 5% amino acid sequence variation in the PA protein and least 5% amino acid sequence variation in the PB2 protein.

Other donor strains may be produced for use in the methods of the invention. To produce a donor strain for use in the methods of the invention, an influenza virus strain may be propagated in the culture host that is used in the methods of the invention. Passaging an influenza virus strain in the culture host that is used in the methods of the invention leads to the generation of variant influenza strains which contain sequence variations that allow the variant strain to grow to higher viral titres (in the same time and under the same growth conditions) compared to the influenza virus strain from which they are derived. The variant influenza strain therefore has improved growth characteristics in the culture host that is used in the method of the invention and is a preferred donor strain. For example, passaging the A/Puerto Rico/8/1934 influenza strain several times in cell culture produced a variant influenza strain (the PR8-X strain) which grows to higher viral titres in those cells compared to the original A/Puerto Rico/8/1934 strain. Thus, in certain embodiments, the PR8-X strain is the donor strain. Similarly, passaging the A/New Caledonia/20/1999 strain several times in cell culture produced a variant strain (the 105p30 strain) which grows to higher viral titres compared to the wild-type A/New Caledonia/20/1999 strain in the same time and under the same growth conditions.

The gene segments of PR8-X have the nucleotide sequences of SEQ ID NO: 1 (PA), SEQ ID NO: 2 (PB1), SEQ ID NO: 3 (PB2), SEQ ID NO: 4 (NP), SEQ ID NO: 5 (M), SEQ ID NO: 6 (NS), SEQ ID NO: 7 (HA) or SEQ ID NO: 8 (NA). In some embodiments, an influenza strain comprising gene segments that encode the same amino acid sequence as the gene segments of PR8-X may be used as the donor strain.

The gene segments of 105p30 have the nucleotide sequences of SEQ ID NO: 9 (PA), SEQ ID NO: 10 (PB1), SEQ ID NO: 11 (PB2), SEQ ID NO: 12 (NP), SEQ ID NO: 13 (M), SEQ ID NO: 14 (NS), SEQ ID NO: 15 (HA) or SEQ ID NO: 16 (NA). In some embodiments, an influenza strain comprising gene segments that encode the same amino acid sequence as the gene segments of 105p30 may be used as a donor strain.

Donor strains suitable for use in the methods of the present invention will typically achieve improved viral titres and/or growth kinetics when compared to the viral titres obtained with the influenza strain from which the donor strain was derived. In certain embodiments, the improved viral titre of the donor strain is at least 10%, at least 20%, at least 50%, at least 100%, at least 200%, at least 500%, or at least 1000% higher when grown under the same growth conditions and for the same time (for example 12 hours, 24 hours, 48 hours or 72 hours) as the influenza strain from which the donor strain was derived.

In certain embodiments, the donor strain is a strain that has regulatory approval for use in vaccine manufacture. It is advantageous to use a donor strain that has regulatory approval because reassortant viruses generated by the method of the invention may be used to prepare vaccines, which may be able to be marketed more easily than if the donor strain does not have pre-existing regulatory approval.

The inventors have found that production of reassortant influenza is enhanced when the culture host is contacted with a purified donor strain. Purification of the donor strain may be advantageous when the donor strain is delivered to the culture host concurrently with transfection of the second HA gene and/or second NA gene. This is because contaminating egg proteins or cell culture proteins (which may be present following propagation of the donor strain) may interfere with transfection of an expression construct to the culture host. Accordingly, in some embodiments, the culture host is contacted with a purified donor strain. In certain such embodiments, the culture host is contacted with a purified donor strain and the one or more expression construct(s) comprising the second HA gene or the second NA gene are introduced into the culture host by transfection.

A donor strain may have been propagated in cell culture and/or eggs prior to use in the method. In some embodiments, the method comprises a step of passaging an influenza virus strain in cell culture or eggs to produce the donor strain (e.g. the donor strain population) for infecting the culture host. A pre-passaging step (or more than one pre-passaging step) may be advantageous as this may increase the number sequence variants that are present in the population of virions that are delivered to the culture host.

The donor strain may be concentrated and purified from cell culture medium or allantoic fluid using standard methods. In some embodiments, the methods comprise a step of purifying the donor strain before the culture host is contacted with the donor strain. For example, a purification process may involve centrifugation using a sucrose gradient solution or affinity chromatography methods. In one embodiment, the donor strain is purified by filtration and/or centrifugation. In one embodiment, a step of purifying the donor strain comprises a filtration step followed by a centrifugation step. For example, culture medium or allantoic fluid comprising the donor strain may be filtered through a 0.45 μm filter, and subsequently purified by centrifugation, for example at approximately 1400×g for 1 hr using a centrifugal filter device. After purification, the donor strain may be suspended in buffer, for example PBS, which allows the purified donor strain to be stored and transported, prior to use in the methods of the invention.

Helper viruses were used in early reverse genetics techniques to facilitate the expression of the influenza gene segments from the expression constructs (e.g. by providing components such as an RNA-dependent RNA polymerase (RdRp) or other proteins involved in replication of the viral genome). Typically, these early reverse genetics systems used expression constructs in the form of ribonucleoprotein complexes comprising a viral segment-encoding RNA, purified RNA-dependent RNA polymerase proteins and viral nucleoprotein components. These protein components delivered the machinery required to replicate the viral segments encoded by the RNA to the culture host. The protein components of the ribonucleoprotein complexes (RdRp and NP) needed to be purified from influenza viruses prior to in vitro assembly with a viral segment-encoding RNA. In addition to transfecting a culture host with the RNP component, a helper virus was required for efficient production of viruses. However, the components of the helper virus were generally not intended for incorporation into the reassortant viruses that were produced in these reverse genetics techniques. Subsequent developments in the expression constructs used in reverse genetics systems has meant that neither the RNP nor helper virus components are necessary because the later expression constructs can provide all of the components required to produce viral particles.

The parent influenza virus strain that is contacted with a culture host in the methods of the invention is not a helper virus because the components of parent influenza virus strain that are involved in the replication of the viral genome are intended for incorporation into the reassortant influenza viruses produced by the methods of the invention. Accordingly, in some embodiments, the methods of the invention are helper virus-free.

Expression Constructs

In the methods of the invention, one or more expression construct(s) comprising one or more influenza genes are introduced into the culture host. The one or more expression construct(s) may be introduced into a cell culture using any method for introducing expression construct(s) from known reverse genetics techniques.

The methods of the present invention do not require the use of exogenously added RNPs, and so do not require additional viral RNA-directed RNA polymerase proteins and viral nucleoprotein to be provided with the one or more expression construct(s). Accordingly, in the context of the invention a ribonucleoprotein complex (e.g. a viral segment-encoding RNA complexed with purified RNA-dependent RNA polymerase proteins and viral nucleoproteins) is not an expression construct. An expression construct according to the invention is free of RNPs. The step of introducing one or more expression construct(s) into a culture host comprises the delivery of one or more expression construct(s) into the culture host without contacting or transfecting the culture host with a ribonucleoprotein complex (e.g. without simultaneously, or separately contacting or transfecting the culture host with a RNP complex).

In the context of the invention, an influenza virion is not an expression construct. This means that contacting a culture host with an influenza strain does not amount to introducing one or more expression construct(s) into the culture host. In other words, the step of introducing one or more expression construct(s) into a culture host comprises the delivery of one or more expression construct(s) into the culture host via means that is not contacting or infecting the culture host with an influenza virion. This differs from classical reassortment, in which all of the influenza genes are delivered to the culture host through infection by parent influenza virus strains.

Expression constructs for use in the invention are typically recombinant or synthetic nucleic acid constructs, which may have been assembled in vitro (e.g. using recombinant techniques known to those skilled in the art). Use of one or more expression construct(s) means that the sequence of the influenza genes can be precisely manipulated, in a way that is not possible were the requisite influenza genes to be provided by infection with an influenza virus (as is the case with classical reassortment methodologies).

Expression constructs suitable for use in the methods of the invention may be uni-directional or bi-directional expression constructs. As influenza viruses require a protein for infectivity, it is generally preferred to use bi-directional expression constructs as this reduces the total number of expression constructs required by the host cell. Thus, the methods of the invention may utilise at least one bi-directional expression construct wherein at least one gene or cDNA is located between an upstream pol II promoter and a downstream non-endogenous pol I promoter. Transcription of the gene or cDNA from the pol II promoter produces capped positive-sense viral mRNA which can be translated into a protein, while transcription from the non-endogenous pol I promoter produces negative-sense vRNA. The bi-directional expression construct may be a bi-directional expression vector.

Bi-directional expression constructs contain at least two promoters which drive expression in different directions (i.e. both 5' to 3' and 3' to 5') from the same construct. The two promoters can be operably linked to different strands of the same double stranded DNA. Preferably, one of the promoters is a pol I promoter and at least one of the other promoters is a pol II promoter. This is useful as the pol I promoter can be used to express uncapped vRNAs while the pol II promoter can be used to transcribe mRNAs which can subsequently be translated into proteins, thus allowing simultaneous expression of RNA and protein from the same construct. Where more than one expression construct is used within an expression system, the promoters may be a mixture of endogenous and non-endogenous promoters.

The pol I and pol II promoters used in the expression constructs may be endogenous to an organism from the same taxonomic order from which the host cell is derived. Alternatively, the promoters can be derived from an organism in a different taxonomic order than the host cell. The term "order" refers to conventional taxonomic ranking, and examples of orders are primates, rodentia, carnivora, marsupialia, cetacean, etc. Humans and chimpanzees are in the same taxonomic order (primates), but humans and dogs are in different orders (primates vs. carnivora). For example, the human pol I promoter can be used to express viral segments in canine cells (e.g. MDCK cells) [9].

The expression construct will typically include an RNA transcription termination sequence. The termination sequence may be an endogenous termination sequence or a termination sequence which is not endogenous to the host cell. Suitable termination sequences will be evident to those of skill in the art and include, but are not limited to, RNA polymerase I transcription termination sequence, RNA polymerase II transcription termination sequence, and ribozymes. Furthermore, the expression constructs may contain one or more polyadenylation signals for mRNAs, particularly at the end of a gene whose expression is controlled by a pol II promoter.

An expression construct may be a vector, such as a plasmid or other episomal construct. Such vectors will typically comprise at least one bacterial and/or eukaryotic origin of replication. Furthermore, the vector may comprise a selectable marker which allows for selection in prokaryotic and/or eukaryotic cells. Examples of such selectable markers are genes conferring resistance to antibiotics, such as ampicillin or kanamycin. The vector may further comprise one or more multiple cloning sites to facilitate cloning of a DNA sequence.

An expression construct may be a linear expression construct. Such linear expression constructs will typically not contain any amplification and/or selection sequences.

However, linear constructs comprising such amplification and/or selection sequences are also within the scope of the present invention. Reference 6 describes a linear expression construct which describes individual linear expression constructs for each viral segment. It is also possible to include more than one, for example two, three four, five or six viral segments on the same linear expression construct. Such a system has been described, for example, in reference 6.

Expression constructs can be generated using methods known in the art. Such methods were described, for example, in reference 10. Where the expression construct is a linear expression construct, it is possible to linearise it before introduction into the host cell utilising a single restriction enzyme site. Alternatively, it is possible to excise the expression construct from a vector using at least two restriction enzyme sites. Furthermore, it is also possible to obtain a linear expression construct by amplifying it using a nucleic acid amplification technique (e.g. by PCR).

The expression constructs used in the methods of the invention may be non-bacterial expression constructs. This means that the construct can drive expression in a eukaryotic cell of viral RNA segments encoded therein, but it does not include components which would be required for propagation of the construct in bacteria. Thus the construct will not include a bacterial origin of replication (ori), and usually will not include a bacterial selection marker (e.g. an antibiotic resistance marker). Such expression constructs are described in reference 7.

The expression constructs may be prepared by chemical synthesis. The expression constructs may either be prepared entirely or in part by chemical synthesis. Suitable methods for preparing expression constructs by chemical synthesis are described, for example, in reference 7. Thus, in certain embodiments the expression construct may comprise a synthetic nucleic acid sequence. In some embodiments the expression construct may comprise a synthetic DNA sequence. In some embodiments, the expression construct may comprise a synthetic RNA sequence.

The expression constructs used in the methods of the invention can be introduced into host cells using any technique known to those of skill in the art. For example, expression constructs of the invention can be introduced into host cells by employing electroporation, DEAE-dextran, calcium phosphate precipitation, liposomes, microinjection, or microparticle-bombardment.

In some embodiments, an expression construct may be in the form of naked nucleic acid. The naked nucleic acid may have been purified from an influenza virus. In another embodiment, an expression construct may be in the form of transcribed RNA. In other embodiments, expression construct may be in the form of one or more shuttle vectors. Examples of shuttle vectors include non-influenza viruses and replicons, for instance alphavirus based replicons.

The nucleotide sequence of the expression construct may be manipulated, which allows the sequence of the influenza segments present in the reassortant viruses produced in the methods of the invention to be controlled. Accordingly, influenza HA encoded by an expression construct may have a natural HA as found in a wild-type virus, or a modified HA. For instance, it is known to modify HA to remove determinants (e.g. hyper-basic regions around the HA1/HA2 cleavage site) that cause a virus to be highly pathogenic. In some embodiments, the HA is modified to remove the polybasic cleavage site. In certain such embodiments, the HA is from an H5 or H7 influenza strain and does not comprise a polybasic cleavage site. Similarly, influenza NA encoded by an expression construct may have an NA as found in a wild-type virus, or a modified NA. For instance, an NA may be modified to confer susceptibility to antiviral neuraminidase inhibitors if the vaccine strain NA comprises pre-existing neuraminidase inhibitor resistance mutations. Introducing an influenza gene (for example, an HA or NA gene) into the culture host on an expression construct allows the sequence to modified prior to introduction into the culture host.

HA and/or NA sequences may also be manipulated to produce chimeric HA or chimeric NA sequences containing sequences from more than one influenza strain. For instance, a chimeric HA or chimeric NA may contain the cytoplasmic, or cytoplasmic and transmembrane portions of the HA or NA from one strain and at least the extracellular antigenic portion of the HA or NA from a different strain. This approach has been described previously as a technique for producing influenza viruses containing the antigenic portion of the HA or NA in circumstances where the unmodified HA and/or NA segment may be produced at low yields. However, the methods of the present invention may avoid the need for the use of chimeric HA and/or chimeric NA segment because the sequence variants that are present in the population of virions that are delivered to the culture host by infection with an influenza virus strain may provide sufficient variation for the efficient production of reassortant viruses comprising an non-chimeric HA and and/or an non-chimeric NA.

Accordingly, in some embodiments, the HA sequence is a non-chimeric HA sequence. In other words, the HA sequence comprises the cytoplasmic, transmembrane and extracellular domain from the same influenza strain. In some embodiments, the NA sequence is a non-chimeric NA sequence. In other words, the NA sequence comprises the cytoplasmic, transmembrane and extracellular domain from the same influenza strain. In certain such embodiments, although the HA sequence and/or NA sequence is a non-chimeric sequence, it may comprise other modifications as described herein. For instance, a non-chimeric HA sequence may be modified to remove determinants (e.g. hyper-basic regions around the HA1/HA2 cleavage site) that cause a virus to be highly pathogenic. Similarly, a non-chimeric NA sequence may be modified to confer susceptibility to anti-viral neuraminidase inhibitors if the vaccine strain NA comprises pre-existing neuraminidase inhibitor resistance mutations.

The number of influenza genes that are delivered to the culture host may be controlled in the methods of the invention. In certain embodiments, the one or more expression construct(s) comprise no more than seven influenza genes. Providing no more than seven influenza genes is advantageous because it means that fewer influenza genes are provided to the culture host than in classical reassortment (where eight segments are provided by a second influenza virus strain), and so reduces the number of gene constellation ratios that may be present in the reassortant viruses generated by the methods. By further limiting the number of influenza genes, the gene constellation ratios that may be present in the reassortant viruses generated by the method are also limited. Thus, in certain embodiments the one or more expression construct(s) comprise no more than six influenza genes. In other embodiments, the one or more expression construct(s) comprise no more than five influenza gene. In further embodiments, the one or more expression construct(s) comprise no more than four influenza genes.

The provision of fewer influenza genes can be particularly advantageous when seeking to maximise the production of a reassortant virus having a particular gene constellation ratio. For example, when the one or more expression construct(s) comprise no more than a single HA gene and a single NA gene the likelihood of producing 7:1 and 6:2 viruses is increased. This is because the only backbone segments that are present in the culture host for the production of reassortant viruses are from the donor strain. Thus, in a preferred embodiment, the one or more expression construct(s) comprise no more than two influenza genes. In certain such embodiments, the one or more expression construct(s) comprise one HA gene and one NA gene.

In some embodiments, the one or more expression construct(s) comprise no more than three influenza gene. In these embodiments, the one or more expression construct(s) comprise one HA gene, one NA gene and one backbone gene. The backbone gene is selected from the group consisting of: PB2, PB1, PA, NP, M, and NS. Preferably, the backbone gene is PB1. Introducing a single backbone segment with the HA and NA gene to the culture host allows for the production of 5:3 reassortant viruses. In these embodiments, negative selection against the corresponding backbone segment from the donor strain can be preferably performed using an agent that inhibits the transcription and/or translation of the backbone segment. In certain embodiments, an RNAi agent is used. Use of an agent that inhibits transcription and/or translation is advantageous because the backbone segment is less exposed on the surface of an influenza virion than HA and NA, and thus less amenable to selection using one or more antibodies for or against a backbone segment.

In some embodiments, the one or more expression construct(s) comprises no more than a single influenza gene. In certain such embodiments, the single influenza gene is a second HA gene. This aspect of the invention is useful in situations where it is desirable to produce reassortant viruses having the NA gene from the donor strain. Use of one more expression construct(s) comprising no more than a single HA gene increases the production of 7:1 reassortant viruses because only a single second HA gene is present in the culture host. In other embodiments, the single influenza gene is a second NA gene. This aspect of the invention is useful in situations where it is desirable to produce reassortant viruses having the HA gene from the donor strain. Use of one more expression construct(s) comprising no more than a single NA gene increases the production of 7:1 reassortant viruses because only a single second NA gene is present in the culture host. These embodiments of the invention may be particularly useful when seeking to produce reassortant influenza B virus because reassortant influenza B viruses having desirable characteristics may contain the NA segment of the parent influenza B strain.

In certain embodiments, the one or more expression construct(s) are introduced into the culture host at the same time as the culture host is contacted with the donor strain. Introduction of the one or more expression construct(s) into the culture host at the same time as the culture host is contacted with the donor strain can also be described as co-delivery. The inventors have found that delivery of the expression construct(s) and infection with the donor strain at the same time enhances the production of reassortant influenza viruses. In the context of the present invention, the same time means within 5 minutes. As a result, contacting the culture host with the donor strain followed by the introduction of the one or more expression construct(s) to the culture host up to 5 minutes later is considered to be delivery at the same time.

In one embodiment, co-delivery of the one or more expression construct(s) and contacting the culture host with the donor strain comprises co-transfection of the expression construct(s) and purified donor strain. In certain such embodiments, the one or more expression construct(s) are mixed with the purified parent influenza strain and delivered to the host cell using any transfection method known to those skilled in the art. Suitable transfection methods include electroporation, DEAE-dextran, calcium phosphate precipitation, liposomes, microinjection, microparticle-bombardment, or other transfection reagents.

In other embodiments, the one or more expression construct(s) are introduced into the culture host before the culture host is contacted with the donor strain. In other embodiments, the one or more expression construct(s) are introduced into the culture host after the culture host is contacted with the donor strain. In certain embodiments the time difference between contacting the culture host and introduction of the one or more expression constructs is no more than 10, 20, 30, 40, 50, 60, 90, 120 or 180 minutes. In other embodiments the time difference between contacting the culture host and introduction of the one or more expression constructs is no more than 3, 4, 5, 6, 8, 10, 12, 18 or 24 hours. In certain embodiments the time difference between contacting the culture host and introduction of the one or more expression constructs is 1-3 hours. Such staggered delivery may be advantageous in circumstances were co-delivery is not practical.

The one or more expression construct(s) introduced into the culture host may contain influenza A virus HA subtypes H1, H2, H3, H4, H5, H6, H7, H8, H9, H10, H11, H12, H13, H14, H15 or H16. They may contain the influenza A virus NA subtypes N1, N2, N3, N4, N5, N6, N7, N8 or N9. The one or more expression construct(s) introduced into the culture host may comprise one or more influenza genes from a seasonal influenza strain. In these embodiments, the one or more expression construct(s) may, for example, contain an HA having an H1 or H3 subtype. In one embodiment of the invention the one or more expression construct(s) comprise influenza genes from a vaccine strain which is a H1N1 or H3N2 strain.

Production, Selection and Isolation of Reassortant Viruses

The reassortant viruses produced by culturing a culture host that has been contacted with the donor strain, and to which one or more expression constructs comprising a second HA gene or second NA gene have been introduced, comprise influenza genes from the donor strain and the second HA gene or the second NA gene that are encoded by the one or more expression construct(s). In a preferred embodiment, the reassortant viruses produced by culturing a culture host that has been contacted with the donor strain, and to which one or more expression constructs comprising a second HA gene and second NA gene have been introduced, comprise influenza genes from the donor strain and the second HA gene and second NA gene that are encoded by the one or more expression construct(s). In further embodiments, the reassortant viruses produced by culturing a culture host that has been contacted with the donor strain, and to which one or more expression constructs comprising a second HA gene, a second NA gene, and a second backbone gene (i.e. a PB1, PB2, PA, M, NS or NP gene) have been introduced, comprise influenza genes from the donor strain, the second HA gene, second NA gene and second backbone gene that are encoded by the one or more expression construct(s).

The methods of the invention also further comprise a selection step to enhance the production of reassortant viruses comprising the second HA gene (i.e. the vaccine strain's HA gene). The selection step may comprise any method that enhances the selection of reassortant viruses comprising an HA derived from the vaccine strain (the second HA gene). In some embodiments, the selection step is carried out after the culture host has been cultured in order to produce reassortant influenza viruses. Accordingly, in some embodiments, the methods of the invention comprise the steps of: (i) contacting a culture host with a parent influenza virus strain comprising a first hemagglutinin (HA) gene and a first neuraminidase (NA) gene; (ii) introducing into the culture host one or more expression construct(s) comprising one or more influenza genes, wherein said influenza genes comprise a second HA gene or a second NA gene; (iii) culturing the culture host in order to produce reassortant viruses; and subsequently, after reassortant viruses have been produced, (iv) selecting for reassortant viruses that comprise the second HA gene or the second NA gene.

In some embodiments, the methods comprise a step of separating reassortant viruses from the culture host prior to the selection step. For instance, in certain embodiments, cell culture supernatant comprising the reassortant viruses is separated from the culture host and the selection step is performed on the supernatant that comprises the reassortant viruses.

In some embodiments, the selection step may comprise negative selection against reassortant viruses comprising the HA from the donor strain. In some embodiments, the selection step may comprises positive selection for reassortant viruses comprising the HA from the vaccine strain. In some embodiments, the selection step comprises one or more negative selection steps and one or more positive selections steps. In other embodiments, the selection step comprises one or more negative selection steps but no positive selection steps. In other embodiments, the selection step comprises one or more positive selection steps but no negative selection steps. One or more negative selection step(s) may be used to enhance the production of reassortant viruses comprising an HA derived from the vaccine strain. Similarly, one or more positive selection step(s) may be used to enhance production of reassortant viruses comprising an HA derived from the vaccine strain.

Negative and/or positive selection steps may also be used to enhance production of reassortant viruses comprising other segments from the vaccine strain. In certain embodiments, the selection step enhances the selection of reassortant viruses comprising an NA derived from the vaccine strain (the second NA gene). In preferred embodiments, the selection step enhances the selection of reassortant comprising the HA and NA from the vaccine strain. In further embodiments, the selection step enhances the selection of reassortant viruses comprising the PB1, PB2, PA, M, NS or NP segment from the vaccine strain. In preferred embodiments the selection step enhances the selection of reassortant viruses comprising the vaccine strain's HA, NA and a backbone segment selected from the group consisting of PB1, PB2, PA, M, NS or NP segments.

In some embodiments, negative selection comprises contacting the culture host with one or more antibodies against the first HA protein. In some embodiments, negative selection comprises contacting reassortant viruses that have been separated from the culture host with one or more antibodies against the first HA protein. In certain embodiments, negative selection comprises contacting cell culture supernatant comprising the reassortant viruses produced by the method with one or more antibodies against the first HA protein. In certain embodiments, the antibodies are present in antisera against the first HA protein. In other embodiments, one or more monoclonal antibodies against the first HA protein are used in a negative selection step.

Negative selection may also comprise exposure of the culture host to inhibitory agents that preferentially reduce the transcription and/or translation of the donor strain's HA gene or protein relative to the vaccine strain's HA gene or protein. The preferential reduction of the donor strain's HA gene or protein levels either at the transcriptional or translational level favours the formation of reassortant influenza viruses comprising the vaccine strain's HA because the likelihood that the HA gene of the vaccine strain will be incorporated and propagated increases with their relative abundance increases. Suitable inhibitory agents will be known to the skilled person and are described elsewhere [11]. In certain embodiments, the inhibitory agent that preferentially reduces the transcription and/or translation of the donor strain's HA gene or protein is selected from the group consisting of short interfering RNAs (siRNA), double-stranded RNAs (dsRNA), micro-RNAs (miRNAs), short hairpin RNAs (shRNA), or small interfering DNAs (siDNAs) like e.g., phosphorothioate oligomers (PSOs) or phosphorodiamidate morpholino oligomer (PMOs). In certain embodiments, more than one inhibitory agent that preferentially reduces the transcription and/or translation of the donor strain's HA gene or protein is used.

In some embodiments, the method does not comprise exposure of the culture host to inhibitory agents that preferentially reduce the transcription and/or translation of the donor strain's HA gene or protein relative to the vaccine strain's HA gene or protein.

In preferred embodiments, the one or more expression construct(s) comprise a second HA gene and a second NA gene. In these embodiments, the selection step may comprise contacting the culture host with one or more antibodies against the first HA protein and/or one or more antibodies against the NA protein. In particularly preferred embodiments, the antibodies are present in antisera against the first HA and/or NA proteins. In other embodiments, one or more monoclonal antibodies against the first HA protein and/or one or more monoclonal antibodies against the first NA protein are used in a negative selection step.

In certain embodiments, the one or more expression construct(s) comprise a second PB1, PB2, PA, M, NS or NP gene. In these embodiments an additional backbone segment (i.e. a PB1, PB2, PA, M, NS or NP segment) is provided to the culture host by the vaccine strain. Such embodiments may comprise a negative selection step against the first PB1, PB2, PA, M, NS or NP gene of the donor strain in order to enhance the production of reassortant viruses containing the second PB1, PB2, PA, M, NS or NP gene segment. Negative selection using an inhibitory agents that preferentially reduce the transcription and/or translation of the donor strain's PB1, PB2, PA, M, NS or NP gene segment relative to the vaccine strain's PB1, PB2, PA, M, NS or NP gene segment are preferred. This is because the protein encoded by the backbone segment is not as readily accessible to antibodies at the surface of an influenza virion as the HA and NA protein, and so inhibiting translation or transcription of the backbone segment is more effective as a negative selection step than exposure to one or more antibodies. Nevertheless, exposure of the culture host to one or more antibodies against the second PB1, PB2, PA, M, NS or NP gene segment may alternatively, or in addition, be used as a negative selection step. In some embodiments, the method does not comprise exposure of the culture host to inhibitory agents that preferentially reduce the transcription and/or translation of the donor strain's PB1, PB2, PA, M, NS or NP gene segment relative to the vaccine strain's PB1, PB2, PA, M, NS or NP gene segment.

In some embodiments, a positive selection step comprises contacting the culture host with one or more antibodies that are specific for the second HA protein. In some embodiments, a positive selection step comprises contacting the reassortant viruses that have been separated from the culture host with one or more antibodies that are specific for the second HA protein. In certain embodiments, a positive selection step comprises contacting cell culture supernatant comprising the reassortant viruses produced by the method with one or more antibodies that are specific for the second HA protein. In this way, reassortant viruses that comprise the second HA gene can be positively selected from the culture host. In preferred embodiments, one or more antibodies used for positive selection are labelled (for example, with a magnetic bead). Labelling aids subsequent isolation of reassortant viruses comprising the second HA gene.

The methods of the invention may comprise one or more selection steps. For example, reassortant virus may be passaged multiple times in the presence of antisera. Multiple selection steps are performed to enhance the selection of reassortant influenza viruses comprising the second HA gene. In preferred embodiments, multiple selection steps are preformed to enhance selection of reassortant influenza viruses comprising the second HA gene. In certain embodiments, the methods comprise two, three, four, five or six negative selection steps. In preferred embodiments, the methods comprise two negative selection steps. In other preferred embodiments, the methods comprise three negative selection steps.

The use of one or more expression construct(s) in the methods of the invention means that the culture host comprises fewer undesirable sequence variants or quasi-species than are present in classical reassortment, when all influenza gene segments are provided by parent influenza virus strains. As a result, the method typically requires fewer selection steps to produce a desired reassortant virus. Fewer selection steps means that the reassortant virus can be produced more rapidly than in classical reassortment. Thus, in one embodiment, the methods comprise no more than a single selection step. In another embodiment, the methods comprise no more than two selection steps. In a further embodiments, the methods comprise no more than three selection steps. Selection steps may be performed concurrently (i.e. at the same time), or sequentially (i.e. one after another).

A selection step may be used to select for viruses having a particular gene constellation ratio. For instance, a selection step for or against a single gene only can be used to increase production of 7:1 viruses. In certain embodiments, negative selection is against a single influenza segment. In certain embodiments, negative selection is against an HA gene alone. In other embodiments, negative selection is against an NA gene alone. Similarly, when seeking to increase production of 6:2 reassortant viruses, negative selection is against two influenza segments. In these embodiments, selection is typically negative selection against the HA and NA segments from the donor strain.

In some embodiments, the selection step is carried out in the same culture host that is used in the first step of the method. In other embodiments, the selection step is carried out in a different culture host. In these embodiments, the virus that is produced in step (iii) of the method is transferred from the first culture host to a second culture host in which one or more negative selection steps are performed.

The first culture host and second culture host may be the same or different. In one embodiment, the first culture host is a cell and the second culture host is an embryonated hen egg.

The methods of the invention produce a pool of reassortant viruses from which a particular class of reassortant virus can be isolated. This provides a greater capacity to select for a virus certain properties than is provided by reverse genetics because fewer variants and less virus diversity is produced in reverse genetics techniques. Isolation of a particular reassortant influenza virus means that a reassortant virus having advantageous properties can be selected for further processing. For instance, a reassortant virus having high growth properties and comprising the HA and NA of the circulating influenza strain can be isolated for use a seed virus in vaccine manufacture. Accordingly, the methods of the invention may further comprise the step of isolating a reassortant influenza virus comprising the second HA gene and the second NA gene.

In certain embodiments, the method produces reassortant influenza A viruses or reassortant viruses having influenza A HA. In some embodiments, the method produces reassortant influenza A viruses or reassortant viruses having influenza A HA and NA. Analysis of vaccine seed viruses has demonstrated that 95% of influenza A seed viruses have either 6:2 or 5:3 gene constellation ratios. The methods of the present invention are therefore particularly effective at generating influenza A seed viruses because the methods provide a limited number of backbone segments, thereby increasing the likelihood of generating 6:2 or 5:3 reassortant viruses.

The reassortant influenza viruses produced by the methods of the invention may contain the influenza A virus HA subtypes H1, H2, H3, H4, H5, H6, H7, H8, H9, H10, H11, H12, H13, H14, H15 or H16. They may contain the influenza A virus NA subtypes N1, N2, N3, N4, N5, N6, N7, N8 or N9. Where the vaccine strain used in the reassortant influenza viruses of the invention is a seasonal influenza strain, the vaccine strain may have a H1 or H3 subtype. In one aspect of the invention the vaccine strain is a H1N1 or H3N2 strain.

In other embodiments, the method generates reassortant influenza B viruses or reassortant viruses having influenza B HA. In some embodiments, the method produces reassortant influenza B viruses or reassortant viruses having influenza B HA and NA. Gene constellation ratios in influenza B viruses have greater variety and are less predictable. The methods of the invention are advantageous because they provide improved control in the gene constellation ratios of the reassortant influenza B viruses. The reassortant influenza viruses produced by the methods of the invention may contain the HA segment of an influenza B strain.

In certain embodiments, the methods of the invention are used to produce reassortant influenza virus based on a pandemic strains or potentially pandemic strains. In certain embodiments, the reassortant virus comprises an HA from a pandemic strain or potentially pandemic strain. The characteristics of an influenza strain that give it the potential to cause a pandemic outbreak are: (a) it contains a new hemagglutinin compared to the hemagglutinins in currently-circulating human strains, i.e. one that has not been evident in the human population for over a decade (e.g. H2), or has not previously been seen at all in the human population (e.g. H5, H6 or H9, that have generally been found only in bird populations), such that the human population will be immunologically naïve to the strain's hemagglutinin; (b) it is capable of being transmitted horizontally in the human population; and (c) it is pathogenic to humans. In certain embodiments, the methods of the invention produce a reassortant influenza virus comprising an H5 hemagglutinin type. An H5 hemagglutinin type is preferred where the reassortant virus is used in vaccines for immunizing against pandemic influenza, such as a H5N1 strain. Other possible strains include H5N3, H9N2, H2N2, H7N1 and H7N7, and any other emerging potentially pandemic strains. The invention is suitable for producing reassortant viruses for use in a vaccine for protecting against potential pandemic virus strains that can or have spread from a non-human animal population to humans, for example a swine-origin H1N1 influenza strain.

Culture Host

A culture host for use in the methods of the present invention can be embryonated hen eggs or cells. In a preferred embodiment, the culture host is a cell culture.

One method for influenza virus growth uses specific pathogen-free (SPF) embryonated hen eggs, with virus being inoculated into, grown and purified from the egg contents (allantoic fluid). Influenza viruses may also be grown in animal cell culture and, for reasons of replication accuracy, speed and patient allergies, this growth method is preferred. If egg-based viral growth is used then one or more amino acids may be introduced into the allantoic fluid of the egg together with the virus [42].

When cells are used, the invention will typically use a cell line although, for example, primary cells may be used as an alternative. The cells will typically be mammalian. Suitable mammalian cells of origin include, but are not limited to, hamster, cattle, primate (including humans and monkeys) and dog cells. Various cell types may be used, such as kidney cells, fibroblasts, retinal cells, lung cells, etc. Examples of suitable hamster cells are the cell lines having the names BHK21 or HKCC. Suitable monkey cells are e.g. African green monkey cells, such as kidney cells as in the Vero cell line [12-14]. Suitable dog cells are e.g. kidney cells, as in the CLDK and MDCK cell line. Thus suitable cell lines include, but are not limited to: MDCK; CHO; 293T; BHK; Vero; MRC-5; PER.C6; WI-38; etc. Preferred mammalian cell lines for growing influenza viruses include: MDCK cells [15-18], derived from Madin Darby canine kidney; Vero cells [12-14], derived from African green monkey (*Cercopithecus aethiops*) kidney; or PER.C6 cells [19], derived from human embryonic retinoblasts. These cell lines are widely available e.g. from the American Type Cell Culture (ATCC) collection [20], from the Coriell Cell Repositories [21], or from the European Collection of Cell Cultures (ECACC). For example, the ATCC supplies various different Vero cells under catalog numbers CCL-81, CCL-81.2, CRL-1586 and CRL-1587, and it supplies MDCK cells under catalog number CCL-34. PER.C6 is available from the ECACC under deposit number 96022940. As a less-preferred alternative to mammalian cell lines, virus can be grown on avian cell lines [e.g. refs. 22-24], including cell lines derived from ducks (e.g. duck retina) or hens e.g. chicken embryo fibroblasts (CEF), etc. Examples include avian embryonic stem cells [22,25], including the EBx cell line derived from chicken embryonic stem cells, EB45, EB14, and EB14-074 [26]. EB66 is a preferred cell line.

Particularly preferred cells for use in the invention are MDCK cells [15-1618], derived from Madin Darby canine kidney. The original MDCK cells are available from the ATCC as CCL-34. Derivatives of MDCK cells may also be used. For instance, reference 15 discloses a MDCK cell line that was adapted for growth in suspension culture ('MDCK 33016', deposited as DSM ACC 2219). Similarly, reference 27 discloses a MDCK-derived cell line that grows in suspension in serum-free culture (B-702', deposited as FERM BP-7449). Reference 28 discloses non-tumorigenic MDCK cells, including 'MDCK-S' (ATCC PTA-6500), 'MDCK-SF101' (ATCC PTA-6501), 'MDCK-SF102' (ATCC PTA-6502) and 'MDCK-SF103' (PTA-6503). Reference 29 discloses MDCK cell lines with high susceptibility to infection, including 'MDCK.5F1' cells (ATCC CRL-12042). Any of these MDCK cell lines can be used.

For growth on a cell line, such as on MDCK cells, virus may be grown on cells in suspension [15,30,31] or in adherent culture. One preferred MDCK cell line for suspension culture is MDCK 33016 (deposited as DSM ACC 2219). As an alternative, microcarrier culture can be used.

Cell lines supporting influenza virus replication are preferably grown in serum-free culture media and/or protein free media. A medium is referred to as a serum-free medium in the context of the present invention if it contains no additives from serum of human or animal origin. Protein-free is understood to mean cultures in which multiplication of the cells occurs with exclusion of proteins, growth factors, other protein additives and non-serum proteins, but can optionally include proteins such as trypsin or other proteases that may be necessary for viral growth. The cells growing in such cultures naturally contain proteins themselves.

Cell lines supporting influenza virus replication are preferably grown below 37° C. [33] (e.g. 30-36° C., or at about 30° C., 31° C., 32° C., 33° C., 34° C., 35° C., 36° C.), for example during viral replication.

Where virus is grown on a cell line then the growth culture, and also the viral inoculum used to start the culture, is preferably free from (i.e. will have been tested for and given a negative result for contamination by) herpes simplex virus, respiratory syncytial virus, parainfluenza virus 3, SARS coronavirus, adenovirus, rhinovirus, reoviruses, polyomaviruses, birnaviruses, circoviruses, and/or parvoviruses [32].

Where virus has been grown on a mammalian cell line then the composition will advantageously be free from egg proteins (e.g. ovalbumin and ovomucoid) and from chicken DNA, thereby reducing allergenicity. The avoidance of allergens is useful for minimizing Th2 responses. Where cells are used as a culture host in the methods of the invention, it is known that cell culture conditions (e.g. temperature, cell density, pH value, etc.) are variable over a wide range subject to the cell line and the influenza virus strain employed and can be adapted to the requirements of the application. The following information therefore merely represents guidelines.

Multiplication of the cells can be conducted in accordance with methods known to those of skill in the art. For example, the cells can be cultivated in a perfusion system using ordinary support methods like centrifugation or filtration. Moreover, the cells can be multiplied according to the invention in a fed-batch system before infection. In the context of the present invention, a culture system is referred to as a fed-batch system in which the cells are initially cultured in a batch system and depletion of nutrients (or part of the nutrients) in the medium is compensated by controlled feeding of concentrated nutrients. It can be advantageous to adjust the pH value of the medium during multiplication of cells before infection to a value between pH 6.6 and pH 7.8 and especially between a value between pH 7.2 and pH 7.3. Culturing of cells preferably occurs at a temperature between 30 and 40° C. After infection with the influenza viruses, the cells are preferably cultured at a temperature of between 30° C. and 36° C. or between 32° C. and 34° C. or at about 33° C. This is particularly preferred as it has been shown that incubation of infected cells in this temperature range results in production of a virus that results in improved efficacy when formulated into a vaccine [33]. The oxygen partial pressure can be adjusted during culturing before infection preferably at a value between 25% and 95% and especially at a value between 35% and 60%. The values for the oxygen partial pressure stated in the context of the invention are based on saturation of air. Infection of cells occurs at a cell density of preferably about $8\text{-}25\times10^5$ cells/mL in the batch system or preferably about $5\text{-}20\times10^6$ cells/mL in the perfusion system. The cells can be infected with a viral dose (MOI value, "multiplicity of infection"; corresponds to the number of virus units per cell at the time of infection) between $10^{-8}$ and 10, preferably between 0.0001 and 0.5.

The methods according to the invention can include harvesting and isolation of viruses or the proteins generated by them. During isolation of viruses or proteins, the cells are separated from the culture medium by standard methods like separation, filtration or ultrafiltration. The viruses or the proteins are then concentrated according to methods known to those skilled in the art, like gradient centrifugation, filtration, precipitation, chromatography, etc., and then purified. It is preferred that the viruses are inactivated during or after purification. Virus inactivation can occur, for example, by β-propiolactone or formaldehyde at any point within the purification process.

Host Cell DNA

Where virus has been isolated and/or grown on a cell line, it is standard practice to minimize the amount of residual cell line DNA in the final vaccine, in order to minimize any potential oncogenic activity of the DNA.

Thus a vaccine composition prepared according to the invention preferably contains less than 10 ng (preferably less than 1 ng, and more preferably less than 100 pg) of residual host cell DNA per dose, although trace amounts of host cell DNA may be present.

It is preferred that the average length of any residual host cell DNA is less than 500 bp e.g. less than 400 bp, less than 300 bp, less than 200 bp, less than 100 bp, etc.

Contaminating DNA can be removed during vaccine preparation using standard purification procedures e.g. chromatography, etc. Removal of residual host cell DNA can be enhanced by nuclease treatment e.g. by using a DNase. A convenient method for reducing host cell DNA contamination is disclosed in references 34 & 35, involving a two-step treatment, first using a DNase (e.g. Benzonase), which may be used during viral growth, and then a cationic detergent (e.g. CTAB), which may be used during virion disruption. Treatment with an alkylating agent, such as β-propiolactone, can also be used to remove host cell DNA, and advantageously may also be used to inactivate virions [36].

Vaccines

The invention utilises virus produced according to the method to produce vaccines.

Influenza vaccines are generally based either on live virus or on inactivated virus. Inactivated vaccines may be based on whole virions, 'split' virions, or on purified surface antigens. Antigens can also be presented in the form of virosomes. The invention can be used for manufacturing any of these types of vaccine.

Where an inactivated influenza virus is used, the vaccine may comprise whole virion, split virion, or purified surface antigens (including hemagglutinin and, usually, also including neuraminidase). Chemical means for inactivating a virus include treatment with an effective amount of one or more of the following agents: detergents, formaldehyde, β-propiolactone, methylene blue, psoralen, carboxyfullerene (C60), binary ethylamine, acetyl ethyleneimine, or combinations thereof. Non-chemical methods of viral inactivation are known in the art, such as for example UV light or gamma irradiation.

Virions can be harvested from virus-containing fluids, e.g. allantoic fluid or cell culture supernatant, by various methods. For example, a purification process may involve zonal centrifugation using a linear sucrose gradient solution (that optionally includes detergent to disrupt the virions) or affinity chromatography methods. Antigens may then be purified, after optional dilution, by diafiltration.

Split virions are obtained by treating purified virions with detergents (e.g. ethyl ether, polysorbate 80, deoxycholate, tri-N-butyl phosphate, Triton X-100, Triton N101, cetyltrimethylammonium bromide, Tergitol NP9, etc.) to produce subvirion preparations, including the 'Tween-ether' splitting process. Methods of splitting influenza viruses, for example are well known in the art e.g. see refs. 37-42, etc. Splitting of the virus is typically carried out by disrupting or fragmenting whole virus, whether infectious or non-infectious with a disrupting concentration of a splitting agent. The disruption results in a full or partial solubilisation of the virus proteins, altering the integrity of the virus. Preferred splitting agents are non-ionic and ionic (e.g. cationic) surfactants e.g. alkylglycosides, alkylthioglycosides, acyl sugars, sulphobetaines, betains, polyoxyethylenealkylethers, N,N-dialkyl-Glucamides, Hecameg, alkylphenoxy-polyethoxyethanols, NP9, quaternary ammonium compounds, sarcosyl, CTABs (cetyl trimethyl ammonium bromides), tri-N-butyl phosphate, Cetavlon, myristyltrimethylammonium salts, lipofectin, lipofectamine, and DOT-MA, the octyl- or nonylphenoxy polyoxyethanols (e.g. the Triton surfactants, such as Triton X-100 or Triton N101), polyoxyethylene sorbitan esters (the Tween surfactants), polyoxyethylene ethers, polyoxyethlene esters, etc. One useful splitting procedure uses the consecutive effects of sodium deoxycholate and formaldehyde, and splitting can take place during initial virion purification (e.g. in a sucrose density gradient solution). Thus a splitting process can involve clarification of the virion-containing material (to remove non-virion material), concentration of the harvested virions (e.g. using an adsorption method, such as CaHPO4 adsorption), separation of whole virions from non-virion material, splitting of virions using a splitting agent in a density gradient centrifugation step (e.g. using a sucrose gradient that contains a splitting agent such as sodium deoxycholate), and then filtration (e.g. ultrafiltration) to remove undesired materials. Split virions can usefully be resuspended in sodium phosphate-buffered isotonic sodium chloride solution. Examples of split influenza vaccines are the BEGRIVAC™, FLUARIX™, FLUZONE™ and FLUSHIELD™ products.

Purified influenza virus surface antigen vaccines comprise the surface antigens hemagglutinin and, typically, also neuraminidase. Processes for preparing these proteins in purified form are well known in the art. The FLUVIRIN™, AGRIPPAL™ and INFLUVAC™ products are influenza subunit vaccines.

Another form of inactivated antigen is the virosome [43] (nucleic acid free viral-like liposomal particles). Virosomes can be prepared by solubilization of virus with a detergent followed by removal of the nucleocapsid and reconstitution of the membrane containing the viral glycoproteins. An alternative method for preparing virosomes involves adding viral membrane glycoproteins to excess amounts of phospholipids, to give liposomes with viral proteins in their membrane.

The method of the invention may also be used to produce live vaccines. Such vaccines are usually prepared by purifying virions from virion-containing fluids. For example, the fluids may be clarified by centrifugation, and stabilized with buffer (e.g. containing sucrose, potassium phosphate, and monosodium glutamate). Various forms of influenza virus vaccine are currently available (e.g. see chapters 17 & 18 of reference 44). Live virus vaccines include MedImmune's FLUMIST™ product (trivalent live virus vaccine).

The virus may be attenuated. The virus may be temperature-sensitive. The virus may be cold-adapted. These three features are particularly useful when using live virus as an antigen.

HA is the main immunogen in current inactivated influenza vaccines, and vaccine doses are standardised by reference to HA levels, typically measured by SRID. Existing vaccines typically contain about 15 µg of HA per strain, although lower doses can be used e.g. for children, or in pandemic situations, or when using an adjuvant. Fractional doses such as ½ (i.e. 7.5 µg HA per strain), ¼ and ⅛ have been used, as have higher doses (e.g. 3× or 9× doses [45,46]). Thus vaccines may include between 0.1 and 150 µg of HA per influenza strain, preferably between 0.1 and 50 µg e.g. 0.1-20 µg, 0.1-15 µg, 0.1-10 µg, 0.1-7.5 µg, 0.5-5 µg, etc. Particular doses include e.g. about 45, about 30, about 15, about 10, about 7.5, about 5, about 3.8, about 3.75, about 1.9, about 1.5, etc. per strain.

For live vaccines, dosing is measured by median tissue culture infectious dose (TCID50) rather than HA content, and a TCID50 of between $10^6$ and $10^8$ (preferably between $10^{6.5}$-$10^{7.5}$) per strain is typical.

As well as being suitable for immunizing against interpandemic strains, the compositions of the invention may be useful for immunizing against pandemic or potentially-pandemic strains. The invention is suitable for vaccinating humans as well as non-human animals.

Other strains whose antigens can usefully be included in the compositions are strains which are resistant to antiviral therapy (e.g. resistant to oseltamivir [47] and/or zanamivir), including resistant pandemic strains [48].

Compositions of the invention (e.g. vaccines produced according to the invention) may include antigen(s) from one or more (e.g. 1, 2, 3, 4 or more) influenza virus strains, including influenza A virus and/or influenza B virus. Where a vaccine includes more than one strain of influenza, the different strains may be grown separately and are mixed after the viruses have been harvested and antigens have been prepared. Thus a process of the invention may include the step of mixing antigens from more than one influenza strain. A trivalent vaccine is typical, including antigens from two influenza A virus strains and one influenza B virus strain. A tetravalent vaccine is also useful [49], including antigens from two influenza A virus strains and two influenza B virus strains, or three influenza A virus strains and one influenza B virus strain.

Pharmaceutical Compositions

Vaccine compositions manufactured according to the invention are pharmaceutically acceptable. They usually include components in addition to the antigens e.g. they typically include one or more pharmaceutical carrier(s) and/or excipient(s). A "pharmaceutically acceptable carrier" includes any carrier that does not itself induce the production of antibodies harmful to the individual receiving the composition. Suitable carriers are typically large, slowly metabolised macromolecules such as proteins, polysaccharides, polylactic acids, polyglycolic acids, polymeric amino acids, amino acid copolymers, sucrose, trehalose, lactose, and lipid aggregates (such as oil droplets or liposomes). Such carriers are well known to those of ordinary skill in the art. The compositions may also contain a pharmaceutically acceptable diluent, such as water, saline, glycerol, etc. Additionally, auxiliary substances, such as wetting or emulsifying agents, pH buffering substances, and the like, may be present. Sterile pyrogen-free, phosphate-buffered physiologic saline is a typical carrier (a thorough discussion of such components is available in reference 50). As described below, adjuvants may also be included.

Vaccine compositions will generally be in aqueous form. However, some vaccines may be in dry form, e.g. in the form of injectable solids or dried or polymerized preparations on a patch.

Vaccine compositions may include preservatives such as thiomersal or 2-phenoxyethanol. It is preferred, however, that the vaccine should be substantially free from (i.e. less than 5 µg/ml) mercurial material e.g. thiomersal-free [41, 51]. Vaccines containing no mercury are more preferred. An α-tocopherol succinate can be included as an alternative to mercurial compounds [41]. Preservative-free vaccines are particularly preferred.

To control tonicity, it is preferred to include a physiological salt, such as a sodium salt. Sodium chloride (NaCl) is preferred, which may be present at between 1 and 20 mg/ml. Other salts that may be present include potassium chloride, potassium dihydrogen phosphate, disodium phosphate dehydrate, magnesium chloride, calcium chloride, etc.

Vaccine compositions will generally have an osmolality of between 200 mOsm/kg and 400 mOsm/kg, preferably between 240-360 mOsm/kg, and will more preferably fall within the range of 290-310 mOsm/kg. Osmolality has previously been reported not to have an impact on pain caused by vaccination [52], but keeping osmolality in this range is nevertheless preferred.

Vaccine compositions may include one or more buffers. Typical buffers include: a phosphate buffer; a Tris buffer; a borate buffer; a succinate buffer; a histidine buffer (particularly with an aluminium hydroxide adjuvant); or a citrate buffer. Buffers will typically be included in the 5-20 mM range.

The pH of a vaccine composition will generally be between 5.0 and 8.1, and more typically between 6.0 and 8.0 e.g. 6.5 and 7.5, or between 7.0 and 7.8. A process of the invention may therefore include a step of adjusting the pH of the bulk vaccine prior to packaging.

The vaccine composition is preferably sterile. The vaccine composition is preferably non-pyrogenic e.g. containing <1 EU (endotoxin unit, a standard measure) per dose, and preferably <0.1 EU per dose. The vaccine composition is preferably gluten-free.

Vaccine compositions of the invention may include detergent e.g. a polyoxyethylene sorbitan ester surfactant (known as 'Tweens'), an octoxynol (such as octoxynol-9 (Triton X-100) or t-octylphenoxypolyethoxyethanol), a cetyl trimethyl ammonium bromide ('CTAW), or sodium deoxycholate, particularly for a split or surface antigen vaccine. The detergent may be present only at trace amounts. Thus the vaccine may include less than 1 mg/ml of each of octoxynol-10 and polysorbate 80. Other residual components in trace amounts could be antibiotics (e.g. neomycin, kanamycin, polymyxin B).

A vaccine composition may include material for a single immunisation, or may include material for multiple immunisations (i.e. a 'multidose' kit). The inclusion of a preservative is preferred in multidose arrangements. As an alternative (or in addition) to including a preservative in multidose compositions, the compositions may be contained in a container having an aseptic adaptor for removal of material.

Influenza vaccines are typically administered in a dosage volume of about 0.5 ml, although a half dose (i.e. about 0.25 ml) may be administered to children.

Compositions and kits are preferably stored at between 2° C. and 8° C. They should not be frozen. They should ideally be kept out of direct light.

Adjuvants

Compositions of the invention (e.g. vaccines produced according to the invention) may advantageously include an adjuvant, which can function to enhance the immune responses (humoral and/or cellular) elicited in a subject who receives the composition.

The adjuvant is preferably an oil-in-water emulsion adjuvant as they have been shown to work well with influenza antigens.

Oil-In-Water Emulsion Adjuvants

Oil-in-water emulsions have been found to be particularly suitable for use in adjuvanting influenza virus vaccines. Various such emulsions are known, and they typically include at least one oil and at least one surfactant, with the oil(s) and surfactant(s) being biodegradable (metabolisable) and biocompatible. The oil droplets in the emulsion are generally less than 5 μm in diameter, and may even have a sub-micron diameter, with these small sizes being achieved with a microfluidiser to provide stable emulsions. Droplets with an average size less than 220 nm are preferred as they can be subjected to filter sterilization.

In preferred embodiments, the oil-in-water emulsion is uniform. A uniform emulsion is characterized in that a majority of droplets (particles) dispersed therein is within a specified size range (e.g., in diameter). Suitable specified size range can be, for example, between 50-220 nm, between 50-180 nm, between 80-180 nm, between 100-175 nm, between 120-185 nm, between 130-190 nm, between 135-175 nm, between 150-175 nm. In some embodiments, the uniform emulsion contains ≤10% of the number of droplets (particles) that are outside of the specified range of diameters. In some embodiments, mean particle size of oil droplets in the oil-in-water emulsion preparation is between 135-175 nm, e.g., 155 nm 20 nm as measured by dynamic light scattering, and such a preparation contains not more than $1 \times 10^7$ large particles per mL of the preparation, as measured by optical particle sensing. "Large particles" as used herein mean those having diameters >1.2 μm, typically between 1.2-400 μm. In preferred embodiments, the uniform emulsion contains less than 10%, less than 5%, or less than 3% of the droplets that fall outside of the preferred size range. In some embodiments, the mean droplet size of particles in an oil-in-water emulsion preparation is between 125-185 nm, e.g., about 130 nm, about 140 nm, about 150 nm, about 155 nm, about 160 nm, about 170 nm, or about 180 nm, and the oil-in-water emulsion is uniform in that less than 5% of the number of droplets in the preparation fall outside the 125-185 nm range.

The invention can be used with oils such as those from an animal (such as fish) or vegetable source. Sources for vegetable oils include nuts, seeds and grains. Peanut oil, soybean oil, coconut oil, and olive oil, the most commonly available, exemplify the nut oils. Jojoba oil can be used e.g. obtained from the jojoba bean. Seed oils include safflower oil, cottonseed oil, sunflower seed oil, sesame seed oil and the like. In the grain group, corn oil is the most readily available, but the oil of other cereal grains such as wheat, oats, rye, rice, teff, triticale and the like may also be used. 6-10 carbon fatty acid esters of glycerol and 1,2-propanediol, while not occurring naturally in seed oils, may be prepared by hydrolysis, separation and esterification of the appropriate materials starting from the nut and seed oils. Fats and oils from mammalian milk are metabolizable and may therefore be used in the practice of this invention. The procedures for separation, purification, saponification and other means necessary for obtaining pure oils from animal sources are well known in the art. Most fish contain metabolizable oils which may be readily recovered. For example, cod liver oil, shark liver oils, and whale oil such as spermaceti exemplify several of the fish oils which may be used herein. A number of branched chain oils are synthesized biochemically in 5-carbon isoprene units and are generally referred to as terpenoids. Shark liver oil contains a branched, unsaturated terpenoids known as squalene, 2,6,10,15,19,23-hexamethyl-2,6,10,14,18,22-tetracosahexaene, which is particularly preferred herein. Squalane, the saturated analog to squalene, is also a preferred oil. Fish oils, including squalene and squalane, are readily available from commercial sources or may be obtained by methods known in the art. Other preferred oils are the tocopherols (see below). Mixtures of oils can be used.

Surfactants can be classified by their 'HLB' (hydrophile/lipophile balance). Preferred surfactants of the invention have a HLB of at least 10, preferably at least 15, and more preferably at least 16. The invention can be used with surfactants including, but not limited to: the polyoxyethylene sorbitan esters surfactants (commonly referred to as the Tweens), especially polysorbate 20 and polysorbate 80; copolymers of ethylene oxide (EO), propylene oxide (PO), and/or butylene oxide (BO), sold under the DOWFAX™ tradename, such as linear EO/PO block copolymers; octoxynols, which can vary in the number of repeating ethoxy (oxy-1,2-ethanediyl) groups, with octoxynol-9 (Triton X-100, or t-octylphenoxypolyethoxyethanol) being of particular interest; (octylphenoxy)polyethoxyethanol (IGEPAL CA-630/NP-40); phospholipids such as phosphatidylcholine (lecithin); polyoxyethylene fatty ethers derived from lauryl, cetyl, stearyl and oleyl alcohols (known as Brij surfactants), such as triethyleneglycol monolauryl ether (Brij 30); and sorbitan esters (commonly known as the SPANs), such as sorbitan trioleate (Span 85) and sorbitan monolaurate. Non-ionic surfactants are preferred. Preferred surfactants for including in the emulsion are Tween 80 (polyoxyethylene sorbitan monooleate), Span 85 (sorbitan trioleate), lecithin and Triton X-100.

Mixtures of surfactants can be used, e.g., Tween 80/Span 85 mixtures. A combination of a polyoxyethylene sorbitan ester such as polyoxyethylene sorbitan monooleate (Tween 80) and an octoxynol such as t-octylphenoxypolyethoxyethanol (Triton X-100) is also suitable. Another useful combination comprises laureth 9 plus a polyoxyethylene sorbitan ester and/or an octoxynol.

Preferred amounts of surfactants (% by weight) are: polyoxyethylene sorbitan esters (such as Tween 80) 0.01 to 1%, in particular about 0.1%; octyl- or nonylphenoxy polyoxyethanols (such as Triton X-100, or other detergents in the Triton series) 0.001 to 0.1%, in particular 0.005 to 0.02%; polyoxyethylene ethers (such as laureth 9) 0.1 to 20%, preferably 0.1 to 10% and in particular 0.1 to 1% or about 0.5%.

The most preferred oil-in-water emulsions are squalene-in-water emulsions, preferably submicron squalene-in-water emulsions.

Specific oil-in-water emulsions useful with the invention include, but are not limited to, the following, from which squalene-containing emulsions are preferred:

A submicron emulsion of squalene, polysorbate 80, and sorbitan trioleate. The emulsion may include citrate ions in the aqueous phase, e.g., 10 mM sodium citrate buffer. The emulsion may comprise 3.2-4.6 mg/ml squalene, 4.1-5.3 mg/ml polysorbate 80, and 4.1-5.3 mg/ml sorbitan trioleate. The composition of the emulsion by volume can be about 4.6% squalene, about 0.45% polysorbate 80 and about 0.5% sorbitan trioleate. The adjuvant known as "MF59" [53,54, 55] is described in more detail in chapter 10 of reference 56 and chapter 12 of reference 57. Squalene, polysorbate 80 and sorbitan trioleate may be present at a weight ratio of 9750:1175:1175. Concentrations of about 39 mg/mL squalene, about 4.7 mg/mL polysorbate 80, and about 4.7 mg/mL sorbitan trioleate are typical. A Z-average droplet size of between 155-185 nm is preferred, with a polydispersity of <0.2.

An emulsion comprising squalene, a tocopherol (in particular, DL-$\alpha$-tocopherol), and polysorbate 80. The emulsion may include phosphate buffered saline. These emulsions may have by volume from 2 to 10% squalene, from 2 to 10% tocopherol and from 0.3 to 3% polysorbate 80, and the weight ratio of squalene:tocopherol is preferably <1 (e.g., 0.90) as this can provide a more stable emulsion. Squalene and polysorbate 80 may be present volume ratio of about 5:2 or at a weight ratio of about 11:5. Thus the three components (squalene, tocopherol, polysorbate 80) may be present at a weight ratio of 1068:1186:485 or around 55:61:25. One such emulsion ("AS03") includes 4.3% by weight squalene, 4.8% by weight tocopherol, and 2% by weight polysorbate 80. Concentrations of about 42.7 mg/mL squalene, about 47.4 mg/mL DL-$\alpha$-tocopherol, and about 19.4 mg/mL polysorbate 80 are typical. A Z-average droplet size of between 140-170 nm is preferred. The emulsion may also include a 3-de-O-acylated monophosphoryl lipid A (3d MPL). Another useful emulsion of this type may comprise, per human dose, 0.5-10 mg squalene, 0.5-11 mg tocopherol, and 0.1-4 mg polysorbate 80 [58], e.g., in the ratios discussed above.

An emulsion comprising squalene, an aqueous solvent, a polyoxyethylene alkyl ether hydrophilic nonionic surfactant (e.g., polyoxyethylene (12) cetostearyl ether) and a hydrophobic nonionic surfactant (e.g., a sorbitan ester or mannide ester, such as sorbitan monoleate or 'Span 80'). The emulsion is preferably thermoreversible and/or has at least 90% of the oil droplets (by volume) with a size less than 200 nm [59]. The emulsion may also include one or more of: alditol; a cryoprotective agent (e.g. a sugar, such as dodecylmaltoside and/or sucrose); and/or an alkylpolyglycoside. The emulsion may include a TLR4 agonist [60]. Such emulsions may be lyophilized. A preferred emulsion includes squalene, sorbitan oleate, polyoxyethylene cetostearyl ether and mannitol (e.g., 32.5% squalene, 4.82% sorbitan oleate, 6.18% polyoxyethylene cetostearyl ether and 6% mannitol; % s by weight), with an average droplet size below 150 nm. Concentrations of about 49.6 mg/mL squalene, about 7.6 mg/mL sorbitan oleate, and about 9.6 mg/mL polyoxyethylene cetostearyl ether, and 9.2 mg/mL mannitol are typical.

An emulsion comprising squalene, phosphatidylcholine, poloxamer 188, glycerol and an ammonium phosphate buffer [61], optionally also including an $\alpha$-tocopherol ('SE').

An emulsion of squalene, a tocopherol, and a Triton detergent (e.g. Triton X-100). The emulsion may also include a 3d-MPL (see below). The emulsion may contain a phosphate buffer.

An emulsion comprising a polysorbate (e.g., polysorbate 80), a Triton detergent (e.g., Triton X-100) and a tocopherol (e.g., an $\alpha$-tocopherol succinate). The emulsion may include these three components at a mass ratio of about 75:11:10 (e.g., 750 $\mu$g/ml polysorbate 80, 110 $\mu$g/ml Triton X-100 and 100 $\mu$g/ml $\alpha$-tocopherol succinate), and these concentrations should include any contribution of these components from antigens. The emulsion may also include squalene. The aqueous phase may contain a phosphate buffer.

An emulsion of squalane, polysorbate 80 and poloxamer 401 ("Pluronic™ L121"). The emulsion can be formulated in phosphate buffered saline, pH 7.4. This emulsion is a useful delivery vehicle for muramyl dipeptides, and has been used with threonyl-MDP in the "SAF-1" adjuvant [62] (0.05-1% Thr-MDP, 5% squalane, 2.5% Pluronic L121 and 0.2% polysorbate 80). It can also be used without the Thr-MDP, as in the "AF" adjuvant [63] (5% squalane, 1.25% Pluronic L121 and 0.2% polysorbate 80). Microfluidisation is preferred.

An emulsion of squalene, poloxamer 105 and Abil-Care [64]. The final concentration (weight) of these components in adjuvanted vaccines are 5% squalene, 4% poloxamer 105 (pluronic polyol) and 2% Abil-Care 85 (Bis-PEG/PPG-16/16 PEG/PPG-16/16 dimethicone; caprylic/capric triglyceride).

An emulsion having from 0.5-50% oil, 0.1-10% phospholipid, and 0.05-5% non-ionic surfactant. As described in reference 65, preferred phospholipid components are phosphatidylcholine, phosphatidylethanolamine, phosphatidylserine, phosphatidylinositol, phosphatidylglycerol, phosphatidic acid, sphingomyelin and cardiolipin. Submicron droplet sizes are advantageous.

A submicron oil-in-water emulsion of a non-metabolizable oil (such as light mineral oil) and at least one surfactant (such as lecithin, Tween 80 or Span 80). Additives may be included, such as QuilA saponin, cholesterol, a saponin-lipophile conjugate (such as GPI-0100, described in reference 66, produced by addition of aliphatic amine to desacylsaponin via the carboxyl group of glucuronic acid), dimethyldioctadecylammonium bromide and/or N,N-dioctadecyl-N,N-bis (2-hydroxyethyl)propanediamine.

An emulsion in which a saponin (e.g., QuilA or QS21) and a sterol (e.g., a cholesterol) are associated as helical micelles [67].

An emulsion comprising a mineral oil, a non-ionic lipophilic ethoxylated fatty alcohol, and a non-ionic hydrophilic surfactant (e.g., an ethoxylated fatty alcohol and/or polyoxyethylene-polyoxypropylene block copolymer) [68].

To make a vaccine for injection these emulsions will generally be mixed with an aqueous immunogen preparation. This mixing typically involves the emulsion in aqueous form with the immunogen in aqueous form at a 1:1 volume ratio, in which case the proportion of the emulsion's components will be halved in a final vaccine. For instance, an emulsion with 5% by volume squalene can be mixed at a 1:1 ratio with an antigen solution to give a vaccine with a final concentration of 2.5% by volume. Other mixing ratios are, of course, possible e.g. using a volume ratio of the two liquids for mixing between 5:1 and 1:5. Thus in a vaccine composition the concentrations of components of the emulsions noted above may be modified by dilution (e.g., by an integer, such as 2 or 3) in which their ratios stay the same.

For example, pediatric vaccines may contain lower concentrations of an adjuvant, e.g., 4%, 3.5%, 3%, 2.5%, 2%, 1.5%, or 1% by volume squalene.

After the antigen and adjuvant have been mixed, hemagglutinin antigen will generally remain in aqueous solution but may distribute itself around the oil/water interface. In general, little if any hemagglutinin will enter the oil phase of the emulsion.

Where a composition includes a tocopherol, any of the α, β, γ, δ, ξ or tocopherols can be used, but α-tocopherols are preferred. The tocopherol can take several forms, e.g., different salts and/or isomers. Salts include organic salts, such as succinate, acetate, nicotinate, etc. D-α-tocopherol and DL-α-tocopherol can both be used. Tocopherols are advantageously included in vaccines for use in elderly patients (e.g., aged 60 years or older) because vitamin E has been reported to have a positive effect on the immune response in this patient group [69]. They also have antioxidant properties that may help to stabilize the emulsions [70]. A preferred α-tocopherol is DL-α-tocopherol, and the preferred salt of this tocopherol is the succinate. The succinate salt has been found to cooperate with TNF-related ligands in vivo. Moreover, α-tocopherol succinate is known to be compatible with influenza vaccines and to be a useful preservative as an alternative to mercurial compounds [41]. Preservative-free vaccines are particularly preferred.

Packaging of Vaccine Compositions

Suitable containers for compositions of the invention (or kit components) include vials, syringes (e.g. disposable syringes), nasal sprays, etc. These containers should be sterile.

Where a composition/component is located in a vial, the vial is preferably made of a glass or plastic material. The vial is preferably sterilized before the composition is added to it. To avoid problems with latex-sensitive patients, vials are preferably sealed with a latex-free stopper, and the absence of latex in all packaging material is preferred. The vial may include a single dose of vaccine, or it may include more than one dose (a 'multidose' vial) e.g. 10 doses. Preferred vials are made of colourless glass.

A vial can have a cap (e.g. a Luer lock) adapted such that a pre-filled syringe can be inserted into the cap, the contents of the syringe can be expelled into the vial (e.g. to reconstitute lyophilised material therein), and the contents of the vial can be removed back into the syringe. After removal of the syringe from the vial, a needle can then be attached and the composition can be administered to a patient. The cap is preferably located inside a seal or cover, such that the seal or cover has to be removed before the cap can be accessed. A vial may have a cap that permits aseptic removal of its contents, particularly for multidose vials.

Where a component is packaged into a syringe, the syringe may have a needle attached to it. If a needle is not attached, a separate needle may be supplied with the syringe for assembly and use. Such a needle may be sheathed. Safety needles are preferred. 1-inch 23-gauge, 1-inch 25-gauge and ⅝-inch 25-gauge needles are typical. Syringes may be provided with peel-off labels on which the lot number, influenza season and expiration date of the contents may be printed, to facilitate record keeping. The plunger in the syringe preferably has a stopper to prevent the plunger from being accidentally removed during aspiration. The syringes may have a latex rubber cap and/or plunger. Disposable syringes contain a single dose of vaccine. The syringe will generally have a tip cap to seal the tip prior to attachment of a needle, and the tip cap is preferably made of a butyl rubber. If the syringe and needle are packaged separately then the needle is preferably fitted with a butyl rubber shield. Preferred syringes are those marketed under the trade name "Tip-Lok"™.

Containers may be marked to show a half-dose volume e.g. to facilitate delivery to children. For instance, a syringe containing a 0.5 ml dose may have a mark showing a 0.25 ml volume.

Where a glass container (e.g. a syringe or a vial) is used, then it is preferred to use a container made from a borosilicate glass rather than from a soda lime glass.

A kit or composition may be packaged (e.g. in the same box) with a leaflet including details of the vaccine e.g. instructions for administration, details of the antigens within the vaccine, etc. The instructions may also contain warnings e.g. to keep a solution of adrenaline readily available in case of anaphylactic reaction following vaccination, etc.

Methods of Treatment, and Administration of the Vaccine

The invention provides a vaccine manufactured according to the invention. These vaccine compositions are suitable for administration to human or non-human animal subjects, such as pigs, and the invention provides a method of raising an immune response in a subject, comprising the step of administering a vaccine composition of the invention to the subject. The invention also provides a composition of the invention for use as a medicament, and provides the use of a composition of the invention for the manufacture of a medicament for raising an immune response in a subject.

The immune response raised by these methods and uses will generally include an antibody response, preferably a protective antibody response. Methods for assessing antibody responses, neutralising capability and protection after influenza virus vaccination are well known in the art. Human studies have shown that antibody titers against hemagglutinin of human influenza virus are correlated with protection (a serum sample hemagglutination-inhibition titer of about 30-40 gives around 50% protection from infection by a homologous virus) [71]. Antibody responses are typically measured by hemagglutination inhibition, by microneutralisation, by single radial immunodiffusion (SRID), and/or by single radial hemolysis (SRH). These assay techniques are well known in the art. Compositions of the invention can be administered in various ways. The most preferred immunisation route is by intramuscular injection (e.g. into the arm or leg), but other available routes include subcutaneous injection, intranasal [72-74], oral [75], intradermal [76,77], transcutaneous, transdermal [78], etc.

Vaccines prepared according to the invention may be used to treat both children and adults. Influenza vaccines are currently recommended for use in pediatric and adult immunisation, from the age of 6 months. Thus a human subject may be less than 1 year old, 1-5 years old, 5-15 years old, 15-55 years old, or at least 55 years old. Preferred subjects for receiving the vaccines are the elderly (e.g. ≥50 years old, ≥60 years old, and preferably ≥65 years), the young (e.g. ≤5 years old), hospitalised subjects, healthcare workers, armed service and military personnel, pregnant women, the chronically ill, immunodeficient subjects, subjects who have taken an antiviral compound (e.g. an oseltamivir or zanamivir compound; see below) in the 7 days prior to receiving the vaccine, people with egg allergies and people travelling abroad. The vaccines are not suitable solely for these groups, however, and may be used more generally in a population. For pandemic strains, administration to all age groups is preferred.

Preferred compositions of the invention satisfy 1, 2 or 3 of the CPMP criteria for efficacy. In adults (18-60 years), these criteria are: (1)≥70% seroprotection; (2)≥40% seroconversion; and/or (3) a GMT increase of ≥2.5-fold. In elderly (≥60 years), these criteria are: (1)≥60% seroprotection; (2)≥30% seroconversion; and/or (3) a GMT increase of ≥2-fold. These criteria are based on open label studies with at least 50 patients.

Treatment can be by a single dose schedule or a multiple dose schedule. Multiple doses may be used in a primary immunisation schedule and/or in a booster immunisation schedule. In a multiple dose schedule the various doses may be given by the same or different routes e.g. a parenteral prime and mucosal boost, a mucosal prime and parenteral boost, etc. Administration of more than one dose (typically two doses) is particularly useful in immunologically naïve patients e.g. for people who have never received an influenza vaccine before, or for vaccinating against a new HA subtype (as in a pandemic outbreak). Multiple doses will typically be administered at least 1 week apart (e.g. about 2 weeks, about 3 weeks, about 4 weeks, about 6 weeks, about 8 weeks, about 10 weeks, about 12 weeks, about 16 weeks, etc.).

Vaccines produced by the invention may be administered to patients at substantially the same time as (e.g. during the same medical consultation or visit to a healthcare professional or vaccination centre) other vaccines e.g. at substantially the same time as a measles vaccine, a mumps vaccine, a rubella vaccine, a MMR vaccine, a varicella vaccine, a MMRV vaccine, a diphtheria vaccine, a tetanus vaccine, a pertussis vaccine, a DTP vaccine, a conjugated *H. influenzae* type b vaccine, an inactivated poliovirus vaccine, a hepatitis B virus vaccine, a meningococcal conjugate vaccine (such as a tetravalent A-C-W135-Y vaccine), a respiratory syncytial virus vaccine, a pneumococcal conjugate vaccine, etc. Administration at substantially the same time as a pneumococcal vaccine and/or a meningococcal vaccine is particularly useful in elderly patients.

Similarly, vaccines of the invention may be administered to patients at substantially the same time as (e.g. during the same medical consultation or visit to a healthcare professional) an antiviral compound, and in particular an antiviral compound active against influenza virus (e.g. oseltamivir and/or zanamivir). These antivirals include neuraminidase inhibitors, such as a (3R,4R,5S)-4-acetylamino-5-amino-3 (1-ethylpropoxy)-1-cyclohexene-1-carboxylic acid or 5-(acetylamino)-4-[(aminoiminomethyl)-amino]-2,6-an-hydro-3,4,5-trideoxy-D-glycero-D-galactonon-2-enonic acid, including esters thereof (e.g. the ethyl esters) and salts thereof (e.g. the phosphate salts). A preferred antiviral is (3R,4R,5S)-4-acetylamino-5-amino-3(1-ethylpropoxy)-1-cyclohexene-1-carboxylic acid, ethyl ester, phosphate (1:1), also known as oseltamivir phosphate (TAMIFLU™).

Definitions

The term "comprising" encompasses "including" as well as "consisting" e.g. a composition "comprising" X may consist exclusively of X or may include something additional e.g. X+Y.

The word "substantially" does not exclude "completely" e.g. a composition which is "substantially free" from Y may be completely free from Y. Where necessary, the word "substantially" may be omitted from the definition of the invention.

The term "about" in relation to a numerical value x is optional and means, for example, x±10%.

EXAMPLES

Materials and Methods

Unless otherwise indicated, the following materials and methods were used in the following examples.

Cells, Viruses and Antiserum 293T cells were obtained from Melbourne University and were maintained in DMEM containing 10% FBS, 1×Gluta-MAX (Gibco) and 1× antibiotic/antimycotic (Gibco). MDCK (WHO) cells were obtained from the WHO and were maintained in DMEM containing 10% FBS, 1×GlutaMAX (Gibco) and 1×antibiotic/antimycotic (Gibco). MDCK 33016PF cells [79] were maintained in chemically defined medium (Lonza).

The A/Texas/1/1977 high growth parent (HGP) virus (a 5:3 reassortant with PR8) was obtained from D274 (Seqirus). The PR8 HGP virus was generated using reverse genetics. Viruses were propagated in embryonated chicken eggs.

Trypsin periodate-treated sheep antisera to A/PR/8/1934 and A/Texas/1/1977 were generated at Seqirus.

Plasmids

Plasmids containing the HA and NA of PR8 (H1N1), A/Wyoming/3/2003 (H3N2), and A/Indonesia/NIHRD11771/2011 (H5N1) in the pHW2000 vector [80] were generated using standard molecular biology techniques. For H6N1, plasmids encoding H6 (A/turkey/Massachusetts/3740/1965) and N1 (A/Brisbane/59/2007 and A/California/07/2009) were generated using standard molecular biology techniques.

Purification of HGP Viruses

High growth parent viruses (PR8 and A/Texas/1/1977) were purified prior to infection of the culture host. For each parent influenza virus strain, 2 ml of infected allantoic fluid was filtered through a 0.45 μm filter, and purified by centrifugation using a Microsep 300K Omega centrifugal device (PALL), at approximately 1400× g for 1 hr. Retained virus was diluted in phosphate buffered saline (PBS)⁻ and centrifuged again using a fresh Microsep device. Retained virus was diluted to 1 ml using PBS⁻, and frozen at −80° C. in 100 μl aliquots.

Staggered Delivery of Influenza Virus Genes to Culture Host

Staggered delivery of influenza genes for the production of reassortant influenza viruses was performed by transfection of 293T/MDCK cocultures with plasmid DNA, followed by infection with the HGP at 1-24 hr post transfection. Transfection of 293T/MDCK cells with 1-2 μg of plasmids expressing viral HA and NA was performed using TransIT-293 (Minis), Lipofectamine 2000 (Invitrogen), or Lipofectamine 3000 (Invitrogen) transfection reagents according to the manufacturers' instructions.

At approximately 3 hr post-transfection, the cells were washed with PBS⁻, and the supernatant was replaced with 1 ml/well of fresh OptiMEM. The cells were then infected with HGP. TPCK-trypsin was added on day 1 post-transfection (1 μg/ml). Supernatant was collected on day 3 post-transfection.

Co-Delivery of Influenza Virus Genes to Culture Host

Co-cultures of 293T and MDCK cells (WHO or MDCK 33016PF, suspension or adherent) were co-transfected with a purified HGP virus (10-20 μl/transfection (6 well plate) of neat purified HGP virus) along with 1-2 μg each of plasmid DNA encoding viral HA and NA. Transfection reagents TransIT-293 (Minis), Lipofectamine 2000 (Invitrogen), or Lipofectamine 3000 (Invitrogen) were used according to the manufacturers' instructions. Cells transfected using TransIT-293 were washed at approximately 3 hr post transfection. TPCK-trypsin (1 μg/ml) was added at day 1 post-transfection as described previously, or 4-8 h post-transfection. Supernatant was collected on days 3-6 post-transfection.

Selection of Reassortant Influenza Viruses

Transfection supernatant subsequently underwent passaging in eggs in the presence of antiserum raised against the HGP virus. Briefly, for the first antiserum passage embryonated eggs were inoculated with 200 µl/egg of neat transfection supernatant, and an hour later were inoculated with 200 µl/egg of trypsin periodate-treated antiserum (raised against PR8 or A/Texas/1/1977, as appropriate). For the second antiserum passage, infected allantoic fluid harvested from the first antiserum passage were diluted according to HA titre and incubated for 1 hr at RT with an equal volume of antiserum, before inoculation of eggs at 200 µl/egg. For some transfections, viruses were cloned by limiting dilution.

The HA and NA genotype of the reassortants was determined by real time PCR using gene-specific primers (Geneworks) and probes (Applied Biosystems or Sigma). Reactions were prepared using Taqman RT-PCR mastermix (Applied Biosystems) and PCR was performed using a 7500 Fast Real-Time PCR system (Applied Biosystems), according to the manufacturers' instructions.

Example 1—Generation of an H5N1 (A/Indonesia/NIHRD11771/2011) Reassortant Virus An H5N1 reassortant virus was generated using a high growth parent strain (A/Texas/1/1977) and plasmids encoding the HA and NA genes of A/Indonesia/NIHRD11771/2011.

Co-cultures of 293T/MDCK (WHO) were either transfected with a plasmid encoding the HA and NA genes of A/Indonesia/NIHRD11771/2011 and subsequently infected with the high growth parent strain, or co-transfected with HA- and NA-encoding plasmids and the high growth parent strain simultaneously (Table 1).

delivered to cell culture simultaneously with the plasmid. A second antiserum passage demonstrated similar levels of virus replication for both the simultaneous transfection, as well as the experiment in which the cell culture was transfected with a plasmid prior to transfection with the high growth parent strain.

Genotyping by RT-PCR indicated both viruses to be reassortants.

Example 2—Generation of an H1N1 (A/PR/8/1934) Reassortant Virus

A reassortant H1N1 virus (A/PR/8/1934) was generated using a high growth parent strain (A/Texas/1/77) and plasmids encoding the HA and NA genes of A/PR/8/1934.

Co-cultures of 293T/MDCK (WHO) were co-transfected with the HA- and NA-encoding plasmids and the HGP simultaneously (Table 2).

TABLE 2

| | | | | | |
|---|---|---|---|---|---|
| | Rescue of A/PR/8/1934 reassortant virus. | | | | |
| Virus | Staggered HGP delivery | Co-delivered HGP | $1^{st}$ antiserum passage maximum HA titre | $2^{nd}$ antiserum passage maximum HA titre | $3^{rd}$ antiserum passage maximum HA titre |
| PR8 (co-delivered) | − | + | 422 | 86 | 1040 |

To confirm virus isolation, a third antiserum passage was performed, involving pre-incubation of virus with antisera as for the second antiserum method. Following this third antiserum passage, the HA titre of the progeny virus increased to levels typical of wild type A/PR/8/1934. Genotyping of the virus after the third antiserum passage showed the HA and NA genes of A/PR/8/1934, demonstrating successful generation of a 6:2 reassortant.

Example 3—Generation of an H3N1 (A/Wyoming/3/2003) Reassortant Virus

A reassortant H3N1 virus was generated through the use of a H1N1 HGP virus (A/PR/8/1934) and plasmids encoding the HA and NA genes of A/Wyoming/3/2003.

Co-cultures of 293T/MDCK (WHO) were either transfected with plasmids encoding the HA and NA genes of

TABLE 1

| | | | | |
|---|---|---|---|---|
| | Rescue of A/Indonesia/NIHRD11771/2011 reassortant virus | | | |
| Virus | Staggered HGP delivery | Co-delivered HGP | $1^{st}$ antiserum passage maximum HA titre | $2^{nd}$ antiserum passage maximum HA titre |
| A/Indonesia (staggered) | + | − | 65 | ≥905 |
| A/Indonesia (co-delivered) | − | + | ≥686 | ≥905 |

After transfection, the cell cultures were treated with antiserum. Following the first antiserum passage, HA titres were detected for both experiments, although higher HA titres were observed where the high growth parent had been A/Wyoming/3/2003 and subsequently infected with the HGP at approximately 3.5 h post-transfection, or co-transfected with HA- and NA-encoding plasmids and the HGP simultaneously (Table 3).

TABLE 3

| | | Rescue of A/Wyoming/3/2003 reassortant virus. | | |
|---|---|---|---|---|
| Virus | Staggered HGP delivery | Co-delivered HGP | 1st antiserum passage maximum HA titre | 2nd antiserum passage maximum HA titre |
| A/Wyoming (staggered) | + | − | 640 | 1372 |
| A/Wyoming (co-delivered) | − | + | 343 | 1280 |

Following the first antiserum passage, HA titres were detected for both the staggered HGP reassortant and the co-delivered HGP reassortant. A second antiserum passage demonstrated similar levels of virus replication for the two hybrid reassortment methods. Genotyping by real time PCR showed both viruses were reassortants.

Example 4—Generation of H6N1 Reassortant Viruses

Reassortant H6N1 viruses were generated through the use of a H3N2 HGP virus (A/Texas/1/1977) and plasmids encoding H6 (A/turkey/Massachusetts/3740/1965) and N1 (A/Brisbane/59/2007 and A/California/07/2009) genes.

Co-cultures of 293T/adherent MDCK 33016PF cells were co-transfected with HA- and NA-encoding plasmids and the HGP simultaneously (Table 4).

TABLE 4

| | | | Rescue of H6N1 reassortant virus. | | | |
|---|---|---|---|---|---|---|
| Virus | Staggered HGP delivery | Co-delivered HGP | 1st antiserum passage maximum HA titre | 2nd antiserum passage maximum HA titre | 1st cloning passage Maximum HA titre | 2nd cloning passage maximum HA titre |
| H6N1 (A/Bris NA) | − | + | +ve | 40 | 844 | 1280 |
| H6N1 (A/Cal NA) | − | + | 197 | 905 | 394 | ND |

ND—not done

Genotyping by real time PCR showed both H6N1 progeny viruses were reassortants.

Example 5—Assessment of Genetic Diversity

Genetic diversity that can arise in the context of a replicating influenza virus to produce quasi-species was assessed by comparing the sequences of non-surface influenza proteins that are present in influenza A viruses obtained by classical reassortment or reverse genetics (RG). The nucleic acid sequence of backbone genes from a pool of 10 RG viruses (originally rescued by Seqirus, CDC and NIBSC) were sequenced and then translated to determine protein sequence. These sequences compared to corresponding sequences for 16 H1N1 and 32 H3N2 viruses obtained by classical reassortment (reassortants generated by Seqirus, NYMC and NIBSC).

The analysis of M1, NP, NS1, PA and PB2 protein sequences demonstrated greater levels of sequence variation present in the reassorted viruses than the RG rescued viruses. The sequence divergence within each dataset was consistently greater for the reassortant virus datasets than for RG rescued viruses.

Figure 2:
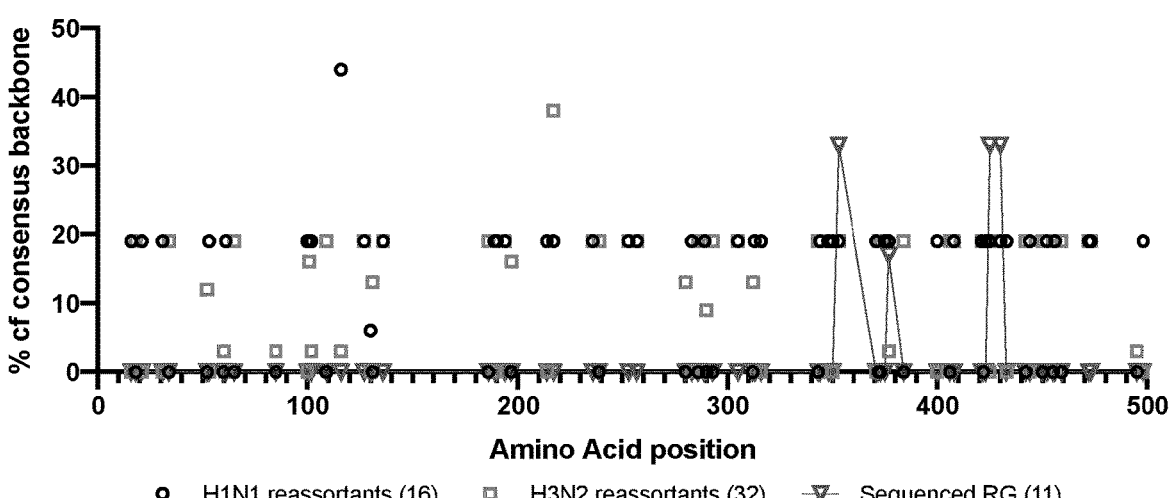
FIG. 2 is a graphical representation of the sequence variation present in NP proteins of H1N1 and H3N2 viruses produced by classical reassortment and viruses produced by reverse genetics, as described in Table 2. A 0% cf consensus backbone value indicates that there are no sequence variants present at that position. In the viruses prepared by classical reassortment, the NP proteins show variation throughout the sequence, whereas the NP proteins of viruses obtained by reverse genetics show variation at only four sequence positions.
Figure 3:
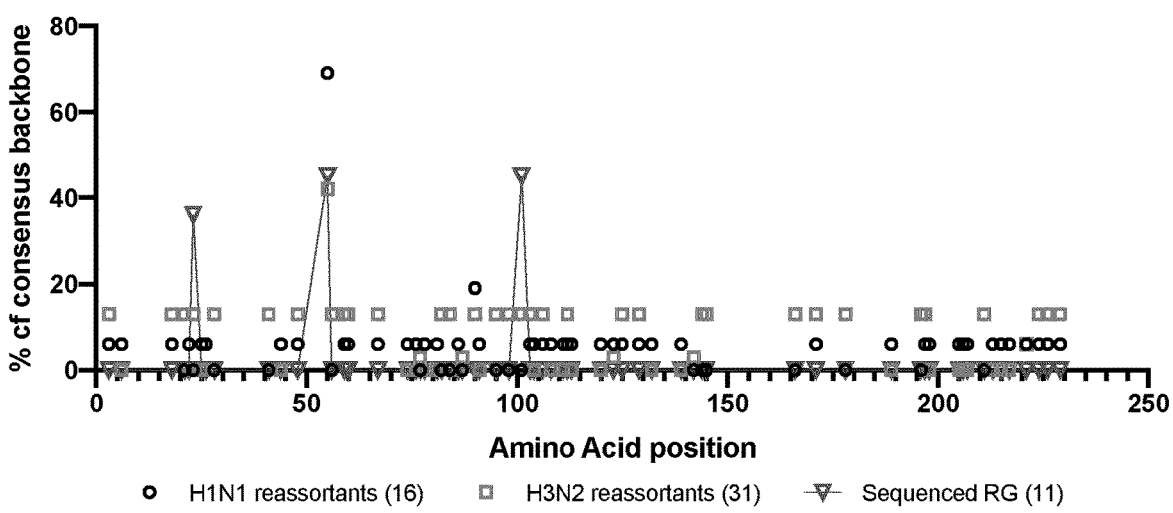
FIG. 3 is a graphical representation of the sequence variation present in NS1 proteins of H1N1 and H3N2 viruses produced by classical reassortment and viruses produced by reverse genetics, as described in Table 3. A 0% cf consensus backbone value indicates that there are no sequence variants present at that position. In the viruses prepared by classical reassortment, the NS1 proteins show variation throughout the sequence, whereas the NS1 proteins of viruses obtained by reverse genetics show variation at only three sequence positions.
Figure 4:
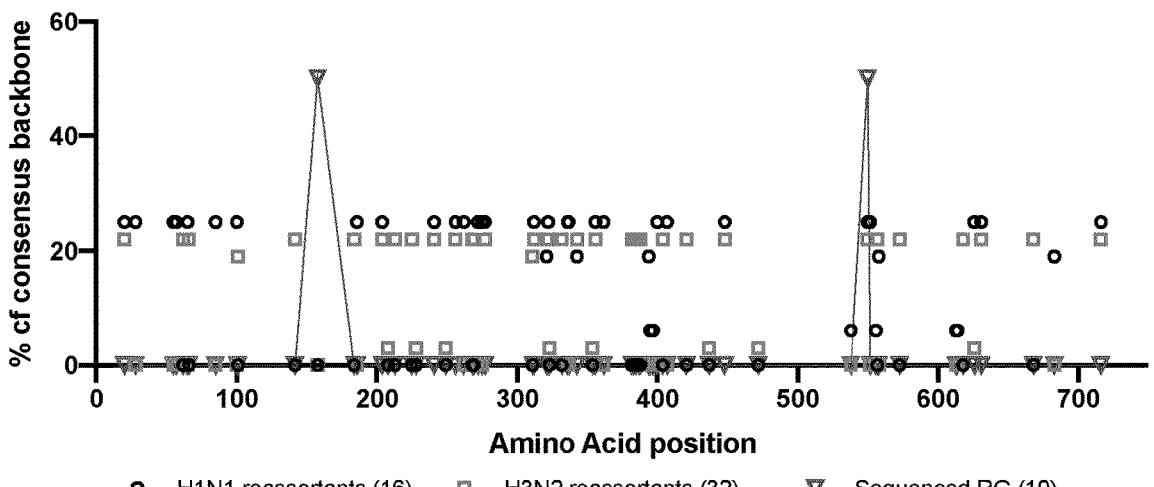
FIG. 4 is a graphical representation of the sequence variation present in PA proteins of H1N1 and H3N2 viruses produced by classical reassortment and viruses produced by reverse genetics, as described in Table 4. A 0% cf consensus backbone value indicates that there are no sequence variants present at that position. In the viruses prepared by classical reassortment, the PA proteins show variation throughout the sequence, whereas the PA proteins of viruses obtained by reverse genetics show variation at only two sequence positions.
Figure 5:
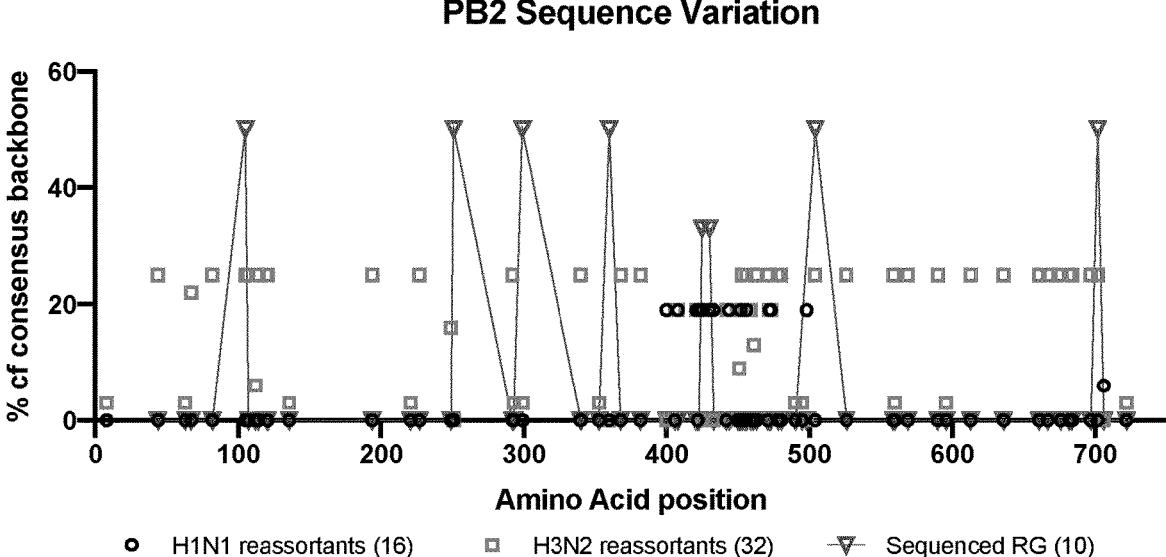
FIG. 5 is a graphical representation of the sequence variation present in PB2 segments of H1N1 and H3N2 viruses produced by classical reassortment and viruses produced by reverse genetics, as described in Table 5. A 0% cf consensus backbone value indicates that there are no sequence variants present at that position. In the viruses prepared by classical reassortment, the PB2 proteins show variation throughout the sequence, whereas the PB2 proteins of viruses obtained by reverse genetics show variation at only eight sequence positions.

Amino acid sequence variation in each backbone segment is illustrated in Tables 1-5 below. The frequency of an amino acid at specified positions is expressed as percentage of the number of sequences analysed for each source. The same data are presented in FIGS. 1-5.

TABLE 1

| | M1 protein sequence variation | | | |
|---|---|---|---|---|
| Sequence source # M1 sequences analysed | | H1N1 reassortant 16 | H3N2 reassortant 32 | RG 10 |
| Position | Amino acid | | Frequency | |
| 30 | D | 88% | 100% | 100% |
| | S | 13% | 0% | 0% |
| 41 | V | 88% | 100% | 100% |
| | A | 13% | 0% | 0% |

TABLE 1-continued

| | M1 protein sequence variation | | | |
|---|---|---|---|---|
| Sequence source # M1 sequences analysed | | H1N1 reassortant 16 | H3N2 reassortant 32 | RG 10 |
| Position | Amino acid | | Frequency | |
| 95 | K | 88% | 100% | 100% |
| | R | 13% | 0% | 0% |
| 101 | R | 88% | 100% | 100% |
| | K | 13% | 0% | 0% |
| 115 | I | 88% | 100% | 100% |
| | V | 13% | 0% | 0% |
| 121 | A | 88% | 100% | 100% |
| | T | 13% | 0% | 0% |
| 137 | A | 88% | 100% | 100% |
| | T | 13% | 0% | 0% |
| 142 | V | 88% | 100% | 100% |
| | A | 13% | 0% | 0% |
| 166 | V | 88% | 100% | 100% |
| | A | 13% | 0% | 0% |
| 207 | S | 88% | 100% | 100% |
| | N | 13% | 0% | 0% |

TABLE 1-continued

M1 protein sequence variation

| Sequence source # M1 sequences analysed | | H1N1 reassortant 16 | H3N2 reassortant 32 | RG 10 |
|---|---|---|---|---|
| Position | Amino acid | | Frequency | |
| 209 | A | 88% | 100% | 100% |
|  | T | 13% | 0% | 0% |
| 214 | Q | 88% | 100% | 100% |
|  | H | 13% | 0% | 0% |
| 231 | N | 88% | 100% | 100% |
|  | D | 13% | 0% | 0% |

TABLE 2

NP amino acid sequence variation

| Sequence source # NP sequences analysed | | H1N1 reassortant 16 | H3N2 reassortant 32 | RG 11 |
|---|---|---|---|---|
| Position | Amino acid | | Frequency | |
| 16 | D | 81% | 100% | 100% |
|  | G | 19% | 0% | 0% |
| 18 | E | 100% | 81% | 100% |
|  | D | 0% | 19% | 0% |
| 21 | N | 81% | 100% | 100% |
|  | D | 19% | 0% | 0% |
| 31 | K | 81% | 100% | 100% |
|  | R | 19% | 0% | 0% |
| 34 | G | 100% | 81% | 100% |
|  | D | 0% | 19% | 0% |
| 52 | Y | 100% | 88% | 100% |
|  | H | 0% | 9% | 0% |
|  | L | 0% | 3% | 0% |
| 53 | E | 81% | 100% | 100% |
|  | D | 19% | 0% | 0% |
| 60 | S | 100% | 97% | 100% |
|  | N | 0% | 3% | 0% |
| 61 | L | 81% | 100% | 100% |
|  | I | 19% | 0% | 0% |
| 65 | R | 100% | 81% | 100% |
|  | K | 0% | 19% | 0% |
| 85 | A | 100% | 97% | 100% |
|  | T | 0% | 3% | 0% |
| 100 | V | 81% | 100% | 100% |
|  | I | 19% | 0% | 0% |
| 101 | N | 81% | 84% | 100% |
|  | D | 19% | 16% | 0% |
| 102 | G | 81% | 97% | 100% |
|  | R | 19% | 3% | 0% |
| 109 | I | 100% | 81% | 100% |
|  | V | 0% | 19% | 0% |
| 116 | I | 56% | 97% | 100% |
|  | M | 44% | 0% | 0% |
|  | X | 0% | 3% | 0% |
| 127 | D | 81% | 81% | 100% |
|  | E | 19% | 19% | 0% |
| 130 | T | 94% | 100% | 100% |
|  | A | 6% | 0% | 0% |
| 131 | A | 100% | 88% | 100% |
|  | S | 0% | 13% | 0% |
| 136 | M | 81% | 81% | 100% |
|  | I | 19% | 19% | 0% |
| 186 | V | 100% | 81% | 100% |
|  | I | 0% | 19% | 0% |
| 189 | M | 81% | 100% | 100% |
|  | I | 19% | 0% | 0% |
| 190 | V | 81% | 100% | 100% |
|  | S | 19% | 0% | 0% |
| 194 | V | 81% | 81% | 100% |
|  | I | 19% | 19% | 0% |
| 197 | I | 100% | 84% | 100% |
|  | V | 0% | 16% | 0% |
| 214 | K | 81% | 100% | 100% |
|  | R | 19% | 0% | 0% |

TABLE 2-continued

NP amino acid sequence variation

| Sequence source # NP sequences analysed | | H1N1 reassortant 16 | H3N2 reassortant 32 | RG 11 |
|---|---|---|---|---|
| Position | Amino acid | | Frequency | |
| 217 | I | 81% | 81% | 100% |
|  | V | 19% | 0% | 0% |
|  | S | 0% | 38% | 0% |
| 236 | K | 81% | 81% | 100% |
|  | R | 19% | 19% | 0% |
| 239 | M | 100% | 81% | 100% |
|  | V | 0% | 19% | 0% |
| 253 | F | 81% | 81% | 100% |
|  | I | 19% | 19% | 0% |
| 257 | T | 81% | 81% | 100% |
|  | 1 | 19% | 19% | 0% |
| 280 | V | 100% | 88% | 100% |
|  | A | 0% | 13% | 0% |
| 283 | P | 81% | 100% | 100% |
|  | L | 19% | 0% | 0% |
| 286 | A | 100% | 81% | 100% |
|  | S | 0% | 19% | 0% |
| 289 | Y | 81% | 100% | 100% |
|  | H | 19% | 0% | 0% |
| 290 | D | 100% | 91% | 100% |
|  | N | 0% | 9% | 0% |
| 293 | R | 100% | 81% | 100% |
|  | K | 0% | 19% | 0% |
| 305 | R | 81% | 81% | 100% |
|  | K | 19% | 19% | 0% |
| 312 | V | 100% | 88% | 100% |
|  | I | 0% | 13% | 0% |
| 313 | Y | 81% | 100% | 100% |
|  | V | 19% | 0% | 0% |
| 316 | I | 81% | 100% | 100% |
|  | M | 19% | 0% | 0% |
| 343 | V | 100% | 81% | 100% |
|  | L | 0% | 19% | 0% |
| 344 | L | 81% | 100% | 100% |
|  | S | 19% | 0% | 0% |
| 348 | K | 81% | 81% | 100% |
|  | R | 19% | 19% | 0% |
| 350 | T | 81% | 100% | 100% |
|  | K | 19% | 0% | 0% |
| 353 | L | 81% | 81% | 67% |
|  | I | 19% | 0% | 0% |
|  | S | 0% | 19% | 0% |
|  | V | 0% | 0% | 33% |
| 371 | M | 81% | 100% | 100% |
|  | V | 19% | 0% | 0% |
| 372 | E | 100% | 81% | 100% |
|  | D | 0% | 19% | 0% |
| 373 | T | 100% | 81% | 100% |
|  | N | 0% | 19% | 0% |
| 375 | E | 81% | 81% | 100% |
|  | D | 19% | 0% | 0% |
|  | G | 0% | 19% | 0% |
| 377 | S | 81% | 97% | 83% |
|  | N | 19% | 0% | 17% |
|  | G | 0% | 3% | 0% |
| 384 | R | 100% | 81% | 100% |
|  | G | 0% | 19% | 0% |
| 400 | R | 81% | 100% | 100% |
|  | K | 19% | 0% | 0% |
| 406 | I | 100% | 81% | 100% |
|  | T | 0% | 19% | 0% |
| 408 | I | 81% | 81% | 100% |
|  | V | 19% | 19% | 0% |
| 421 | D | 81% | 81% | 100% |
|  | E | 19% | 19% | 0% |
| 422 | R | 100% | 81% | 100% |
|  | K | 0% | 19% | 0% |
| 423 | T | 81% | 81% | 100% |
|  | A | 19% | 0% | 0% |
|  | S | 0% | 19% | 0% |
| 425 | I | 81% | 100% | 67% |
|  | V | 19% | 0% | 33% |

TABLE 2-continued

| NP amino acid sequence variation | | | |
|---|---|---|---|
| Sequence source # NP sequences analysed | H1N1 reassortant 16 | H3N2 reassortant 32 | RG 11 |
| Position   Amino acid | Frequency | | |
| 430   N | 81% | 81% | 67% |
| S | 19% | 0% | 0% |
| T | 0% | 19% | 33% |
| 433   T | 81% | 100% | 100% |
| N | 19% | 0% | 0% |
| 442   T | 100% | 81% | 100% |
| A | 0% | 19% | 0% |
| 444   I | 81% | 100% | 100% |
| V | 19% | 0% | 0% |
| 450   S | 100% | 81% | 100% |
| G | 0% | 19% | 0% |
| 452   R | 81% | 81% | 100% |
| K | 19% | 19% | 0% |
| 455   D | 100% | 81% | 100% |
| E | 0% | 19% | 0% |
| 456   V | 81% | 100% | 100% |
| L | 19% | 0% | 0% |
| 459   Q | 100% | 81% | 100% |
| R | 0% | 19% | 0% |
| 472   A | 81% | 81% | 100% |
| T | 19% | 19% | 0% |
| 473   S | 81% | 81% | 100% |
| N | 19% | 19% | 0% |
| 495   E | 100% | 97% | 100% |
| G | 0% | 3% | 0% |
| 498   N | 81% | 100% | 100% |
| S | 19% | 0% | 0% |

TABLE 3

| NSI amino acid sequence variation | | | |
|---|---|---|---|
| Sequence source # NSI sequences analysed | H1N1 reassortant 16 | H3N2 reassortant 31 | RG 11 |
| Position   Amino acid | Frequency | | |
| 3   P | 94% | 87% | 100% |
| S | 6% | 13% | 0% |
| 6   V | 94% | 100% | 100% |
| M | 6% | 0% | 0% |
| 18   V | 94% | 87% | 100% |
| I | 6% | 13% | 0% |
| 21   R | 100% | 87% | 100% |
| Q | 0% | 13% | 0% |
| 22   V | 94% | 100% | 100% |
| F | 6% | 0% | 0% |
| 23   A | 100% | 87% | 64% |
| V | 0% | 13% | 36% |
| 25   Q | 94% | 100% | 100% |
| N | 6% | 0% | 0% |
| 26   E | 94% | 100% | 100% |
| G | 6% | 0% | 0% |
| 28   G | 100% | 87% | 100% |
| S | 0% | 13% | 0% |
| 41   K | 100% | 87% | 100% |
| R | 0% | 13% | 0% |
| 44   R | 94% | 100% | 100% |
| K | 6% | 0% | 0% |
| 48   S | 94% | 87% | 100% |
| N | 6% | 13% | 0% |
| 55   K | 31% | 58% | 45% |
| E | 69% | 42% | 45% |
| 56   T | 100% | 87% | 100% |
| A | 0% | 13% | 0% |
| 59   R | 94% | 87% | 100% |
| H | 6% | 13% | 0% |
| 60   A | 94% | 87% | 100% |
| V | 6% | 13% | 0% |

TABLE 3-continued

| NSI amino acid sequence variation | | | |
|---|---|---|---|
| Sequence source # NSI sequences analysed | H1N1 reassortant 16 | H3N2 reassortant 31 | RG 11 |
| Position   Amino acid | Frequency | | |
| 67   R | 94% | 87% | 100% |
| K | 0% | 13% | 0% |
| W | 6% | 0% | 0% |
| 74   D | 94% | 100% | 100% |
| S | 6% | 0% | 0% |
| 76   A | 94% | 100% | 100% |
| T | 6% | 0% | 0% |
| 77   L | 100% | 97% | 100% |
| F | 0% | 3% | 0% |
| 78   K | 94% | 100% | 100% |
| R | 6% | 0% | 0% |
| 81   M | 94% | 100% | 100% |
| I | 6% | 0% | 0% |
| 82   A | 100% | 87% | 100% |
| V | 0% | 13% | 0% |
| 84   V | 100% | 87% | 100% |
| T | 0% | 13% | 0% |
| 86   A | 94% | 100% | 100% |
| T | 6% | 0% | 0% |
| 87   S | 100% | 97% | 100% |
| L | 0% | 3% | 0% |
| 90   L | 81% | 87% | 100% |
| I | 19% | 13% | 0% |
| 91   T | 94% | 100% | 100% |
| S | 6% | 0% | 0% |
| 95   L | 100% | 87% | 100% |
| I | 0% | 13% | 0% |
| 98   M | 100% | 87% | 100% |
| L | 0% | 13% | 0% |
| 101   D | 100% | 87% | 55% |
| N | 0% | 13% | 45% |
| 103   S | 94% | 87% | 100% |
| F | 6% | 10% | 0% |
| L | 0% | 3% | 0% |
| 104   M | 94% | 100% | 100% |
| I | 6% | 0% | 0% |
| 106   I | 94% | 87% | 100% |
| M | 6% | 13% | 0% |
| 108   K | 94% | 100% | 100% |
| R | 6% | 0% | 0% |
| 111   V | 94% | 100% | 100% |
| I | 6% | 0% | 0% |
| 112   A | 94% | 87% | 100% |
| E | 6% | 13% | 0% |
| 113   G | 94% | 100% | 100% |
| A | 6% | 0% | 0% |
| 120   D | 94% | 100% | 100% |
| G | 6% | 0% | 0% |
| 123   I | 94% | 97% | 100% |
| V | 6% | 3% | 0% |
| 125   D | 94% | 87% | 100% |
| E | 6% | 13% | 0% |
| 129   I | 94% | 87% | 100% |
| M | 0 | 13% | 0% |
| V | 6% | 0% | 0% |
| 132   A | 94% | 100% | 100% |
| T | 6% | 0% | 0% |
| 139   D | 94% | 100% | 100% |
| N | 6% | 0% | 0% |
| 142   E | 100% | 97% | 100% |
| G | 0% | 3% | 0% |
| 144   L | 100% | 87% | 100% |
| I | 0% | 13% | 0% |
| 145   I | 100% | 87% | 100% |
| V | 0% | 13% | 0% |
| 166   L | 100% | 87% | 100% |
| F | 0% | 13% | 0% |
| 171   A | 94% | 87% | 100% |
| I | 0 | 13% | 0% |
| Y | 6% | 0% | 0% |
| 178   V | 100% | 87% | 100% |
| I | 0% | 13% | 0% |

TABLE 3-continued

| NSI amino acid sequence variation | | | |
|---|---|---|---|
| Sequence source # NSI sequences analysed | H1N1 reassortant 16 | H3N2 reassortant 31 | RG 11 |
| Position | Amino acid | Frequency | |

| Position | Amino acid | | | |
|---|---|---|---|---|
| 189 | D | 94% | 100% | 100% |
| | G | 6% | 0% | 0% |
| 196 | E | 100% | 87% | 100% |
| | K | 0% | 13% | 0% |
| 197 | T | 94% | 87% | 100% |
| | N | 6% | 13% | 0% |
| 198 | L | 94% | 100% | 100% |
| | I | 6% | 0% | 0% |
| 205 | S | 94% | 100% | 100% |
| | N | 6% | 0% | 0% |
| 206 | S | 94% | 100% | 100% |
| | C | 6% | 0% | 0% |
| 207 | N | 94% | 100% | 100% |
| | D | 6% | 0% | 0% |
| 211 | R | 100% | 87% | 100% |
| | G | 0% | 13% | 0% |
| 213 | P | 94% | 100% | 100% |
| | S | 6% | 0% | 0% |
| 215 | T | 94% | 100% | 100% |
| | P | 6% | 0% | 0% |
| 217 | K | 94% | 100% | 100% |
| | E | 6% | 0% | 0% |
| 221 | E | 94% | 94% | 100% |
| | K | 0% | 6% | 0% |
| | — | 6% | 0% | 0% |
| 224 | G | 94% | 87% | 100% |
| | R | 0% | 13% | 0% |
| | — | 6% | 0% | 0% |
| 226 | I | 94% | 87% | 100% |
| | A | 0% | 13% | 0% |
| | — | 6% | 0% | 0% |
| 229 | E | 94% | 87% | 100% |
| | K | 0% | 13% | 0% |
| | — | 6% | 0% | 0% |

TABLE 4

| PA amino acid sequence variation | | | |
|---|---|---|---|
| Sequence source # PA sequences analysed | H1N1 reassortant 16 | H3N2 reassortant 32 | RG 10 |
| Position | Amino acid | Frequency | |

| Position | Amino acid | | | |
|---|---|---|---|---|
| 20 | T | 75% | 78% | 100% |
| | A | 25% | 22% | 0% |
| 28 | L | 75% | 100% | 100% |
| | P | 25% | 0% | 0% |
| 55 | N | 75% | 100% | 100% |
| | D | 25% | 0% | 0% |
| 57 | Q | 75% | 100% | 100% |
| | R | 25% | 0% | 0% |
| 62 | I | 100% | 78% | 100% |
| | V | 0% | 22% | 0% |
| 65 | L | 75% | 100% | 100% |
| | S | 25% | 0% | 0% |
| 66 | G | 100% | 78% | 100% |
| | D | 0% | 22% | 0% |
| 85 | T | 75% | 100% | 100% |
| | I | 25% | 0% | 0% |
| 100 | A | 75% | 100% | 100% |
| | V | 25% | 0% | 0% |
| 101 | E | 100% | 81% | 100% |
| | G | 0% | 19% | 0% |
| 142 | K | 100% | 78% | 100% |
| | N | 0% | 22% | 0% |
| 158 | K | 100% | 100% | 50% |
| | R | 0% | 0% | 50% |
| 184 | S | 100% | 78% | 100% |
| | N | 0% | 22% | 0% |

TABLE 4-continued

| PA amino acid sequence variation | | | |
|---|---|---|---|
| Sequence source # PA sequences analysed | H1N1 reassortant 16 | H3N2 reassortant 32 | RG 10 |
| Position | Amino acid | Frequency | |

| Position | Amino acid | | | |
|---|---|---|---|---|
| 186 | G | 75% | 100% | 100% |
| | S | 25% | 0% | 0% |
| 204 | R | 75% | 78% | 100% |
| | K | 25% | 22% | 0% |
| 208 | T | 100% | 97% | 100% |
| | S | 0% | 3% | 0% |
| 213 | K | 100% | 78% | 100% |
| | R | 0% | 22% | 0% |
| 225 | S | 100% | 78% | 100% |
| | C | 0% | 22% | 0% |
| 228 | N | 100% | 97% | 100% |
| | K | 0% | 3% | 0% |
| 241 | Y | 75% | 78% | 100% |
| | C | 25% | 22% | 0% |
| 249 | M | 100% | 97% | 100% |
| | I | 0% | 3% | 0% |
| 256 | R | 75% | 78% | 100% |
| | K | 25% | 0 | 0% |
| | Q | 0% | 22% | 0% |
| 262 | K | 75% | 100% | 100% |
| | R | 25% | 0% | 0% |
| 268 | L | 100% | 78% | 100% |
| | I | 0% | 22% | 0% |
| 269 | R | 100% | 78% | 100% |
| | K | 0% | 22% | 0% |
| 272 | N | 75% | 100% | 100% |
| | D | 25% | 0% | 0% |
| 275 | P | 75% | 100% | 100% |
| | L | 25% | 0% | 0% |
| 277 | S | 75% | 78% | 100% |
| | H | 25% | 0% | 0% |
| | Y | 0% | 22% | 0% |
| 311 | M | 100% | 81% | 100% |
| | I | 0% | 19% | 0% |
| 312 | R | 75% | 78% | 100% |
| | K | 25% | 22% | 0% |
| 321 | N | 81% | 78% | 100% |
| | K | 19% | 0% | 0% |
| | Y | 0% | 22% | 0% |
| 322 | V | 75% | 78% | 100% |
| | I | 25% | 22% | 0% |
| 323 | V | 100% | 97% | 100% |
| | I | 0% | 3% | 0% |
| 332 | P | 100% | 78% | 100% |
| | S | 0% | 22% | 0% |
| 336 | L | 75% | 100% | 100% |
| | M | 25% | 0% | 0% |
| 337 | S | 75% | 100% | 100% |
| | A | 25% | 0% | 0% |
| 343 | A | 81% | 78% | 100% |
| | T | 19% | 0% | 0% |
| | S | 0% | 22% | 0% |
| 354 | I | 100% | 97% | 100% |
| | V | 0% | 3% | 0% |
| 356 | K | 75% | 78% | 100% |
| | R | 25% | 22% | 0% |
| 362 | K | 75% | 100% | 100% |
| | R | 25% | 0% | 0% |
| 382 | D | 100% | 78% | 100% |
| | E | 0% | 22% | 0% |
| 383 | D | 100% | 78% | 100% |
| | N | 0% | 22% | 0% |
| 385 | K | 100% | 78% | 100% |
| | R | 0% | 22% | 0% |
| 387 | V | 100% | 78% | 100% |
| | I | 0% | 22% | 0% |
| 388 | G | 100% | 78% | 100% |
| | S | 0% | 22% | 0% |
| 394 | D | 81% | 100% | 100% |
| | N | 19% | 0% | 0% |
| 395 | S | 94% | 100% | 100% |
| | N | 6% | 0% | 0% |

TABLE 4-continued

PA amino acid sequence variation

| Sequence source<br># PA sequences analysed | | H1N1 reassortant<br>16 | H3N2 reassortant<br>32 | RG<br>10 |
|---|---|---|---|---|
| Position | Amino acid | Frequency | | |
| 397 | E | 94% | 100% | 100% |
|  | K | 6% | 0% | 0% |
| 400 | L | 75% | 100% | 100% |
|  | P | 25% | 0% | 0% |
| 404 | A | 100% | 78% | 100% |
|  | S | 0% | 22% | 0% |
| 407 | I | 75% | 100% | 100% |
|  | V | 25% | 0% | 0% |
| 421 | S | 100% | 78% | 100% |
|  | V | 0% | 19% | 0% |
|  | I | 0% | 3% | 0% |
| 437 | H | 100% | 97% | 100% |
|  | Y | 0% | 3% | 0% |
| 448 | S | 75% | 78% | 100% |
|  | A | 25% | 22% | 0% |
| 472 | A | 100% | 97% | 100% |
|  | T | 0% | 3% | 0% |
| 538 | E | 94% | 100% | 100% |
|  | G | 6% | 0% | 0% |
| 550 | I | 75% | 78% | 50% |
|  | L | 25% | 22% | 50% |
| 552 | S | 75% | 100% | 100% |
|  | T | 25% | 0% | 0% |
| 556 | Q | 94% | 100% | 100% |
|  | L | 6% | 0% | 0% |
| 557 | V | 100% | 78% | 100% |
|  | I | 0% | 22% | 0% |
| 558 | S | 81% | 100% | 100% |
|  | L | 19% | 0% | 0% |
| 573 | I | 100% | 78% | 100% |
|  | V | 0% | 22% | 0% |
| 613 | E | 94% | 100% | 100% |
|  | K | 6% | 0% | 0% |
| 614 | N | 94% | 100% | 100% |
|  | T | 6% | 0% | 0% |
| 618 | T | 100% | 78% | 100% |
|  | A | 0% | 22% | 0% |
| 626 | K | 75% | 97% | 100% |
|  | R | 25% | 3% | 0% |
| 631 | S | 75% | 78% | 100% |
|  | G | 25% | 22% | 0% |
| 668 | I | 100% | 78% | 100% |
|  | V | 0% | 22% | 0% |
| 683 | L | 81% | 100% | 100% |
|  | I | 19% | 0% | 0% |
| 716 | S | 75% | 78% | 100% |
|  | K | 25% | 22% | 0% |

TABLE 5

PB2 amino acid sequence variation

| Sequence source<br># PB2 sequences analysed | | H1N1 reassortant<br>16 | H3N2 reassortant<br>32 | RG<br>10 |
|---|---|---|---|---|
| Position | Amino acid | Frequency | | |
| 8 | R | 100% | 97% | ND |
|  | Q | 0% | 3% | ND |
| 44 | A | 100% | 75% | 100% |
|  | S | 0% | 25% | 0% |
| 63 | I | 100% | 97% | 100% |
|  | V | 0% | 3% | 0% |
| 67 | I | 100% | 78% | 100% |
|  | V | 0% | 22% | 0% |
| 82 | N | 100% | 75% | 100% |
|  | S | 0% | 25% | 0% |
| 105 | I | 100% | 75% | 50% |
|  | V | 0% | 25% | 0% |
|  | M | 0% | 0% | 50% |

TABLE 5-continued

PB2 amino acid sequence variation

| Sequence source<br># PB2 sequences analysed | | H1N1 reassortant<br>16 | H3N2 reassortant<br>32 | RG<br>10 |
|---|---|---|---|---|
| Position | Amino acid | Frequency | | |
| 107 | N | 100% | 75% | 100% |
|  | S | 0% | 25% | 0% |
| 112 | P | 100% | 94% | 100% |
|  | S | 0% | 6% | 0% |
| 114 | I | 100% | 75% | 100% |
|  | V | 0% | 25% | 0% |
| 120 | E | 100% | 75% | 100% |
|  | D | 0% | 25% | 0% |
| 121 | R | 100% | 75% | 100% |
|  | K | 0% | 25% | 0% |
| 136 | R | 100% | 97% | 100% |
|  | G | 0% | 3% | 0% |
| 194 | Q | 100% | 75% | 100% |
|  | R | 0% | 25% | 0% |
| 221 | A | 100% | 97% | 100% |
|  | S | 0% | 3% | 0% |
| 227 | V | 100% | 75% | 100% |
|  | I | 0% | 25% | 0% |
| 249 | E | 100% | 84% | 100% |
|  | G | 0% | 16% | 0% |
| 251 | R | 100% | 100% | 50% |
|  | K | 0% | 0% | 50% |
| 292 | I | 100% | 75% | 100% |
|  | T | 0% | 25% | 0% |
| 293 | R | 100% | 97% | 100% |
|  | K | 0% | 3% | 0% |
| 299 | R | 100% | 97% | 50% |
|  | K | 0% | 3% | 50% |
| 340 | R | 100% | 75% | 100% |
|  | K | 0% | 25% | 0% |
| 353 | K | 100% | 97% | 100% |
|  | R | 0% | 3% | 0% |
| 360 | Y | 100% | 100% | 50% |
|  | S | 0% | 0% | 50% |
| 368 | R | 100% | 75% | 100% |
|  | K | 0% | 25% | 0% |
| 382 | I | 100% | 75% | 100% |
|  | V | 0% | 25% | 0% |
| 451 | V | 100% | 91% | 100% |
|  | I | 0% | 9% | 0% |
| 453 | P | 100% | 75% | 100% |
|  | H | 0% | 25% | 0% |
| 456 | N | 100% | 75% | 100% |
|  | S | 0% | 25% | 0% |
| 461 | I | 100% | 88% | 100% |
|  | V | 0% | 13% | 0% |
| 463 | I | 100% | 75% | 100% |
|  | V | 0% | 25% | 0% |
| 471 | I | 100% | 75% | 100% |
|  | T | 0% | 25% | 0% |
| 478 | V | 100% | 75% | 100% |
|  | I | 0% | 25% | 0% |
| 480 | I | 100% | 75% | 100% |
|  | V | 0% | 25% | 0% |
| 490 | S | 100% | 97% | 100% |
|  | N | 0% | 3% | 0% |
| 504 | I | 100% | 75% | 50% |
|  | V | 0% | 25% | 50% |
| 526 | K | 100% | 75% | 100% |
|  | R | 0% | 25% | 0% |
| 559 | T | 100% | 75% | 100% |
|  | A | 0% | 25% | 0% |
| 560 | V | 100% | 97% | 100% |
|  | I | 0% | 3% | 0% |
| 569 | T | 100% | 75% | 100% |
|  | A | 0% | 25% | 0% |
| 590 | G | 100% | 75% | 100% |
|  | S | 0% | 25% | 0% |
| 596 | V | 100% | 97% | 100% |
|  | A | 0% | 3% | 0% |
| 613 | A | 100% | 75% | 100% |
|  | T | 0% | 25% | 0% |

TABLE 5-continued

| PB2 amino acid sequence variation | | | |
|---|---|---|---|
| Sequence source | H1N1 reassortant | H3N2 reassortant | RG |
| # PB2 sequences analysed | 16 | 32 | 10 |
| Position | Amino acid | Frequency | | |

| Position | Amino acid | H1N1 | H3N2 | RG |
|---|---|---|---|---|
| 636 | F | 100% | 75% | 100% |
| | L | 0% | 25% | 0% |
| 661 | A | 100% | 75% | 100% |
| | T | 0% | 25% | 0% |
| 667 | V | 100% | 75% | 100% |
| | I | 0% | 25% | 0% |
| 676 | T | 100% | 75% | 100% |
| | I | 0% | 25% | 0% |
| 682 | G | 100% | 75% | 100% |
| | S | 0% | 25% | 0% |
| 684 | A | 100% | 75% | 100% |
| | S | 0% | 25% | 0% |
| 697 | L | 100% | 75% | 100% |
| | I | 0% | 25% | 0% |
| 702 | K | 100% | 75% | 50% |
| | R | 0% | 25% | 50% |
| 706 | P | 94% | 100% | 100% |
| | L | 6% | 0% | 0% |
| 722 | A | 100% | 97% | 100% |
| | T | 0% | 3% | 0% |

These data illustrate the sequence variability in backbone gene segments that are delivered to a culture host when the culture host is contacted with a parent influenza virus strain where quasi-species are present. These data also illustrate the lack of sequence variability in viruses where the backbone segments were originally delivered on expression constructs such as plasmid that are used in reverse genetics techniques.

The sequence diversity that is present in viruses that are produced by classical reassortment and reverse genetics was also analysed by assessing the number of mutations present in the sequenced backbone genes. These analyses are presented in Tables 6-10 and illustrate the increased backbone gene sequence diversity in in viruses that are produced by delivering influenza gene segments to a culture host through infection with a population of influenza virions (e.g. in classical reassortment). A similarly enhanced degree of sequence variation, relative to that in RG reassortants, can be expected to occur in the backbone gene segments of a parent influenza virus strain when used in a hybrid reassortant method of the invention

TABLE 6

| M1 Sequence analysis | | | |
|---|---|---|---|
| | | | Sequence diversity |
| Source | # Sequences | # mutations | Variation across M1 protein (252 AA) |
| H1N1 reassortants | 16 | 13 | 5.2% |
| H3N2 reassortants | 32 | 0 | 0.0% |
| Sequenced RG | 10 | 1 | 0.4% |

TABLE 7

| NP Sequence analysis | | | |
|---|---|---|---|
| | | | Sequence diversity |
| Source | # Sequences | # mutations | Variation across NP protein (498 AA) |
| H1N1 reassortants | 16 | 44 | 8.8% |
| H3N2 reassortants | 32 | 43 | 8.6% |
| Sequenced RG | 11 | 3 | 0.6% |

TABLE 8

| NSI Sequence analysis | | | |
|---|---|---|---|
| | | | Sequence diversity |
| Source | # Sequences | # mutations | Variation across NSI protein (230 AA) |
| H1N1 reassortants | 16 | 54 | 23.5% |
| H3N2 reassortants | 31 | 36 | 15.7% |
| Sequenced RG | 11 | 4 | 1.7% |

TABLE 9

| PA Sequence analysis | | | |
|---|---|---|---|
| | | | Sequence diversity |
| Source | # Sequences | # mutations | Variation across PA protein (716 AA) |
| H1N1 reassortants | 16 | 34 | 4.7% |
| H3N2 reassortants | 32 | 37 | 5.2% |
| Sequenced RG | 10 | 1 | 0.1% |

TABLE 10

| PB2 Sequence analysis | | | |
|---|---|---|---|
| | | | Sequence diversity |
| Source | # Sequences | # mutations | Variation across PB2 protein (759 AA) |
| H1N1 reassortants | 16 | 1 | 0.1% |
| H3N2 reassortants | 32 | 40 | 5.3% |
| Sequenced RG | 10 | 6 | 0.8% |

SEQUENCES

```
SEQ ID NO: 1 (PA, PR8-X)
AGCGAAAGCAGGTACTGATCCAAAATGGAAGATTTTGTGCGACAATGCTTCAATCCGATGATTGTCGAGCTTGCGGAAAA
AACAATGAAAGAGTATGGGGAGGACCTGAAAATCGAAACAAACAAATTTGCAGCAATATGCACTCACTTGGAAGTATGCT
TCATGTATTCAGATTTTCACTTCATCAATGAGCAAGGCGAGTCAATAATCGTAGAACTTGGTGATCCAAATGCACTTTTG
AAGCACAGATTTGAAATAATCGAGGGAAGAGATCGCACAATGGCCTGGACAGTAGTAAACAGTATTTGCAACACTACAGG
```

| SEQUENCES |
| --- |

GGCTGAGAAACCAAAGTTTCTACCAGATTTGTATGATTACAAGGAGAATAGATTTATCGAAATTGGAGTAACAAGGAGAG
AAGTTCACATATACTATCTGGAAAAGGCCAATAAAATTAAATCTGAGAAAACACACATCCACATTTTCTCGTTCACTGGG
GAAGAAATGGCCACAAAGGCAGACTACACTCTCGATGAAGAAAGCAGGGCTAGGATCAAAACCAGACTATTCACCATAAG
ACAAGAAATGGCCAGCAGAGGCCTCTGGGATTCCTTTCGTCAGTCCGAGAGAGGAGAAGAGACAATTGAAGAAAGGTTTG
AAATCACAGGAACAATGCGCAAGCTTGCCGACCAAAGTCTCCCGCCGAACTTCTCCAGCCTTGAAAATTTTAGAGCCTAT
GTGGATGGATTCGAACCGAACGGCTACATTGAGGGCAAGCTGTCTCAAATGTCCAAAGAAGTAAATGCTAGAATTGAACC
TTTTTTGAAAACAACACCACGACCACTTAGACTTCCGAATGGGCCTCCCTGTTCTCAGCGGTCCAAATTCCTGCTGATGG
ATGCCTTAAAATTAAGCATTGAGGACCCAAGTCATGAAGGAGAGGGAATACCGCTATATGATGCAATCAAATGCATGAGA
ACATTCTTTGGATGGAAGGAACCCAATGTTGTTAAACCACACGAAAAGGGAATAAATCCAAATTATCTTCTGTCATGGAA
GCAAGTACTGGCAGAACTGCAGGACATTGAGAATGAGGAGAAAATTCCAAAGACTAAAAATATGAAGAAAACAAGTCAGC
TAAAGTGGGCACTTGGTGAGAACATGGCACCAGAAAAGGTAGACTTTGACGACTGTAAAGATGTAGGTGATTTGAAGCAA
TATGATAGTGATGAACCAGAATTGAGGTCGCTTGCAAGTTGGATTCAGAATGAGTTTAACAAGGCATGCGAACTGACAGA
TTCAAGCTGGATAGAGCTCGATGAGATTGGAGAAGATGTGGCTCCAATTGAACACATTGCAAGCATGAGAAGGAATTATT
TCACATCAGAGGTGTCTCACTGCAGAGCCACAGAATACATAATGAAGGGGGTGTACATCAATACTGCCTTGCTTAATGCA
TCTTGTGCAGCAATGGATGATTTCCAATTAATTCCAATGATAAGCAAGTGTAGAACTAAGGAGGGAAGGCGAAAGACCAA
CTTGTATGGTTTCATCATAAAAGGAAGATCCCACTTAAGGAATGACCACCGACGTGGTAAACTTTGTGAGCATGGAGTTTT
CTCTCACTGACCCAAGACTTGAACCACATAAATGGGAGAAGTACTGTGTTCTTGAGATAGGAGATATGCTTATAAGAAGT
GCCATAGGCCAGGTTTCAAGGCCCATGTTCTTGTATGTGAGAACAAATGGAACCTCAAAAATTAAAATGAAATGGGGAAT
GGAGATGAGGCGTTGCCTCCTCCAGTCACTTCAACAAATTGAGAGTATGATTGAAGCTGAGTCCTCTGTCAAAGAGAAAG
ACATGACCAAAGAGTTCTTTGAGAACAAATCAGAAACATGGCCCATTGGAGAGTTCCCCCAAAGGAGTGGGAGGAAAGTTCC
ATTGGGAAGGTCTGCAGGACTTTATTAGCAAAGTCGGTATTCAACAGCTTGTATGCATCTCCACAACTAGAAGGATTTTC
AGCTGAATCAAGAAAACTGCTTCTTATCGTTCAGGCTCTTAGGGACAACCTTGAACCTGGGACCTTTGATCTTGGGGGGC
TATATGAAGCAATTGAGGAGTGCCTGATTAATGATCCCTGGGTTTTGCTTAATGCTTCTTGGTTCAACTCCTTCCTTACA
CATGCATTGAGTTAGTTGTGGCAGTGCTACTATTTGCTATCCATACTGTCCAAAAAGTACCTTGTTTCTACT

SEQ ID NO: 2 (PB1, PR8-X)
AGCGAAAGCAGGCAAACCATTTGAATGGATGTCAATCCGACCTTACTTTTCTTAAAAGTGCCAACACAAAATGCTATAAG
CACAACTTTCCCTTATACTGGAGACCCTCCTTACAGCCATGGACAGGCAGGAACAGGATACACCATGGATACTGTCAACAGGA
CACATCAGTACTCAGAAAAGGGGAAGATGGACAACAAACACCGAAACTGGAGCACCGCAACTCAACCCGATTGATGGGCCA
CTGCCAGAAGACAATGAACCAAGTGGTTATGCCCAAACAGATTGTGTATTGGAGGCGATGGCTTTCCTTGAGGAATCCCA
TCCTGGTATTTTTGAAAACTCGTGTATTGAAACGATGGAGGTTGTTCAGCAAACACGAGTAGACAAGCTGACACAAGGCC
GACAGACCTATGACTGGACTCTAAATAGAAACCAACCTGCTGCAACAGCATTGGCCAACACAATAGAAGTGTTCAGATCA
AATGGCCTCACGGCCAATGAGTCTGGAAGGCTCATAGACTTCCTTAAGGATGTAATGGAGTCAATGAACAAAGAAGAAAT
GGGGATCACAACTCATTTTCAGAGAAAGAGACGGGTGAGAGACAATATGACTAAGAAATGATAACACAGAGAACAATGG
GTAAAAAGAAGCAGAGATTGAACAAAAGGAGTTATCTAATTAGAGCATTGACCCTGAACACAATGACCAAAGATGCTGAG
AGAGGGAAGCTAAAACGGAGAGCAATTGCAACCCCAGGGATGCAAATAAGGGGGTTTGTATACTTTGTTGAGACACTGGC
AAGGAGTATATGTGAGAAACTTGAACAATCAGGGTTGCCAGTTGGAGGCAATGAGAAGAAAGCAAAGTTGGCAAATGTTG
TAAGGAAGATGATGACCAATTCTCAGGACACCGAACTTTCTTTCACCATCACTGGAGATAACACCAAATGGAACGAAAAT
CAGAATCCTCGGATGTTTTTGGCCATGATCACATATATGACCAGAAATCAGCCCGAATGGTTCAGAAATGTTCTAAGTAT
TGCTCCAATAATGTTCTCAAACAAAATGGCGAGACTGGGGAAAAGGGTATATGTTTGAGAGCAAGAGTATGAAACTTAGAA
CTCAAATACCTGCAGAAATGCTAGCAAGCATCGATTTGAAATATTTCAATGATTCAACAAGAAAGAAGATTGAAAAAATC
CGACCGCTCTTAATAGAGGGGACTGCATCATTGAGCCCTGGAATGATGATGGGCATGTTCAATATGTTAAGCACTGTATT
AGGCGTCTCCATCCTGAATCTTGGACAAAAGAGATACACCAAGACTACTTACTGGTGGGATGGTCTTCAATCCTCTGACG
ATTTTGCTCTGATTGTGAATGCACCCAATCATGAAGGGGATTCAAGCCGGAGTCGACAGGTTTTATCGAACCTGTAAGCTA
CTTGGAATCAATATGAGCAAGAAAAGTCTTACATAAACAGAACAGGTACATTTGAATTCACAAGTTTTTTTCTATCGTTA
TGGGTTTGTTGCCAATTTCAGCATGGAGCTTCCCAGTTTTGGGGTGTCTGGGATCAACGAGTCAGCGGACATGAGTATTG
GAGTTACTGTCATCAAAAACAATATGATAAACAATGATCTTGGTCCAGCAACAGCTCAAATGGCCCTTCAGTTGTTCATC
AAAGATTACAGGTACACGTACCGATGCCATAGAGGTGACACACAAATACAAACCCGAAGATCATTTGAAATAAAGAAACT
GTGGGAGCAAACCCGTTCCAAAGCTGGACTGCTGGTCTCCGACGGAGGCCCAAATTTATCAACATTAGAAATCTCCACA
TTCCTGAAGTCTGCCTAAAATGGGAATTGATGATGAGGATTACCAGGGGCGTTTATGCAACCCACTGAACCCATTTGTC
AGCCATAAAGAAATTGAATCAATGAACAATGCAGTGATGATGCCAGCACATGGTCCAGCCAAAAACATGGAGTATGATGC
TGTTGCAACAACACACTCCTGGATCCCCAAAAGAAATCGATCCATCTTGAATACAAGTCAAAGAGGAGTACTTGAGGATG
AACAAATGTACCAAAGGTGCTGCAATTTATTTGAAAAATTCTTCCCCAGCAGTTCATACAGAAGACACGTCGGGATATCC
AGTATGGTGGAGGCTATGGTTTCCAGAGCCCGAATTGATGCACGGATTGATTTCGAATCTGGAAGGATAAAGAAAGAAGA
GTTCACTGAGATCATGAAGATCTGTTCCACCATTGAAGAGCTCAGACGGCAAAAATAGTGAATTTAGCTTGTCCTTCATG
AAAAAAATGCCTTGTTTCTACT

SEQ ID NO: 3 (PB2, PR8-X)
AGCGAAAGCAGGTCAATTATATTCAATATGGAAAGAATAAAAGAACTAAGAAATCTAATGTCGCAGTCTCGCACCCGCGA
GATACTCACAAAAACCACCGTGGACCATATGGCCATAATCAAGAAGTACACATCAGGAAGACAGGAGAAGAACCCAGCAC
TTAGGATGAAATGGATGATGGCAATGAAATATCCAATTACAGCAGACAAGAGGATAACGGAAATGATTCCTGAGAGAAAT
GAGCAAGGACAAACTTTATGGAGTAAAATGAATGATGCCGGATCAGACCGAGTGATGGTATCACCTCTGGCTGTGACATG
GTGGAATAGGAATGGACCAATAACAAATACAGTTCATTATCCAAAAATCTACAAAACTTATTTTGAAAGAGTAGAAAGGC
TAAAGCATGGAACCTTTGGCCCTGTCCATTTTAGAAACCAAGTCAAAATACGTCGGAGAGTTGACATAAATCCTGGTCAT
GCAGATCTCAGTGCCAAGGAGGCACAGGATGTAATCATGGAAGTTGTTTTCCCTAACGAAGTGGGAGCCAGGATACTAAC
ATCGGAATCGCAACTAACGATAACCAAAGAGAGAAAGAAGAACTCCAGGATTGCAAAATTTCTCCTTTGATGGTTGCAT
ACATGTTGGAGAGAGAACTGGTCCGCAAAACGAGATTCCTCCCAGTGGCTGGTGGAACAAGCAGTGTGTACATTGAAGTG
TTGCATTTGACTCAAGGAACATGCTGGGAACAGATGTATACTCCAGGAGGGGAAGTGAGGAATGATGATGTTGATCAAAG
CTTGATTATTGCTGCTAGGAACATAGTGAGAAGAGCTGCAGTATCAGCAGATCCACTAGCATCTTTATTGGAGATGTGCC
ACAGCACACAGATTGGTGGAATTAGGATGGTAGACATCCTTAGGCAGAACCCAACAGAAGAGCAAGCCGTGGATATATGC
AAGGCTGCAATGGGACTGAGAATTAGCTCATCCTTCAGTTTTGGTGGATTCACATTTAAGAGAACAAGCGGATCATCAGT
CAAGAGAGAGGAAGAGGTGCTTACGGGCAAATCTTCAAACATTGAAGATAAGAGTGCATGAGGGATATGAAGAGTTCACAA
TGGTTGGGAGAAGAGCAACAGCCATACTCAGAAAAGCAACCAGGAGATTGATTCAGCTGATAGTGAGTGGGAGAGACGAA
CAGTCGATTGCCGAAGCAATAATTGTGGCCATGGTATTTTCACAAGAGGATTGTATGATAAAAGCAGTCAGAGGTGATCT
GAATTTCGTCAATAGGGCGAATCAGCGATTGAATCCTATGCATCAACTTTTAAGACATTTTCAGAAGGATGCGAGAGTGC
TTTTTTCAAAATTGGGGAGTTGAACCTATCGACAATGTGATGGGAATGATTGGGATATTGCCCGACATGACTCCAAGCATC
GAGATGTCAATGAGAGGAGTGAGAATCAGCAAAATGGGTGTAGATGAGTACTCCAGCACGGAGAGGGTAGTGGTGAGCAT

-continued

| SEQUENCES |
|---|

```
TGACCGTTTTTTGAGAATCCGGGACCAACGAGGAAATGTACTACTGTCTCCCGAGGAGGTCAGTGAAACACAGGGAACAG
AGAAACTGACAATAACTTACTCATCGTCAATGATGTGGGAGATTAATGGTCCTGAATCAGTATTGGTCAATACCTATCAA
TGGATCATCAGAAACTGGGAAACTGTTAAAATTCAGTGGTCCCAGAACCCTACAATGCTATACAATAAAATGGAATTTGA
ACCATTTCAGTCTTTAGTACCTAAGGCCATTAGAGGCCAATACAGTGGGTTTGTAAGAACTCTGTTCCAACAAATGAGGG
ATGTGCTTGGGACATTTGATACCGCACAGATAATAAAACTTCTTCCCTTCGCAGCCGCTCCACCAAAGCAAAGTAGAATG
CAGTTCTCCTCATTTACTGTGAATGTGAGGGGATCAGGAATGAGAATACTTGTAAGGGGCAATTCTCCTGTATTCAACTA
TAACAAGGCCACGAAGAGACTCACAGTTCTCGGAAAGGATGCTGGCACTTTAACTGAAGACCCAGATGAAGGCACAGCTG
GAGTGGAGTCCGCTGTTCTGAGGGGATTCCTCATTCTGGGCAAAGAAGACAAGAGATATGGGCCAGCACTAAGCATCAAT
GAACTGAGCAACCTTGCGAAAGGAGAGAAGGCTAATGTGCTAATTGGGCAAGGAGACGTGGTGTTGGTAATGAAACGGAA
ACGGGACTCTAGCATACTTACTGACAGCCAGACAGCGACCAAAAGAATTCGGATGGCCATCAATTAGTGTCGAATAGTTT
AAAAACGACCTTGTTTCTACT

SEQ ID NO: 4 (NP, PR8-X)
AGCAAAAGCAGGGTAGATAATCACTCACTGAGTGACATCAAAATCATGGCGTCTCAAGGCACCAAACGATCTTACGAACA
GATGGAGACTGATGGAGAACGCCAGAATGCCACTGAAATGCAGGCATCCGTCGGAAAAATGATTGGTGGAATTGGACGAT
TCTACATCCAAATGTGCACCGAACTCAAACTCAGTGATTATGAGGGACGGTTGATCCAAAACAGCTTAACAATAGAGAGA
ATGGTGCTCTCTGCTTTTGACGAAAGGAGAAATAAATACCTTGAAGAACATCCCAGTGCGGGAAAAGATCCTAAGAAAAC
TGGAGGACCTATATACAGGAGAGTAAACGGAAGTGGATGAGAGAACTCATCCTTTATGACAAAGAAGAAATAAGGCGAA
TCTGGCGCCAAGCTAATAATGGTGACGATGCAACGGCTGGTCTGACTCACATGATGATCTGGCATTCCAATTTGAATGAT
GCAACTTATCAGAGGACAAGAGCTCTTGTTCGCACCGGAATGGATCCCAGGATGTGCTCTCTGATGCAAGGTTCAACTCT
CCCTAGGAGGTCTGGAGCCGCAGGTGCTGCAGTCAAAGGAGTTGGAACAATGGTGATGGAATTGGTCAGAATGATCAAAC
GTGGGATCAATGATCGGAACTTCTGGAGGGGTGAGAATGGACGAAAAACAAGAATTGCTTATGAAAGAATGTGCAACATT
CTCAAAGGGAAATTTCAAACTGCTGCACAAAAAGCAATGATGGATCAAGTGAGAGAGAGCCGGAACCCAGGGAATGCTGA
GTTCGAAGATCTCACTTTTCTAGCACGGTCTGCACTCATATTGAGAGGGTCCGGTTGCTCACAAGTCCTGCCTGCCTGCCT
GTGTGTATGGACCTGCCGTAGCCAGTGGGTACGACTTTGAAAGGGAGGGATACTCTCTAGTCGGAATAGACCCTTTCAGA
CTGCTTCAAAACAGCCAAGTGTACAGCCTAATCAGACCAAATGAGAATCCAGCACACAAGAGTCAACTGGTGTGGATGGC
ATGCCATTCTGCCGCATTTGAAGATCTAAGAGTATTAAGCTTCATCAAAGGGACGAAGGTGCTCCCAAGAGGGAAGCTTT
CCACTAGAGGAGTTCAAATTGCTTCCAATGAAAATATGGAGACTATGGAAAGTCAAGTACACTTGAACTGAGAAGCAGGTAC
TGGGCCATAAGGACCAGAAGTGGAGGAAACACCAATCAACAGAGGGCATCTGCGGGCCAAATCAGCATACAACCTACGTT
CTCAGTACAGAGAAATCTCCCTTTTGACAGAACAACCATTATGGCAGCATTCAATGGGAATACAGAGGGGGAGAACATCTG
ACATGAGGACCGAAATCATAAGGATGATGGAAAGTGCAAGACCAGAAGATGTGTCTTTCAGGGGGCGGGGAGTCTTCGAG
CTCTCGGACGAAAAGGCAGCGAGCCCGATCGTGCCTTCCTTTGACATGAGTAATGAAGGATCTTATTTCTTCGGAGACAA
TGCAGAGGAGTACGACAATTAAAGAAAAATACCCTTGTTTCTACT

SEQ ID NO: 5 (M, PR8-X)
AGCAAAAGCAGGTAGATATTGAAAGATGAGTCTTCTAACCGAGGTCGAAACGTACGTACTCTCTATCATCCCGTCAGGCC
CCCTCAAAGCCGAGATCGCACAGAGACTTGAAGATGTCTTTGCAGGGAAGAACACCGATCTTGAGGTTCTCATGGAATGG
CTAAAGACAAGACCAATCCTGTCACCTCTGACTAAGGGGGATTTTAGGATTTGTGTTCACGCTCACCGTGCCCAGTGAGCG
AGGACTGCAGCGTAGACGCTTTGTCCAAAATGCCCTTAATGGGAACGGGGATCCAAATAACATGGACAAAGCAGTTAAAC
TGTATAGGAAGCTCAAGAGGGAGATAACATTCCATGGGGCCAAAGAAATCTCACTCAGTTATTCTGCTGGTGCACTTGCC
AGTTGTATGGGCCTCATATACAACAGGATGGGGGTGCTGTGACCACTGAAGTGGCATTTGGCCTGGTATGTGCAACCTGTGA
ACAGATTGCTGACTCCCAGCATCGGTCTCATAGGCAAATGGTGACAACAACCAATCCACTAATCAGACATGAGAACAGAA
TGGTTTTAGCCAGCACTACAGCTAAGGCTATGGAGCAAATGGCTGGATCGAGTGAGCAAGCAGCAGAGGCCATGGAGGTT
GCTAGTCAGGCTAGACAAATGGTGCAAGCGATGAGAACCATTGGGACTCATCCTAGCTCCAGTGCTGGTCTGAAAAATGA
TCTTCTTGAAAATTTGCAGGCCTATCAGAAACGAATGGGGGTGCAGATGGCAACGGTTCAAGTGATCCTCTCACTATTGCC
GCAAATATCATTGGGATCTTGCACTTGACATTGTGGATTCTTGATCGTCTTTTTTTTCAAATGCATTTACCGTCGCTTTAA
ATACGGACTGAAAGGAGGGCCTTCTACGAAGGAGTGCCAAAGTCTATGAGGGAAGAATATCGAAAGGAACAGCAGAGTG
CTGTGGATGCTGACGATGGTCATTTTGTCAGCATAGAGCTGGAGTAAAAAACTACCTTGTTTCTACT

SEQ ID NO: 6 (NS, PR8-X)
AGCAAAAGCAGGGTGACAAAAACATAATGGATCCAAACACTGTGTCAAGCTTTCAGGTAGATTGCTTTCTTTGGCATGTC
CGCAAACGAGTTGCAGACCAAGAACTAGGTGATGCCCCATTCCTTGATCGGCTTCGCCGAGATCAGAAATCCCTAAGAGG
AAGGGGCAGTACTCTCGGTCTGGACATCAAGACAGCCCACACGTGCTGGAAAGCAGATAGTGGAGCGGATTCTGAAAGAAG
AATCCGATGAGGCACTTAAAATGACCATGGCCTCTGTACCTGCGTCGCGTTACCTAACTGACATGACTCTTGAGGGAAATG
TCAAGGGACTGGTCCATGCTCATACCCAAGCAGAAAGTGGCAGGCCCTCTTTGTATCAGAATGGACCAGGCGATCATGGA
TAAGAACATCATACTGAAAGCGAACTTCAGTGTGATTTTTGACCGGCTGGAGACTCTAATATTGCTAAGGGCTTTCACCG
AAGAGGGAGCAATTGTTGGCGAAATTTCACCATTGCCTTCTCTTCCAGGACATACTGCTGAGGATGTCAAAAATGCAGTT
GGGAGTCCTCATCGGAGGACTTGAATGGAATGATAACACAGTTCGAGTCTCTGAAAACTCTACAGAGATTCGCTTGGAGAAG
CAGTAATGAGAATGGGAGACCTCCACTCACTCCAAAACAGAAACGAGAAATGGCGGGAACAATTAGGTCAGAAGTTTGAA
GAAATAAGATGGTTGATTGAAGAAGTGAGACACAAACTGAAGATAACAGAGAATAGTTTTGAGCAAATAACATTTATGCA
AGCCTTACATCTATTGCTTGAAGTGGAGCAAGAGATAAGAACTTTCTCGTTTCAGCTTATTTAGTACTAAAAAACACCCT
TGTTTCTACT

SEQ ID NO: 7 (HA, PR8-X)
AGCAAAAGCAGGGGAAAATAAAAACAACCAAAATGAAGGCAAACCTACTGGTCCTGTTATGTGCACTTGCAGCTGCAGAT
GCAGACACAATATGTATAGGCTACCATACGAACAATTCAACCGACATGTTGACACTGTTACACGACTACTCGAGAAGAATGTGACAGT
GACACACTCTGTTAACCTGCTCGAAGACAGCCACAACGGAAAACTATGTAGATTAAAAGGAATAGCCCCACTACAATTGG
GGAAATGTAACATCGCCGGATGGCTCTTGGGAAACCCAGAATGCGACCCACTGCTTCCAGTGAGATCATGGTCCTACATT
GTAGAAACACCAAACTCTGAGAATGGAATATGTTATCCAGGAGATTTCATCGACTATGAGGAGCTGAGGGAGCAATTGAG
CTCAGTGTCATCATTCGAAAGATTCGAAATATTTCCCAAAGAAAGCTCATGGCCCAACCACAACACAAACGGAGTAACGG
CAGCATGCTCCCATGAGGGGAAAGCAGTTTTTACAGAAATTTGCTATGGCTGACGGAGAAGGAGGGCTCATACCCAAAG
CTGAAAAATTCTTTATGTGAACAAAAAAGGGAAAGAAGTCCTTGTACTGTGGGGTATTCATCACCCGCCTAACAGTAAGGA
ACAACAGAATCTCTATCAGAATGAAAATGCTTATGTCTCTGTAGTGACTTCAAATTATAACAGGAGATTTACCCCGGAAA
TAGCAGAAGACCCAAAGTAAGAGATCAAGCTGGGAGGATGAACTATTACTGGACCTTGCTAAAACCCGGAGACACAATA
ATATTTGAGGCAAATGGAAATCTAATAGCACCAATGTATGCTTTCGCACTGAGTAGAGGCTTTGGGTCCGGCATCATCAC
CTCAAACGCATCAATGCATGAGTGTAACACGAAGTGTCAAACACCCCTGGGAGCTATAAACAGCAGTCTCCCTTACCAGA
ATATACACCCAGTCACAATAGGAGAGTGCCCAAAATACGTCAGGAGTGCCAAATTGAGGATGGTTACAGGACTAAGGAAC
```

| SEQUENCES |
| --- |

ATTCCGTCCATTCAATCCAGAGGTCTATTTGGAGCCATTGCCGGTTTTATTGAAGGGGGATGGACTGGAATGATAGATGG
ATGGTATGGTTATCATCATCAGAATGAACAGGGATCAGGCTATGCAGCGGATCAAAAAAGCACACAAAATGCCATTAACG
GGATTACAAACAAGGTGAACACTGTTATCGAGAAAATGAACATTCAATTCACAGCTGTGGGTAAAGAATTCAACAAATTA
GAAAAAAGGATGGAAAATTTAAATAAAAAAGTTGATGATGGATTTCTGGACATTTGGACATATAATGCAGAATTGTTAGT
TCTACTGGAAAATGAAAGGACTCTGGAATTCCATGACTCAAATGTGAAGAATCTGTATGAGAAAGTAAAAAGCCAATTAA
AGAATAATGCCAAAGAAATCGGAAATGGATGTTTTGAGTTCTACCACAAGTGTGACAATGAATGCATGGAAAGTGTAAGA
AATGGGACTTATGATTATCCCAAATATTCAGAAGAGTCAAAGTTGAACAGGGAAAAGGTAGATGGAGTGAAATTGGAATC
AATGGGGATCTATCAGATTCTGGCGATCTACTCAACTGTCGCCAGTTCACTGGTGCTTTTGGTCTCCCTGGGGGCAATCA
GTTTCTGGATGTGTTCTAATGGATCTTTGCAGTGCAGAATATGCATCTGAGATTAGAATTTCAGAGATATGAGGAAAAAC
ACCCTTGTTTCTACT

SEQ ID NO: 8 (NA, PR8-X)
AGCAAAAGCAGGGGTTTAAAATGAATCCAAATCAGAAAATAATAACCATTGGATCAATCTGTCTGGTAGTCGGACTAATT
AGCCTAATATTGCAAATAGGGAATATAATCTCAATATGGATTAGCCATTCAATTCAAACTGGAAGTCAAAACCATACTGG
AATATGCAACCAAAACATCATTACCTATAAAAATAGCACCTGGGTAAAGGACACAACTTCAGTGATATTAACCGGCAATT
CATCTCTTTGTCCCATCCGTGGGTGGGCTATATACAGCAAAGACAATAGCATAAGAATTGGTTCCAAAGGAGACGTTTTT
GTCATAAGAGAGCCCTTTATTTCATGTTCTCACTTGGAATGCAGGACCTTTTTTCTGACCCAAGGTGCCTTACTGAATGA
CAAGCATTCAAGTGGGACTGTTAAGGACAGAAGCCCTTATAGGGCCTTAATGAGCTGCCCTGTCGGTGAAGCTCCGTCCC
CGTACAATTCAAGATTTGAATCGGTTGCTTGGTCAGCAAGTGCATGTCATGATGGCATGGGCTGGCTAACAATCGGAATT
TCAGGTCCAGATAATGGAGCAGTGGCTGTATTAAAATACAACGGCATAATAACTGAAACCATAAAAAGTTGGAGGAAGAA
AATATTGAGGACACAAGAGTCTGAATGTGCCTGTGTAAATGGTTCATGTTTTACTATAATGACTGATGGCCCGAGTGATG
GGCTGGCCTCGTACAAAATTTTCAAGATCGAAAAGGGGAAGGTTACTAAATCAATAGAGTTGAATGCACCTAATTCTCAC
TATGAGGAATGTTCCTGTTACCCTGATACCGACAAAGTGATGTGTGTGCAGAGACAATTGGCATGGTTCGAACCGGCC
ATGGGTGTCTTTCGATCAAAACCTGGATTATCAAATAGGATACATCTGCAGTGGGGTTTTCGGTGACAACCCGCGTCCCG
AAGATGGAACAGGCAGCTGTGGTCCAGTGTATGTTGATGGAGCAAACGGAGTAAAGGGATTTTCATATAGGTATGGTAAT
GGTGTTTGGATAGGAAGGACCAAAAGTCACAGTTCCAGACATGGGTTTGAGATGATTTGGGATCCTAATGGATGGACAGA
GACTGATAGTAAGTTCTCTGTGAGGCAAGATGTTGTGGCAATGACTGATTGGTCAGGGTATAGCGGAAGTTTCGTTCAAC
ATCCTGAGCTGACAGGGCTAGACTGTATGAGGCCGTGCTTCTGGGTTGAATTAATCAGGGGACGACCTAAAGAAAAAACA
ATCTGGACTAGTGCGAGCAGCATTTCTTTTTGTGGCGTGAATAGTGATACTGTAGATTGGTCTTGGCCAGACGGTGCTGA
GTTGCCATTCAGCATTGACAAGTAGTCTGTTCAAAAAACTCCTTGTTTCTACT

SEQ ID NO: 9 (PA, 105p30)
AGCGAAAGCAGGTACTGATTCGAAATGGAAGATTTTGTGCGACAATGCTTCAATCCGATGATTGTCGAGCTTGCGGAAAA
GGCAATGAAAGAGTATGGAGAGGACCTGAAAATCGAAACAAACAAATTTGCAGCAATATGCACCCACTTGGAAGTATGCT
TCATGTATTCAGATTTTCATTTCATCAATGAGCAAGGCGAATCAATAATAGTAGAGCCTGAGGACCCAAATGCACTTTTA
AAACACAGATTTGAGATAATAGAGGGGCGAGATCGTACAATGGCATGGACAGTTGTAAACAGTATTTGCAACACCACAGG
AGCTGAGAAACCAAAGTTTCTGCCAGATCTGTATGATTACAAAGAGAATAGGTTCATCGAAATTGGAGTGACAAGGAGAG
AAGTTCACATATACTATCTGGAAAAGGCCAACAAAATTAAATCTGAGAAGCACACATATTCACATTTTCTCATTTACTGGC
GAAGAAATGGCCACAAAGGCCGATTACACTCTCGATGAAGAAAGCAGGGCTAGAATTAAAACCAGACTATTCACCATAAG
GCAAGAAATGGCAAGCAGAGGTCTTTGGGACTCCTTTCGTCAGTCCGAAAGAGGCGAAGAGACAATTGAAGAAAGGTTTG
AAATCACAGGGACAATGCGCAGGCTCGCTGATCAAAGCCTTCCGCCGAACTTCTCCTGCATTGAGAATTTTAGAGCCTAT
GTGGATGGATTTGAACCGAACGGCTCCATTGAGGGCAAGCTTTCTCAAATGTCCAAAGAAGTAAATGCTAAAATTGAGCC
TTTTTTTGAAAACAACACCTCGACCAATTAGACTTCCGAATGGGCCTCCTTGTTTTCAGCGGTCAAAATTCCTGCTGATGG
ATTCTTTAAAATTAAGCATTGAGGATCCAAATCATGAAGGGGAGGGAATACCACTATATGATGCAATCAAGTGTATGAGA
ACATTCTTTGGATGGAAAGAACCCACTGTTGTCAAGCCACACGAGAAGGATAAATCCGAATTATCTGCTGTCGTGGAA
GCAGGTGTTGGAAGAGCTGCAGGACATTGAGAGTGAGGAGAAGATTCCAAGAACAAAAAACATGAAAAAAACGAGTCAGT
TAAAGTGGGCACTTGGTGAGAACATGGCACCAGAGAAGGTGGATTTTGATGACTGTAAAGATATAAGCGATTTGAAGCAA
TATGATAGTGACGAACCTGAATTAAGGTCATTTTCAAGTTGGATCCAGAATGAGTTCAACAAGGCATGCGAGCTGACCGA
TTCAATCTGGATAGAGCTCGATGAGATTGGAGAAGATGTGGCCCCGATTGAACACATTGCAAGCATGAGAAGAAATTACT
TCACAGCTGAGGTGTCCCATTGCAGAGCCACTGAATATATAATGAAAGGGGTATACATTAATACTGCTTTGCTTAATGCA
TCCTGTGCAGCAATGGATGATTTCCAACTAATTCCTATGATAAGCAAATGTAGAACTAAAGAGGGAAGGAGAAAGACCAA
TTTGTACGGCTTCATCATAAAAGGAAGATCTCACTTAAGGAATGATACCGATGTGGTAAACTTTGTGAGCATGGAGTTTT
CCCTCACTGACCCAAGACTTGAGCCACACAAATGGGAGAAGTACTGTGTTCTTGAGATAGGAAGATATGCTTCTAAGGAGT
GCAATAGGCCAAGTGTCAAGGCCCATGTTCTTGTATGTAAGAACAAATGGAACCTCAAAAATTAAAATGAAATGGGGAAT
GGGAGATGAGGCGTTGCCTCCTCCAATCCCTCCAACAAATAGAGAGCATGATTGAAGCTGAGTCCTCTGTCAAGGAGAAG
ACATGACAAAAGAGTTTTTTGAGAATAGATCAGAAACATGGCCCATTGGAGAGTCACCAAAAGGAGTGGAAGAAGGTTCC
ATTGGGAAAGTATGCAGGACACTATTGGCTAAATCAGTATTCAATAGTCTGTATGCATCTCCACAATTAGAAGGATTTTC
AGCTGAGTCAAGAAAGTTGCTCCTTATTGTTCAGGCTCTTAGGGACAATCTGGAACCTGGGACCTTTGATCTTGGGGGAC
TATATGAAGCAATTGAGGAGTGCCTGATTAATGATCCCTGGGTTTTGCTTAATGCTTCTTGGTTCAACTCCTTCCTAAAA
CATGCATTGAGATAGCTGAGGCAATGCTACTATTTGTTATCCATACTGTCCAAAAAGTA

SEQ ID NO: 10 (PB1, 105p30)
AGCGAAAGCAGGCAAACCATTTGAATGGATGTCAATCCGACATTACTTTTCTTAAAAGTGCCAGCACAAAATGCTATAAG
CACAACTTTTCCTTATACTGGTGACCCTCCTTACAGCCATGGAACAGGAACAGGATACACCATGGATACAGTCAACAGGA
CACATCAGTACTCAGAAAGAGGAAGATGGACGAAAAATACCGAAACTGGAGCACCGCAACTCAACCCAATTGATGGGCCA
CTACCAGAAGACAATGAACCAAGTGGCTATGCCCAAACAGATTGTGTATTAGAGGCAATGGCTTTCCTTGAAGAATCCCA
TCCTGGTATTTTTGAAAACTCTTGTATTGAAACAATGGAGGTTGTTCAGCAAACAAGGGTGACAAACTGACACAAGGCA
GACAAACCTATGACTGGACTCTAAATAGGAACCAGCCTGCTGCCACAGCATTGGCAAACACCATAGAAGTATTCAGATCA
AATGGCCTCATAGCAAATGAATCTGGAAGGCTAATAGACTTCCTTAAAGATGTAATGGAGTCGATGGACAGAGACGAAGT
AGAGGTCACAACTCATTTTCAAAGAAAGAGGAGAGTGAGAGACAATGTAACTAAAAAAATGGTGACCCAAAGAACAATAG
GAAAAAAGACATAAATTAGACAAAAGAAGTTACCTAATTAGGGCATTAACCCTGAACACAATGACCAAAAGATGCTGAG
AGGGGGAAACTAAAACGCAGAGCAATTGCAACCCCAGGAATGCAAATAAGGGGGTTTGTATACTTTGTTGAGACACTGGC
AAGAAGCATATGTGAAAAGCTTGAACAATCAGGGTTGCCAGTTGGAGGAAATGAGAAGAAAGCAAAGTTAGCAAATGTTG
TAAGGAAGATGATGACCAACTCCCAGGACACTGAAATTTCTTTTACCATCACTGGAGATAACACAAATGGAACGAAAT
CAAAACCCTAGAATGTTCTTGGCCATGATCACATATATAACCAAAGATCAGCCTGAATGGTTCAGAAATATTCTAAGTAT
TGCTCCAATAATGTTTTCAAACAAAATGGCGAGACTAGGTAGGGGGGTATATGTTTGAAAGCAAGAGTATGAAACTGAGAA
CCCAAATACCTGCAGAGATGCTAGCCAACATAGATTTGAAATATTTCAATGATTCAACTAAAAAGAAAATTGAAAAAATT

| SEQUENCES |
| --- |

CGACCATTATTAATAGATGGAACTGCATCATTGAGTCCTGGAATGATGATGGGCATGTTCAATATGTTAAGCACCGTCTT
GGGCGTTTCCATTCTGAATCTTGGGCAAAAAAGATACACCAAGACTACTTACTGGTGGGATGGTCTTCAATCGTCTGATG
ATTTTGCTTTGATTGTGAATGCACCCAATTATGCAGGAATTCAAGCTGGAGTTGACAGGTTTTATCGAACCTGTAAGCTG
CTCGGAATTAATATGAGCAAAAAGAAGTCTTACATAAACAGAACAGGTACCTTTGAATTCACGAGCTTTTTCTATCGTTA
TGGGTTTGTTGCCAATTTCAGCATGGAGCTTCCTAGTTTTGGGGTGTCTGGGGTCAATGAATCTGCAGACATGAGTATTG
GAGTCACTGTCATCAAAAACAATATGATAAACAATGACCTTGGCCCAGCAACTGCTCAAATGGCCCTTCAGTTATTTATA
AAAGATTACAGGTACACTTATCGATGCCACAGAGGTGACACACAAATACAAACCCGGAGATCATTTGAAATAAAGAAACT
ATGGGACCAAACCCGCTCCAAAGCTGGGCTGTTGGTCTCTGATGGAGGCCCCAATTTATATAACATTAGGAATCTACATA
TTCCTGAAGTCTGCTTGAAATGGGAGTTGATGGATGAGGATTACCAGGGGCGTTTATGCAACCCATTGAACCCGTTTGTC
AGCCATAAAGAGATTGAATCAGTGAACAATGCAGTGATAATGCCGGCACATGGTCCAGCCAAAAATATGGAGTATGACGC
TGTTGCAACAACACACTCTTGGGTCCCCAAAAGAAATCGATCCATTTTAAACACGAGCCAAAGAGGGATACTTGAAGATG
AGCAAATGTACCAAAGGTGCTGCAATTTATTTGAAAAATTCTTCCCAAGTAGCTCATACAGAAGACCAGTTGGAATATCC
AGTATGGTAGAGGCTATGGTTTCAAGAGCCCGAATTGATGCACGGATTGATTTCGAATCTGGAAGGATAAAGAAAGAGGA
ATTCGCTGAGATCATGAAGACCTGTTCCACCATTGAAGACCTCAGACGGCAAAAATAGGGAATTTGGCTTGTCCTTCATG
AAAAAATGCCTTGTTTCTACT

SEQ ID NO: 11 (PB2, 105p30)
AGCGAAAGCAGGTCAATTATATTCAATATGGAAAGAATAAAAGAGCTAAGGAATCTGATGTCACAATCTCGCACTCGCGA
GATACTTACCAAAACTACTGTAGACCACATGGCCATAATAAAGAAATACACATCAGGAAGACAGGAGAAAAACCCATCAC
TTAGGATGAAATGGATGATGGCAATGAAATACCCAATTACAGCTGATAAAAGGATAACGGAAATGATTCCTGAAAGAAAT
GAGCAAGGACAGACACTATGGAGTAAAGTGAATGATGCCGGATCAGACCGAGTGATGATATCACCCCTAGCTGTGACATG
GTGGAACAGAAATGGACCAGTGGCAAACACTATCCACTATCCAAAAATCTACAAAACTTACTTTGAAAAGGTTGAAAGGT
TAAAACATGGAACCTTTGGCCCTGTACACTTTAGAAACCAAGTCAAAATACGCCGAAGAGTCGACATAAATCCTGGTCAT
GCAGACCTCAGCGCCAAGGAGGCACAGGATGTAATTATGGAAGTTGTTTTCCCTAATGAAGTGGGAGCCAGAATACTAAC
ATCAGAATCGCAATTAACGATAACTAAGGAGAAAAAGAGGAACTCCAGAATTGCAAAATTTCCCCTTTGATGGTTGCAT
ACATGTTAGAGAGGGAACTTGTCCGCAAAACAAGATTTCTCCCGGTTGCAGGTGGAACAAGCAGTGTGTACATTGAAGTT
TTGCATTTAACACAGGGGACATGCTGGGAGCAGATGTACACTCCAGGTGGGGAGGTGAGGAATGATGATGTTGATCAAAG
CCTAATTATTGCTGCTAGGAACATAGTGAGAAGAGCTGCAGTATCAGCAGATCCACTAGCATCTTTATTAGAAATGTGCC
ATAGCACACAGATTGGTGGAACAAGGATGGTGGATATTCTCAGGCAAAATCCAACGAAGAACAAGCTGTGGACATATGC
AAAGCAGCAATGGGGCTGAGAATCAGTTCATCCTTCAGTTTTGGCGGATTCACATTTAAGAGAACAAGTGGATCGTCAGT
CAAAAGGGAGGAAGAAGTGCTAACGGGCAATCTGCAAACATTGAAGCTAACTGTGCATGAGGGATATGAAGAATTCACAA
TAGTTGGGAAAAAGGCAACAGCTATACTCAGAAAAGCAACCAGGAGATTGATTCAACTAATAGTGAGTGGAAGAGACGAA
CAGTCAATAGTCGAAGCAATAGTTGTAGCAATGGTATTCTCACAAGAAGATTGCATGGTAAAAGCGGTTAGAGGTGATCT
GAATTTCGTTAATAGAGCGAATCAGCGGTTGAATCCCATGCATCAACTTTTGAGACATTTTCAGAAGGATGCTAAAGTAC
TTTTCCTAAATTGGGGAATTGAACATATTGACAATGTGATGGGAATGATTGGGATATTACCTGATATGACTCCAAGTACC
GAGATGTCAATGAGAGGAGTGAGAGTCAGCAAAATGGGTGTAGATGAATACTCCAATGCTGAAAGGGTAGTGGTAAGCAT
TGACCGTTTTTTTGAGGGTCCGGGACCAAAGAGGAAATGTATTACTGTCTCCAGAGGAAGTCAGTGAAACACAAGGAACAG
AGAAACTGACAATAACTTACTCTTCATCATTGATGTGGGAGATTAATGGCCCTGAGTCAGTGTTGATCAATACCTACCAA
TGGATCATCAGAAACTGGGAGACTGTTAAAATTCAGTGGTCTCAGAACCCTACAATGCTATACAATAAAATGGAATTTGA
GCCATTTCAATCTCTAGTCCCCAAGGCCATTAGAGGCCAATACAGTGGGTTTGTTAGAACTCTATTTCAACAAATGAGGG
ATGTGCTCGGGACCTTTGACACAACTCAGATAATAAAACTTCTTCCCTTTGCAGCCGCTCCACCAAAGCAAAGTAGAATG
CAATTCTCGTCATTAACTGTGAATGTGAGGGGATCAGGAATGAGAATACTTGTAAGGGGTAATTCTCCAGTATTCAACTA
CAACAAGACCACTAAGAGACTCACAATCCTCGGAAAGGATGCTGGCACTTTAACTGAAGACCCAGATGAAGGCACAGCTG
GAGTGGAATCTGCTGTTTTTAAGGGGATTCCTCATTCTAGGCAAAGAAGATAGAAGATATGGGCCAGCATTAAGCATCAGT
GAATTGAGCAACCTTGCGAAAGGGGAGAAAGCTAATGTGCTAATTGGGCAAGGGGATGTAGTGTTGGTAATGAAACGAAA
ACGGGACTCTAGCATACTTACTGACAGCCAGACAGCGACCAAAAGAATTCGGATGGCCATCAATTAATTTCGAATAATTT
AAAAACGACCTTGTTTCTACT

SEQ ID NO: 12 (NP, 105p30)
AGCAAAAGCAGGGTAGATAATCACTCACTGAGTGACATCAAAGTCATGGCGTCCCAAGGCACCAAACGGTCTTACGAACA
GATGGAGACTGATGGGGAACGCCAGAATGCAACTGAAATCAGAGCATCCGTCGGAAGAATGATTGGGGGAATTGGGCGAT
TCTACATCCAAATGTGCACCGAGCTTAAGCTCAATGATTATGAGGGACGACTGATCCAGAACAGCTTAACAATAGAGAGA
ATGGTGCTTTCTGCTTTTGATGAGAGGAGAAATAAATATCTGGAAGAACATCCCAGCGCAGGGAAGATCCTAAGAAAAC
TGGAGGACCCATATACAAGAGAGTAGATGGAAGTGGGTGAGGGAAGTTGCACATCGTCCTTTATGACAAAGAAGAAATAAGGCGGA
TTTGGCGCCAAGCCAACAATGGTGATGATGCAACAGCTGGTTTGACTCACATTATGATCTGGCATTCTAATTTGAATGAT
ACAACTTACCAGAGGACAAGAGCTCTTGTCCGCACCGGAATGGATCCCAGGATGTGCTCTTTGATGCAAGGTTCAACTCT
CCCTAGAAGATCTGGAGCAGCAGGCGCTGCAGTCAAAGGAGTTGGGACAATGGTATTGGAGTTAATCAGGATGATCAAAC
GTGGGATCAACGACCGAAACTTCTGGAGGGGTGAGAATGGGAGAAAACAAGGATTGCTTATGAGAGAATGTGCAACATT
CTCAAAGGAAAATTTCAAACAGCTGCACAAAAAGCAATGATGGATCAAGTGAGAGAAAGCCGGAACCCAGGAAATGCTGA
GATCGAAGATCTCACTTTTCTGGCACGGTCTGCACTCATATTGAGAGGATCAGTTGCTCACAAGTCTTGCCTGCCTGCTT
GTGTGTATGGACCAGCCGTAGCCAGTGGGTATGACTTCGAAAAAGAGGGATACTCTTTGGTGGGAGTAGACCCTTTCAAA
CTGCTTCAAACCAGTCAGGTATACAGCCTAATTAGACCAAACGAGAATCCCGCACACAAGAGCCAGTTGGTGTGGATGGC
ATGCAATTCTGCTGCATTTGAAGATCTAAGAGTGTCAAGCTTCATCAGAGGGACAAGAGTACTTCCAAGGGGGAAGCTCT
CCACTAGAGGAGTACAAATTGCTTCAAATGAAAACATGGATGCTATTGTCTCAAGTACTCTTGAACTGAAGACAGATAC
TGGGCCATAAGAACCAGAAGTGGAGGGAACACCAATCAACAAAGGGCCTCTGCGGGCCAAATCAGCACACAACCTACGTT
TTCTGTGCAGAGAAACCTCCCATTTGACAAAACAACCATCATGGCAGCATTCACTGGGAATACAGAGGGAAGAACATCAG
ACATGCGGGCAGAAATCATAAAGATGATGGAAGTGCAAGACCAGAAGAAGTGTCCTTCCAGGGACGGGGAGTCTTTGAG
CTCTCGGACGAAAGGGCAACGAACCCGATCGTGCCCTCCTTTGACATGAGTAATGAAGGATCTTATTTCTTCGGAGACAA
TGCAGAGGAGTACGACAATTAATGAAAAATACCCTTGTTTCTACT

SEQ ID NO: 13 (M, 105p30)
AGCAAAAGCAGGTAGATATTGAAAGATGAGTCTTCTAACCGAGGTCGAAACGTACGTTCTCTCTATCGTCCCATCAGGCC
CCCTCAAAGCCGAGATCGCACAGAGACTTGAAGATGTATTTGCTGGAAAGAATACCGATCTTGAGGCTCTCATGGAATGG
CTAAAGACAAGACCAATCCTGTCACCTCTGACTAAGGGGATTTTAGGATTTGTGTTCACGCTCACCGTGCCCAGTGAGCG
AGGACTGCAGCGTAGACGCTTTGTCCAAAATGCCCTTAATGGGAATGGGGATCCAAATAATATGGACAAGGCTGTCAAAC

-continued

SEQUENCES

```
TGTATCGAAAGCTTAAGAGGGAGATAACATTCCATGGGGCCAAAGAAATAGCACTCAGTTATTCTGCTGGAGCACTTGCC
AGTTGTATGGGACTCATATACAACAGGATGGGGGCTGTGACCACCGAATCAGCATTTGGCCTTATATGTGCAACCTGTGA
ACAGATTGCCGACTCCCAGCATAAGTCTCATAGGCAAATGGTAACAACAACCAATCCATTAATAAGACATGAGAACAGAA
TGGTTCTGGCCAGCACTACAGCTAAGGCTATGGAGCAAATGGCTGGATCGAGTGAACAAGCAGCTGAGGCCATGGAGGTT
GCTAGTCAGGCCAGGCAGATGGTGCAGGCAATGAGAGCCATTGGGACTCATCCTAGCTCTAGCACTGGTCTGAAAAATGA
TCTCCTTGAAAATTTGCAGGCCTATCAGAAACGAATGGGGGTGCAGATGCAACGATTCAAGTGATCCTCTTGTTGTTGCC
GCAAGTATAATTGGGATTGTGCACCTGATATTGTGGATTATTGATCGCCTTTTTTCCAAAAGCATTTATCGTATTTTTAA
ACACGGTTTAAAAAGAGGGCCTTCTACGGAAGGAGTACCGGAGTCTATGAGGGAAGAATATCGAGAGGAACAGCAGAATG
CTGTGGATGCTGACGATGGTCATTTTGTCAGCATAGAGCTAGAGTAAAAAACTACCTTGTTTCTACT

SEQ ID NO: 14 (NS, 105p30)
AGCAAAAGCAGGGTGGCAAAGACATAATGGATTCCCACACTGTGTCAAGCTTTCAGGTAGATTGTTTCCTTTGGCATGTC
CGCAAACAAGTTGCAGACCAAGATCTAGGCGATGCCCCCTTCCTTGATCGGCTTCGCCGAGATCAGAAGTCTCTAAAGGG
ACGAGGCAACACTCTCGGTCTGAACATCGAAACAGCCACTTGTGTTGGAAAGCAAATAGTAGAGAGGATTCTGAAAGAAG
AATCCGATGAGACATTTAGAATGACCATGGCCTCCGCACTTGCTTCGCGGTACCTAACTGACATGACTGTTGAAGAAATG
TCAAGGGACTGGTTCATGCTCATGCCCAAGCAGAAAGTGGCTGGCCCTCTTTGTGTCAGAATGGACCAGGCGATAATGGA
TAAGAACATCATACTGAAAGCGAACTTCAGTGTGATTTTTGACCGGTTGGAGAATCTGACATTACTAAGGGCTTTCACCG
AAGAGGGGAGCAATTGTTGGCGAAATTTCACCATTGCCTTCTTTTCCAGGACATACTAATGAGGATGTCAAAAATGCAATT
GGGGTCCTCATCGGGGGACTTGAATGGAATGATAACACAGTTCGAGTCTCTGAAGCTCTACAGAGATTCGCTTGGAGAAG
CAGTAATGAGACTGGGGGACCTCCATTCACTACAACACAGAAACGGAACCAATTAGGTCAGAAGTTTGAA
GAAATAAGATGGCTGATTGAAGAAGTGAGGCATAAATTGAAGACGACAGAGAGTAGTTTTGAACAAATAACATTTATGCA
AGCATTACAGCTATTGTTTGAAGTGGAACAAGAGATTAGAACGTTCTCGTTTCAGCTTATTTAATGATAAAAACACCCTT
GTTTCTACT

SEQ ID NO: 15 (HA, 105p30)
AGCGAAAGCAGGGGAAAATAAAAGCAACCAAAATGAAAGTAAAACTACTGGTTCTGTTATGTACATTTACAGCTACATAT
GCAGACACAATATGTATAGGCTACCATGCCAACAACTCAACCGACACTGTTGACACAGTACTTGAGAAGAATGTAACAGT
GACACACTCTGTCAACCTACTTGAGGACAGTCACAATGGAAAACTATGTCTACTAAAAGGAATAGCCCCACTACAATTGG
GTAATTGCAGCGTTGCCGGATGGATCTTAGGAAACCCAGAATGCGAATTACTGATTTCCAAGGAATCATGGTCCTACATT
GTAGAAACACCCAAATCCTGAGAATGGAACATGTTACCCAGGGTATTTCGCCGACTATGAGGAACTGAGGGAGCAATTGAG
TTCAGTATCTTCATTTGAAAGGTTCGAAATATTCCCCAAAGAGAGCTCATGGCCCAACCACACCGTAACCGGAGTATCAG
CATCATGCTCCCATAACGGGAAAAGCAGTTTTTACAGAAATTTGCTATGGCTGACGGGAAGAATGGTTTGTACCCAAAC
CTGAGCAAGTCCTATGCAAACAACAAAGAGAAAGAAGTCCTTGTACTATGGGGTGTTCATCACCCGCCTAACATAGGGGA
CCAAAGGGCCCTCTATCATACAGAAAATGCTTATGTCTCTGTAGTGTCTTCACATTATAGCAGAAGATTCACCCCAGAAA
TAGCCAAAAGACCCAAGGTGAGAGACCAGGAAGGAAGAATCAACTACTACTGGACTCTGCTGGAACCCGGGGATACAATA
ATATTTGAGGCAAATGGAAATCTAATAGCGCCAAGGTATGCTTTCGCACTGATGTAGAGGCTTGGGATCAGGAATCATCAC
CTCAAATGCACCAATGGATGAATGTGATGCAAAGTGTCAAACACCTCAGGGAGCTATAAACAGCAGTCTTCCTTTCCAGA
ATGTACACCCAGTCACAATAGGAGAGTGTCCAAAGTATGTCAGGAGTGCAAAATTAAGGATGGTTACAGGACTAAGGAAC
ATCCCATCCATTCAATCCAGAGGTTTGTTTGGAGCAATTGCCGGTTTCATTGAAGGGGGGTGGACTGGAATGGTAGATGG
TTGGTATGGTTATCATCATCAGAATGAGCAAGGATCTGGGTATGCTGCAGATCAAAAAAGCACACAAAATGCCATTAACG
GGATTACAAACAAGGTGAATTCTGTAATTGAGAAAATGAACACTCAATTCACAGCTGTGGGCAAAGAATTCAACAAATTG
GAAAGAAGGATGGAAAACTTAAATAAAAAAGTTGATGATGGGTTTCTAGACATTTGGACCTATAATGCAGAATTGTTGGT
TCTACTGGAAAATGAAAGGACTTTGGATTTCCATGACTCCAACGTGAAGAATCTGTATGAGAAAGTAAAAAGCCAATTAA
AGAATAATGCCAAAGAAATAGGAAACGGGTGTTTTGAATTCTATCACAAGTGTAACGATGAATGCATGGAGAGTGTGAAA
AATGGAACTTATGACTATCCAAAATATTCCGAAGAATCAAAGTTAAACAGAGAGAAAATTGGGAGTGAAATTGGAATC
AATGGGAGTCTATCAGATTCTGGCGATCTACTCAACAGTCGCCAGTTCCCTGGTTCTTTTGGTCTCCCTGGGGGCAATCA
GCTTCTGGATGTGTTCCAATGGGTCTTTGCAGTGTAGAATATGCATCTAAGACCAGAATTTCAGAAATATAAGGAAAAAC
ACCCTTGTTTCTACT

SEQ ID NO: 16 (NA, 105p30)
AGCAAAAGCAGGAGTTTAAAATGAATCCAAATCAAAAAATAATAACCATTGGATCAATCAGTATAGCAATCGGAATAATT
AGTCTAATGTTGCAAATAGGAAATATTATTTCAATATGGGCTAGTCACTCAATCCAAACTGGAAGTCAAAACCACACTGG
AATATGCAACCAAAAAATCATCACATATGAAAACAGCACCTGGGTGAATCACACATATGTTAATATTAACAACACTAATG
TTGTTGCTGGAAAGGACAAAACTTCAGTGACACTGGCCGGCAATTCATCTCTTTGTCCTATCAGTGGATGGGCTATATAC
ACAAAAGACAACAGCATAAGAATTGGCTCCAAAGGAGATGTTTTTGTCATAAGAGAACCTTTCATATCATGTTCTCACTT
GGAATGCAGAACCTTTTTTCTGACCCAAGGTGCTCTATTAAATGACAAACATTCAAATGGAACCGTTAAGGACAGAAGTC
CTTATAGGGCCTTAATGAGCTGTCCTCTAGGTGAAGCCCGTGCACCATACAATTCAAAGTTTGAATCAGTTGCATGGTCA
GCAAGCGCATGCCATGATGGCAAGGGCTGGTTAACAATCGGAATTTCTGGTCCAGACAATGGAGCTGTGGCTGTACTAAA
ATACAACGGAATAATAACTGAAACCATAAAAAGTTGGGAAAAGCGAATATTGAGAACACAAGAGTCTGAATGTGTTTGTG
TGAACGGGTCATGTTTCACCATAATGACCGATGGCCCGAGTAATGGGGCCGCCTCGTACAAAATCTTCAAGATCGAAAAG
GGGAAGGTTACTAAATCAACAGAGTTGAATGCACCCAATTTTCATTATGAGGAATGTTCCTGTTACCCAGACACTGGCAC
AGTGATGTGTGTATGCAGGGACAACTGGCATGGTTCAAATCGACCTTGGGTATCTTTTAATCAAAACTTGGATTATCAAA
TAGGATACATCTGCAGTGGAGTGTTCGGTGACAATCCGCGTCCCAAAGATGGGAAGGGCAGCTGTAATCCAGTGACTGTT
GATGGAGCAGACGGAGTTAAGGGGTTTTCATACAAATATGGTAATGGTGTTTGGATAGGAAGGACTAAAAGTAACAGACT
TAGAAAGGGGTTTGAGATGATTTGGGATCCTAATGGATGGACAGATACCGACAGTGATTTCTCAGTGAAACAGGATGTTG
TGGCAATAACTGATTGGTCAGGGTACAGCGGAAGTTTCGTCCAACATCCTGAGTTAACAGGATTGGACTGTATAAGACCT
TGCTTCTGGGTTGAGTTAGTCAGAGGACTGCCTAGAGAAAATACAACAATCTGGACTAGTGGGAGCAGCATTTCTTTTTG
TGGCGTTGATAGTGATACTGCAAATTGGTCTTGGCCAGACGGTGCTGAGTTGCCGTTCACCATTGACAAGTAGCTCGTTG
AAAAAAACTCCTTGTTTCTACT
```

REFERENCES

[1] Cobbin et al. (2013) *J. Virol.* 87(10):5577-5585.
[2] Luytjes et al. (1989) *Cell* 59(6):1107-1113.
[3] Enami et al. (1990) *PNAS* 87(10):3802-3805.
[4] Fodor et al. (1999) *J. Virol.* 73(11):9679-9682.
[5] Hoffmann et al. (2000) *PNAS* 97(11):6108-6113.
[6] WO2009/000891
[7] WO2011/012999
[8] Verity et al. (2012) *Influenza Other Respir. Viruses* 6(2): 101-109
[9] WO2010/133964

[10] Sambrook et al, Molecular Cloning: A Laboratory Manual, 2 ed., 1989, Cold Spring Harbor Press, Cold Spring Harbor, N. Y

[11] WO2011/145081

[12] Kistner et al. (1998) Vaccine 16:960-8.

[13] Kistner et al. (1999) Dev Biol Stand 98:101-110.

[14] Bruhl et al. (2000) Vaccine 19:1149-58.

[15] WO97/37000.

[16] Brands et al. (1999) Dev Biol Stand 98:93-100.

[17] Halperin et al. (2002) Vaccine 20:1240-7.

[18] Tree et al. (2001) Vaccine 19:3444-50.

[19] Pau et al. (2001) Vaccine 19:2716-21.

[20] http://www.atcc.org/

[21] http://locus.umdnj.edu/

[22] WO03/076601.

[23] WO2005/042728.

[24] WO03/043415.

[25] WO01/85938.

[26] WO2006/108846.

[27] EP-A-1260581 (WO01/64846).

[28] WO2006/071563.

[29] WO2005/113758.

[30] WO03/023021.

[31] WO03/023025.

[32] WO2006/027698.

[33] WO97/37001.

[34] EP-B-0870508.

[35] U.S. Pat. No. 5,948,410.

[36] WO2007/052163.

[37] WO02/28422.

[38] WO02/067983.

[39] WO02/074336.

[40] WO01/21151.

[41] WO02/097072.

[42] WO2005/113756.

[43] Huckriede et al. (2003) Methods Enzymol 373:74-91.

[44] Vaccines. (eds. Plotkins & Orenstein). 4th edition, 2004, ISBN: 0-7216-9688-0.

[45] Treanor et al. (1996) J Infect Dis 173:1467-70.

[46] Keitel et al. (1996) Clin Diagn Lab Immunol 3:507-10.

[47] Herlocher et al. (2004) J Infect Dis 190(9):1627-30.

[48] Le et al. (2005) Nature 437(7062):1108.

[49] WO2008/068631.

[50] Gennaro (2000) Remington: The Science and Practice of Pharmacy. 20th edition, ISBN: 0683306472.

[51] Banzhoff (2000) Immunology Letters 71:91-96.

[52] Nony et al. (2001) Vaccine 27:3645-51.

[53] WO90/14837

[54] Podda & Del Giudice (2003) Expert Rev Vaccines 2:197-203

[55] Podda (2001) Vaccine 19: 2673-2680

[56] Vaccine Design: The Subunit and Adjuvant Approach (eds. Powell & Newman) Plenum Press 1995 (ISBN 0-306-44867-X)

[57] Vaccine Adjuvants: Preparation Methods and Research Protocols (Volume 42 of Methods in Molecular Medicine series). ISBN: 1-59259-083-7. Ed. O'Hagan

[58] WO 2008/043774

[59] US 2007/014805

[60] US 2007/0191314

[61] Fox et al. (2013) Vaccine 31:1633-1640

[62] Allison & Byars (1992) Res Immunol 143:519-25

[63] Hariharan et al. (1995) Cancer Res 55:3486-9

[64] Suli et al. (2004) Vaccine 22(25-26):3464-9

[65] WO 95/11700

[66] U.S. Pat. No. 6,080,725

[67] WO 2005/097181

[68] WO 2006/113373

[69] Han et al. (2005) Impact of Vitamin E on Immune Function and Infectious Diseases in the Aged at Nutrition, Immune functions and Health EuroConference, Paris, 9-10 Jun. 2005

[70] U.S. Pat. No. 6,630,161

[71] Potter & Oxford (1979) Br Med Bull 35: 69-75.

[72] Greenbaum et al. (2004) Vaccine 22:2566-77.

[73] Zurbriggen et al. (2003) Expert Rev Vaccines 2:295-304.

[74] Piascik (2003) J Am Pharm Assoc (Wash D.C.). 43:728-30.

[75] Mann et al. (2004) Vaccine 22:2425-9.

[76] Halperin et al. (1979) Am J Public Health 69:1247-50.

[77] Herbert et al. (1979) J Infect Dis 140:234-8.

[78] Chen et al. (2003) Vaccine 21:2830-6.

[79] Dormitzer et al. (2013) Sci Trans Med 5(185): 185ra68

[80] Hoffmann et al. (2002) Vaccine 20(25-26):3165-70.

The invention claimed is:

1. A method for generating a reassortant influenza virus, comprising the steps of:
    (i) contacting a culture host with a parent influenza virus strain comprising a first hemagglutinin (HA) gene and a first neuraminidase (NA) gene;
    (ii) introducing into the culture host one or more expression construct(s) comprising one or more influenza genes, wherein said influenza genes comprise a second HA gene or a second NA gene;
    (iii) culturing the culture host to produce reassortant viruses; and
    (iv) selecting for the reassortant virus that comprises the second HA gene or the second NA gene,
wherein:
    step (iv) comprises negative selection against the first HA or first NA, wherein the negative selection comprises contacting the culture host or the reassortant influenza viruses that have been separated from the culture host with one or more antibodies which are specific for the first HA or with one or more antibodies which are specific for the first NA.

2. The method of claim 1, further comprising step (v) of isolating the reassortant influenza virus comprising the second HA gene or the second NA gene.

3. The method of claim 2, wherein the isolated reassortant influenza virus is selected from the group consisting of a 7:1 reassortant influenza virus, a 6:2 reassortant influenza virus, and a 5:3 reassortant influenza virus.

4. The method of claim 1, wherein step (iv) comprises selecting for the reassortant virus that comprises the second HA gene or the second NA gene.

5. The method of claim 4, further comprising step (v) of isolating the reassortant influenza virus comprising the second HA gene or the second NA gene.

6. The method of claim 4, wherein
    the parent influenza virus strain further comprises a first polymerase basic subunit 1 (PB1) gene, a first polymerase basic subunit 2 (PB2) gene, a first polymerase acidic subunit (PA) gene, a first matrix protein (M) gene, a first non-structural protein (NS) gene, and a first nucleoprotein (NP) gene,
    the one or more influenza genes of the expression construct(s) further comprise a second PB1 gene, a second PB2 gene, a second PA gene, a second M gene, a second NS gene, or a second NP gene, and
    step (iv) comprises selecting for a reassortant virus that comprises the second PB1 gene, second PB2 gene, second PA gene, second M gene, second NS gene, or second NP gene.

7. The method of claim 6, further comprising step (v) of isolating the reassortant influenza virus comprising (i) the second HA or the second NA gene and (ii) the second PB gene, second PB2 gene, second PA gene, second M gene, second NS gene, or second NP gene.

8. The method of claim 1, wherein the one or more expression construct(s) comprises no more than seven, six, five, four, three, or two influenza genes.

9. The method of claim 1, wherein the one or more expression construct(s) is one or more plasmid(s), one or more linear DNA molecule(s), or one or more RNA molecule(s).

10. The method of claim 1, wherein the one or more expression construct(s) is one or more bi-directional expression construct(s), wherein at least one gene is located between an upstream pol II promoter and a downstream non-endogenous pol I promoter.

11. The method of claim 1, wherein the one or more expression construct(s) is introduced into the culture host at the same time as or before the culture host is contacted with the parent influenza virus strain.

12. The method of claim 1, wherein the one or more expression construct(s) is introduced into the culture host after the culture host is contacted with the parent influenza virus strain.

13. The method of claim 1, wherein the negative selection further comprises contacting the culture host or the reassortant influenza viruses that have been separated from the culture host with one or more antibodies which are specific for the first NA.

14. The method of claim 1, wherein step (iv) comprises positive selection for the second HA or the second NA.

15. The method of claim 14, wherein the positive selection comprises contacting the culture host or the reassortant influenza viruses that have been separated from the culture host with one or more antibodies which are specific for the second HA or the second NA.

16. The method of claim 1, wherein the second HA gene comprises one or more modification(s) relative to wild-type.

17. The method of claim 16, wherein the one or more modification(s) of the second HA gene is the deletion of a polybasic cleavage site.

18. The method of claim 1, wherein the culture host is an embryonated avian egg, a mammalian cell, or an avian cell.

19. The method of claim 18, wherein the culture host is an MDCK, Vero, PerC6, CEF, or EB66 cell.

20. The method of claim 19, wherein the cell grows adherently.

21. The method of claim 19, wherein the cell grows in suspension.

22. The method of claim 1, wherein the reassortant influenza virus is an influenza A virus or an influenza B virus.

23. A method for generating a reassortant influenza virus, comprising the steps of:
    (i) contacting a culture host with a parent influenza virus strain comprising a first hemagglutinin (HA) gene and a first neuraminidase (NA) gene;
    (ii) introducing into the culture host one or more expression construct(s) comprising one or more influenza genes, wherein said influenza genes comprise a second HA gene or a second NA gene;
    (iii) culturing the culture host to produce reassortant viruses; and
    (iv) selecting for the reassortant virus that comprises the second HA gene or the second NA gene, wherein step (iv) comprises negative selection against the first HA or first NA, wherein the negative selection comprises contacting the culture host or the reassortant influenza viruses that have been separated from the culture host with one or more antibodies which are specific for the first HA or with one or more antibodies which are specific for the first NA, and wherein the method comprises a step of pre-passaging an influenza virus strain in cell culture or eggs to produce the parent influenza strain.

24. The method of claim 2, further comprising preparing a vaccine, wherein the method comprises formulating the reassortant influenza virus with one or more pharmaceutically acceptable carriers.

* * * * *

SEQUENCE LISTING

<160> NUMBER OF SEQ ID NOS: 16

<210> SEQ ID NO 1
<211> LENGTH: 2233
<212> TYPE: DNA
<213> ORGANISM: Influenza PR8-X

<400> SEQUENCE: 1

```
agcgaaagca ggtactgatc caaaatggaa gattttgtgc gacaatgctt caatccgatg      60
attgtcgagc ttgcggaaaa aacaatgaaa gagtatgggg aggacctgaa aatcgaaaca     120
aacaaatttg cagcaatatg cactcacttg gaagtatgct tcatgtattc agattttcac     180
ttcatcaatg agcaaggcga gtcaataatc gtagaacttg gtgatccaaa tgcacttttg     240
aagcacagat ttgaaataat cgagggaaga gatcgcacaa tggcctggac agtagtaaac     300
agtatttgca acactacagg ggctgagaaa ccaaagtttc taccagattt gtatgattac     360
aaggagaata gatttatcga aattggagta acaaggagag aagttcacat atactatctg     420
gaaaaggcca ataaaattaa atctgagaaa acacacatcc acattttctc gttcactggg     480
```

-continued

```
gaagaaatgg ccacaaaggc agactacact ctcgatgaag aaagcagggc taggatcaaa      540
accagactat tcaccataag acaagaaatg gccagcagga gcctctggga ttccttttcgt      600 cagtccgaga gaggagaaga gacaattgaa gaaaggtttg aaatcacagg aacaatgcgc      660
aagcttgccg accaaagtct cccgccgaac ttctccagcc ttgaaaattt tagagcctat      720
gtggatggat tcgaaccgaa cggctacatt gagggcaagc tgtctcaaat gtccaaagaa      780
gtaaatgcta gaattgaacc ttttttgaaa acaacaccac gaccacttag acttccgaat      840
gggcctccct gttctcagcg gtccaaattc ctgctgatgg atgccttaaa attaagcatt      900
gaggacccaa gtcatgaagg agagggaata ccgctatatg atgcaatcaa atgcatgaga      960
acattctttg gatggaagga acccaatgtt gttaaaccac acgaaaaggg aataaatcca     1020
aattatcttc tgtcatggaa gcaagtactg cagaactgc aggacattga gaatgaggag     1080
aaaattccaa agactaaaaa tatgaagaaa acaagtcagc taaagtgggc acttggtgag     1140
aacatggcac cagaaaaggt agactttgac gactgtaaag atgtaggtga tttgaagcaa     1200
tatgatagtg atgaaccaga attgaggtcg cttgcaagtt ggattcagaa tgagtttaac     1260
aaggcatgcg aactgacaga ttcaagctgg atagagctcg atgagattgg agaagatgtg     1320
gctccaattg aacacattgc aagcatgaga aggaattatt tcacatcaga ggtgtctcac     1380
tgcagagcca cagaatacat aatgaagggg gtgtacatca atactgcctt gcttaatgca     1440
tcttgtgcag caatggatga tttccaatta attccaatga taagcaagtg tagaactaag     1500
gagggaaggc gaaagaccaa cttgtatggt ttcatcataa aaggaagatc ccacttaagg     1560
aatgacaccg acgtggtaaa cttttgtgagc atggagtttt ctctcactga cccaagactt     1620
gaaccacata aatgggagaa gtactgtgtt cttgagatag gagatatgct tataagaagt     1680
gccataggcc aggtttcaag gcccatgttc ttgtatgtga aacaaatgg aacctcaaaa     1740 attaaaatga aatgggggaat ggagatgagg cgttgcctcc tccagtcact tcaacaaatt     1800
gagagtatga ttgaagctga gtcctctgtc aaagagaaag acatgaccaa agagttcttt     1860
gagaacaaat cagaaacatg gcccattgga gagtcccca aaggagtgga ggaaagttcc     1920
attgggaagg tctgcaggac tttattagca aagtcggtat tcaacagctt gtatgcatct     1980
ccacaactag aaggattttc agctgaatca agaaaactgc ttcttatcgt tcaggctctt     2040
agggacaacc ttgaacctgg gacctttgat cttgggggc tatatgaagc aattgaggag     2100
tgcctgatta tgatccctg ggttttgctt aatgcttctt ggttcaactc cttccttaca     2160
catgcattga gttagttgtg gcagtgctac tatttgctat ccatactgtc caaaaaagta     2220
ccttgtttct act                                                         2233
```

```
<210> SEQ ID NO 2
<211> LENGTH: 2341
<212> TYPE: DNA
<213> ORGANISM: Influenza PR8-X

<400> SEQUENCE: 2
agcgaaagca ggcaaaccat ttgaatggat gtcaatccga ccttactttt cttaaaagtg       60
ccaacacaaa atgctataag cacaactttc ccttatactg gagaccctcc ttacagccat      120
gggacaggaa caggatacac catggatact gtcaacagga cacatcagta ctcagaaaag      180
ggaagatggc aacaaacac cgaaactgga gcaccgcaac tcaacccgat tgatgggcca      240
ctgccagaag acaatgaacc aagtggttat gcccaaacag attgtgtatt ggaggcgatg      300
```

-continued

```
gctttccttg aggaatccca tcctggtatt tttgaaaact cgtgtattga aacgatggag      360
gttgttcagc aaacacgagt agacaagctg acacaaggcc gacagaccta tgactggact      420
ctaaatagaa accaacctgc tgcaacagca ttggccaaca caatagaagt gttcagatca      480
aatggcctca cggccaatga gtctggaagg ctcatagact tccttaagga tgtaatggag      540
tcaatgaaca aagaagaaat ggggatcaca actcattttc agagaaagag acgggtgaga      600
gacaatatga ctaagaaaat gataacacag agaacaatgg gtaaaaagaa gcagagattg      660
aacaaaagga gttatctaat tagagcattg accctgaaca caatgaccaa agatgctgag      720
agagggaagc taaaacggag agcaattgca accccaggga tgcaaataag ggggtttgta      780
tactttgttg agacactggc aaggagtata tgtgagaaac ttgaacaatc agggttgcca      840
gttggaggca atgagaagaa agcaaagttg gcaaatgttg taaggaagat gatgaccaat      900
tctcaggaca ccgaactttc tttcaccatc actggagata acaccaaatg gaacgaaaat      960
cagaatcctc ggatgttttt ggccatgatc acatatatga ccagaaatca gcccgaatgg     1020
ttcagaaatg ttctaagtat tgctccaata atgttctcaa acaaaatggc gagactggga     1080
aaagggtata tgtttgagag caagagtatg aaacttagaa ctcaaatacc tgcagaaatg     1140
ctagcaagca tcgatttgaa atatttcaat gattcaacaa gaaagaagat tgaaaaaatc     1200
cgaccgctct aatagagggg actgcatca ttgagccctg aatgatgat gggcatgttc        1260 aatatgttaa gcactgtatt aggcgtctcc atcctgaatc ttggacaaaa gagatacacc     1320
aagactactt actggtggga tggtcttcaa tcctctgacg attttgctct gattgtgaat     1380
gcacccaatc atgaagggat tcaagccgga gtcgacaggt tttatcgaac ctgtaagcta     1440
cttggaatca atatgagcaa gaaaaagtct tacataaaca gaacaggtac atttgaattc     1500
acaagttttt tctatcgtta tgggtttgtt gccaatttca gcatggagct tcccagtttt     1560
ggggtgtctg ggatcaacga gtcagcggac atgagtattg gagttactgt catcaaaaac     1620
aatatgataa acaatgatct tggtccagca acagctcaaa tggcccttca gttgttcatc     1680
aaagattaca ggtacacgta ccgatgccat agaggtgaca cacaaataca aacccgaaga     1740
tcatttgaaa taaagaaact gtgggagcaa acccgttcca aagctggact gctggtctcc     1800
gacggaggcc caaatttata caacattaga aatctccaca ttcctgaagt ctgcctaaaa     1860
tgggaattga tggatgagga ttaccagggg cgtttatgca acccactgaa cccatttgtc     1920
agccataaag aaattgaatc aatgaacaat gcagtgatga tgccagcaca tggtccagcc     1980
aaaaacatgg agtatgatgc tgttgcaaca acacactcct ggatccccaa agaaatcga       2040 tccatcttga atacaagtca agaggagta cttgaggatg aacaaatgta ccaaaggtgc        2100
tgcaatttat ttgaaaaatt cttccccagc agttcataca gaagaccagt cgggatatcc     2160
agtatggtgg aggctatggt ttccagagcc cgaattgatg cacggattga tttcgaatct     2220
ggaaggataa agaagaaga gttcactgag atcatgaaga tctgttccac cattgaagag        2280
ctcagacggc aaaaatagtg aatttagctt gtccttcatg aaaaaatgcc ttgtttctac     2340
t                                                                    2341
```

<210> SEQ ID NO 3
<211> LENGTH: 2341
<212> TYPE: DNA
<213> ORGANISM: Influenza PR8-X

<400> SEQUENCE: 3

```
agcgaaagca ggtcaattat attcaatatg gaaagaataa aagaactaag aaatctaatg       60
```

-continued

```
tcgcagtctc gcacccgcga gatactcaca aaaaccaccg tggaccatat ggccataatc   120
aagaagtaca catcaggaag acaggagaag aacccagcac ttaggatgaa atggatgatg   180
gcaatgaaat atccaattac agcagacaag aggataacgg aaatgattcc tgagagaaat   240
gagcaaggac aaactttatg gagtaaaatg aatgatgccg gatcagaccg agtgatggta   300
tcacctctgg ctgtgacatg gtggaatagg aatggaccaa taacaaatac agttcattat   360
ccaaaaatct acaaaactta ttttgaaaga gtagaaaggc taaagcatgg aacctttggc   420
cctgtccatt ttagaaacca agtcaaaata cgtcggagag ttgacataaa tcctggtcat   480
gcagatctca gtgccaagga ggcacaggat gtaatcatgg aagttgtttt ccctaacgaa   540
gtgggagcca ggatactaac atcggaatcg caactaacga taaccaaaga gaagaaagaa   600
gaactccagg attgcaaaat ttctcctttg atggttgcat acatgttgga gagagaactg   660
gtccgcaaaa cgagattcct cccagtggct ggtggaacaa gcagtgtgta cattgaagtg   720
ttgcatttga ctcaaggaac atgctgggaa cagatgtata ctccaggagg ggaagtgagg   780
aatgatgatg ttgatcaaag cttgattatt gctgctagga acatagtgag aagagctgca   840
gtatcagcag atccactagc atctttattg gagatgtgcc acagcacaca gattggtgga   900
attaggatgg tagacatcct taggcagaac ccaacagaag agcaagccgt ggatatatgc   960
aaggctgcaa tgggactgag aattagctca tccttcagtt ttggtggatt cacatttaag   1020
agaacaagcg gatcatcagt caagagagag gaagaggtgc ttacgggaaa tcttcaaaca   1080
ttgaagataa gagtgcatga gggatatgaa gagttcacaa tggttgggag aagagcaaca   1140
gccatactca gaaaagcaac caggagattg attcagctga tagtgagtgg gagagacgaa   1200
cagtcgattg ccgaagcaat aattgtggcc atggtatttt cacaagagga ttgtatgata   1260
aaagcagtca gaggtgatct gaatttcgtc aatagggcga atcagcgatt gaatcctatg   1320
catcaacttt taagacattt tcagaaggat gcgagagtgc tttttcaaaa ttggggagtt   1380
gaacctatcg acaatgtgat gggaatgatt gggatattgc ccgacatgac tccaagcatc   1440
gagatgtcaa tgagaggagt gagaatcagc aaaatgggtg tagatgagta ctccagcacg   1500
gagagggtag tggtgagcat tgaccgtttt ttgagaatcc gggaccaacg aggaaatgta   1560
ctactgtctc ccgaggaggt cagtgaaaca cagggaacag agaaactgac aataacttac   1620
tcatcgtcaa tgatgtggga gattaatggt cctgaatcag tattggtcaa tacctatcaa   1680
tggatcatca gaaactggga aactgttaaa attcagtggt cccagaaccc tacaatgcta   1740
tacaataaaa tggaatttga accatttcag tctttagtac ctaaggccat tagaggccaa   1800
tacagtgggt ttgtaagaac tctgttccaa caaatgaggg atgtgcttgg gacatttgat   1860
accgcacaga taataaaaact tcttcccttc gcagccgctc caccaaagca aagtagaatg   1920
cagttctcct catttactgt gaatgtgagg ggatcaggaa tgagaatact tgtaaggggc   1980
aattctcctg tattcaacta taacaaggcc acgaagagac tcacagttct cggaaaggat   2040
gctggcactt taactgaaga cccagatgaa ggcacagctg gagtggagtc cgctgttctg   2100
aggggattcc tcattctggg caaagaagac aagagatatg gccagcact aagcatcaat   2160 gaactgagca accttgcgaa aggagagaag gctaatgtgc taattgggca aggagacgtg   2220
gtgttggtaa tgaaacggaa acgggactct agcatactta ctgacagcca gacagcgacc   2280
aaaagaattc ggatggccat caattagtgt cgaatagttt aaaaacgacc ttgtttctac   2340
t                                                                      2341
```

<210> SEQ ID NO 4
<211> LENGTH: 1565
<212> TYPE: DNA
<213> ORGANISM: Influenza PR8-X

<400> SEQUENCE: 4

```
agcaaaagca gggtagataa tcactcactg agtgacatca aaatcatggc gtctcaaggc        60
accaaacgat cttacgaaca gatggagact gatggagaac gccagaatgc cactgaaatc       120
agagcatccg tcggaaaaat gattggtgga attggacgat tctacatcca aatgtgcacc       180
gaactcaaac tcagtgatta tgagggacgg ttgatccaaa acagcttaac aatagagaga       240
atggtgctct ctgcttttga cgaaaggaga aataaatacc ttgaagaaca tcccagtgcg       300
ggaaaagatc ctaagaaaac tggaggacct atatacagga gagtaaacgg aaagtggatg       360
agagaactca tcctttatga caaagaagaa ataaggcgaa tctggcgcca agctaataat       420
ggtgacgatg caacggctgg tctgactcac atgatgatct ggcattccaa tttgaatgat       480
gcaacttatc agaggacaag agctcttgtt cgcaccggaa tggatcccag gatgtgctct       540
ctgatgcaag gttcaactct ccctaggagg tctggagccg caggtgctgc agtcaaagga       600
gttggaacaa tggtgatgga attggtcaga atgatcaaac gtgggatcaa tgatcggaac       660
ttctggaggg gtgagaatgg acgaaaaaca agaattgctt atgaaagaat gtgcaacatt       720
ctcaaaggga aatttcaaac tgctgcacaa aaagcaatga tggatcaagt gagagagagc       780
cggaacccag ggaatgctga gttcgaagat ctcactttc tagcacggtc tgcactcata       840
ttgagagggt cggttgctca caagtcctgc ctgcctgcct gtgtgtatgg acctgccgta       900
gccagtgggt acgactttga aagggaggga tactctctag tcggaataga ccctttcaga       960
ctgcttcaaa acagccaagt gtacagccta atcagaccaa atgagaatcc agcacacaag      1020
agtcaactgg tgtggatggc atgccattct gccgcatttg aagatctaag agtattaagc      1080
ttcatcaaag ggacgaaggt gctcccaaga gggaagcttt ccactagagg agttcaaatt      1140
gcttccaatg aaaatatgga gactatggaa tcaagtacac ttgaactgag aagcaggtac      1200
tgggccataa ggaccagaag tggaggaaac accaatcaac agagggcatc tgcgggccaa      1260
atcagcatac aacctacgtt ctcagtacag agaaatctcc cttttgacag aacaaccatt      1320
atggcagcat tcaatgggaa tacagagggg agaaacatctg acatgaggac cgaaatcata      1380
aggatgatgg aaagtgcaag accagaagat gtgtctttcc aggggcgggg agtcttcgag      1440
ctctcggacg aaaaggcagc gagcccgatc gtgccttcct ttgacatgag taatgaagga      1500
tcttatttct cggagacaa tgcagaggag tacgacaatt aaagaaaaat acccttgttt      1560
ctact                                                                   1565
```

<210> SEQ ID NO 5
<211> LENGTH: 1027
<212> TYPE: DNA
<213> ORGANISM: Influenza PR8-X

<400> SEQUENCE: 5

```
agcaaaagca ggtagatatt gaaagatgag tcttctaacc gaggtcgaaa cgtacgtact        60
ctctatcatc ccgtcaggcc ccctcaaagc cgagatcgca cagagacttg aagatgtctt       120
tgcagggaag aacaccgatc ttgaggttct catggaatgg ctaaagacaa gaccaatcct       180
gtcacctctg actaagggga tttttaggatt tgtgttcacg ctcaccgtgc ccagtgagcg       240
aggactgcag cgtagacgct ttgtccaaaa tgcccttaat gggaacgggg atccaaataa       300
```

-continued

```
catgga caaa  gcagttaaac  tgtataggaa  gctcaagagg  gagataacat  tccatggggc       360
caaagaaatc  tcactcagtt  attctgctgg  tgcacttgcc  agttgtatgg  gcctcatata       420
caacaggatg  ggggctgtga  ccactgaagt  ggcatttggc  ctggtatgtg  caacctgtga       480
acagattgct  gactcccagc  atcggtctca  taggcaaatg  gtgacaacaa  ccaatccact       540
aatcagacat  gagaacagaa  tggtttttagc  cagcactaca  gctaaggcta  tggagcaaat       600
ggctggatcg  agtgagcaag  cagcagaggc  catggaggtt  gctagtcagg  ctagacaaat       660
ggtgcaagcg  atgagaacca  ttgggactca  tcctagctcc  agtgctggtc  tgaaaaatga       720
tcttcttgaa  aatttgcagg  cctatcagaa  acgaatgggg  gtgcagatgc  aacggttcaa       780
gtgatcctct  cactattgcc  gcaaatatca  ttgggatctt  gcacttgaca  ttgtggattc       840
ttgatcgtct  ttttttcaaa  tgcatttacc  gtcgctttaa  atacggactg  aaaggagggc       900
cttctacgga  aggagtgcca  aagtctatga  gggaagaata  tcgaaaggaa  cagcagagtg       960
ctgtggatgc  tgacgatggt  cattttgtca  gcatagagct  ggagtaaaaa  actaccttgt      1020
ttctact                                                                     1027
```

```
<210> SEQ ID NO 6
<211> LENGTH: 890
<212> TYPE: DNA
<213> ORGANISM: Influenza PR8-X

<400> SEQUENCE: 6
```

```
agcaaaagca  gggtgacaaa  aacataatgg  atccaaacac  tgtgtcaagc  tttcaggtag        60
attgctttct  ttggcatgtc  cgcaaacgag  ttgcagacca  agaactaggt  gatgccccat       120
tccttgatcg  gcttcgccga  gatcagaaat  ccctaagagg  aaggggcagt  actctcggtc       180
tggacatcaa  gacagccaca  cgtgctggaa  agcagatagt  ggagcggatt  ctgaaagaag       240
aatccgatga  ggcacttaaa  atgaccatgg  cctctgtacc  tgcgtcgcgt  tacctaactg       300
acatgactct  tgaggaaatg  tcaagggact  ggtccatgct  catacccaag  cagaaagtgg       360
caggccctct  ttgtatcaga  atggaccagg  cgatcatgga  taagaacatc  atactgaaag       420
cgaacttcag  tgtgattttt  gaccggctgg  agactctaat  attgctaagg  gctttcaccg       480
aagagggagc  aattgttggc  gaaatttcac  cattgccttc  tcttccagga  catactgctg       540
aggatgtcaa  aaatgcagtt  ggagtcctca  tcggaggact  tgaatggaat  gataacacag       600
ttcgagtctc  tgaaactcta  cagagattcg  cttggagaag  cagtaatgag  aatgggagac       660
ctccactcac  tccaaaacag  aaacgagaaa  tggcgggaac  aattaggtca  gaagtttgaa       720
gaaataagat  ggttgattga  agaagtgaga  cacaaactga  agataacaga  gaatagtttt       780
gagcaaataa  catttatgca  agccttacat  ctattgcttg  aagtggagca  agagataaga       840
actttctcgt  ttcagcttat  ttagtactaa  aaaacaccct  tgtttctact                   890
```

```
<210> SEQ ID NO 7
<211> LENGTH: 1775
<212> TYPE: DNA
<213> ORGANISM: Influenza PR8-X

<400> SEQUENCE: 7
```

```
agcaaaagca  ggggaaaata  aaaacaacca  aaatgaaggc  aaacctactg  gtcctgttat        60
gtgcacttgc  agctgcagat  gcagacacaa  tatgtataggc  ctaccatacg  aacaattcaa       120
ccgacactgt  tgacacagta  ctcgagaaga  atgtgacagt  gacacactct  gttaacctgc       180
```

-continued
___ tcgaagacag ccacaacgga aaactatgta gattaaaagg aatagcccca ctacaattgg      240
ggaaatgtaa catcgccgga tggctcttgg gaaacccaga atgcgaccca ctgcttccag      300
tgagatcatg gtcctacatt gtagaaacac caaactctga gaatggaata tgttatccag      360
gagatttcat cgactatgag gagctgaggg agcaattgag ctcagtgtca tcattcgaaa      420
gattcgaaat atttcccaaa gaaagctcat ggcccaacca caacacaaac ggagtaacgg      480
cagcatgctc ccatgagggg aaaagcagtt tttacagaaa tttgctatgg ctgacggaga      540
aggagggctc atacccaaag ctgaaaaatt cttatgtgaa caaaaaaggg aaagaagtcc      600
ttgtactgtg gggtattcat cacccgccta acagtaagga acaacagaat ctctatcaga      660
atgaaaatgc ttatgtctct gtagtgactt caaattataa caggagattt accccggaaa      720
tagcagaaag acccaaagta agagatcaag ctgggaggat gaactattac tggaccttgc      780
taaaacccgg agacacaata atatttgagg caaatggaaa tctaatagca ccaatgtatg      840
ctttcgcact gagtagaggc tttgggtccg gcatcatcac ctcaaacgca tcaatgcatg      900
agtgtaacac gaagtgtcaa acacccctgg agctataaa cagcagtctc ccttaccaga      960
atatacaccc agtcacaata ggagagtgcc caaaatacgt caggagtgcc aaattgagga     1020
tggttacagg actaaggaac attccgtcca ttcaatccag aggtctattt ggagccattg     1080
ccggttttat tgaaggggga tggactggaa tgatagatgg atggtatggt tatcatcatc     1140
agaatgaaca gggatcaggc tatgcagcgg atcaaaaaag cacacaaaat gccattaacg     1200
ggattacaaa caaggtgaac actgttatcg agaaaatgaa cattcaattc acagctgtgg     1260
gtaaagaatt caacaaatta gaaaaaagga tggaaaattt aaataaaaaa gttgatgatg     1320
gatttctgga catttggaca tataatgcag aattgttagt tctactggaa aatgaaagga     1380
ctctggaatt ccatgactca aatgtgaaga atctgtatga gaaagtaaaa agccaattaa     1440
agaataatgc caaagaaatc ggaaatggat gttttgagtt ctaccacaag tgtgacaatg     1500
aatgcatgga aagtgtaaga aatgggactt atgattatcc caaatattca gaagagtcaa     1560
agttgaacag ggaaaaggta gatggagtga aattggaatc aatggggatc tatcagattc     1620
tggcgatcta ctcaactgtc gccagttcac tggtgctttt ggtctccctg ggggcaatca     1680
gtttctggat gtgttctaat ggatctttgc agtgcagaat atgcatctga gattagaatt     1740
tcagagatat gaggaaaaac acccttgttt ctact                               1775

<210> SEQ ID NO 8
<211> LENGTH: 1413
<212> TYPE: DNA
<213> ORGANISM: Influenza PR8-X

<400> SEQUENCE: 8
agcaaaagca ggggtttaaa atgaatccaa atcagaaaat aataaccatt ggatcaatct       60
gtctggtagt cggactaatt agcctaatat tgcaaatagg aatataatc tcaatatgga      120 ttagccattc aattcaaact ggaagtcaaa accatactgg aatatgcaac caaaacatca      180
ttacctataa aaatagcacc tgggtaaagg acacaacttc agtgatatta accggcaatt      240
catctctttg tccatccgt gggtgggcta tatacagcaa agacaatagc ataagaattg      300
gttccaaagg agacgttttt gtcataagag agcccttat ttcatgttct cacttggaat      360
gcaggacctt ttttctgacc caaggtgcct tactgaatga caagcattca agtgggactg      420
ttaaggacag aagcccttat agggccttaa tgagctgccc tgtcggtgaa gctccgtccc      480
cgtacaattc aagatttgaa tcggttgctt ggtcagcaag tgcatgtcat gatggcatgg      540

```
gctggctaac aatcggaatt tcaggtccag ataatggagc agtggctgta ttaaaataca      600
acggcataat aactgaaacc ataaaaagtt ggaggaagaa aatattgagg acacaagagt      660
ctgaatgtgc ctgtgtaaat ggttcatgtt ttactataat gactgatggc ccgagtgatg      720
ggctggcctc gtacaaaatt ttcaagatcg aaaaggggga ggttactaaa tcaatagagt      780
tgaatgcacc taattctcac tatgaggaat gttcctgtta ccctgatacc gacaaagtga      840
tgtgtgtgtg cagagacaat tggcatggtt cgaaccggcc atgggtgtct ttcgatcaaa      900
acctggatta tcaaatagga tacatctgca gtggggtttt cggtgacaac ccgcgtcccg      960
aagatggaac aggcagctgt ggtccagtgt atgttgatgg agcaaacgga gtaaagggat     1020
tttcatatag gtatggtaat ggtgtttgga taggaaggac caaaagtcac agttccagac     1080
atgggtttga gatgatttgg gatcctaatg gatggacaga gactgatagt aagttctctg     1140
tgaggcaaga tgttgtggca atgactgatt ggtcagggta tagcggaagt ttcgttcaac     1200
atcctgagct gacagggcta gactgtatga ggccgtgctt ctgggttgaa ttaatcaggg     1260
gacgacctaa agaaaaaaca atctggacta gtgcgagcag catttctttt tgtggcgtga     1320
atagtgatac tgtagattgg tcttggccag acggtgctga gttgccattc agcattgaca     1380
agtagtctgt tcaaaaaact ccttgtttct act                                  1413
```

<210> SEQ ID NO 9
<211> LENGTH: 2220
<212> TYPE: DNA
<213> ORGANISM: Influenza 105p30

<400> SEQUENCE: 9

```
agcgaaagca ggtactgatt cgaaatggaa gattttgtgc gacaatgctt caatccgatg       60
attgtcgagc ttgcggaaaa ggcaatgaaa gagtatggag aggacctgaa aatcgaaaca      120
aacaaatttg cagcaatatg cacccacttg gaagtatgct tcatgtattc agattttcat      180
ttcatcaatg agcaaggcga atcaataata gtagagcctg aggacccaaa tgcactttta      240
aaacacagat ttgagataat agaggggcga gatcgtacaa tggcatggac agttgtaaac      300
agtatttgca acaccacagg agctgagaaa ccaaagtttc tgccagatct gtatgattac      360
aaagagaata ggttcatcga aattggagtg acaaggagag aagttcacat atactatctg      420
gaaaaggcca caaaaattaa atctgagaag acacatattc acatttttctc atttactggc      480 gaagaaatgg ccacaaaggc cgattacact ctcgatgaag aaagcagggc tagaattaaa      540
accagactat tcaccataag gcaagaaatg gcaagcagag tctttggga ctcctttcgt      600 cagtccgaaa gaggcgaaga gacaattgaa gaaggtttg aaatcacagg gacaatgcgc      660
aggctcgctg atcaaagcct tccgccgaac ttctcctgca ttgagaattt tagagcctat      720
gtggatggat ttgaaccgaa cggctacatt gagggcaagc tttctcaaat gtccaaagaa      780
gtaaatgcta aaattgagcc ttttttgaaa acaacacctc gaccaattag acttccgaat      840
gggcctcctt gttttcagcg gtcaaaattc ctgctgatgg attctttaaa attaagcatt      900
gaggatccaa atcatgaagg ggagggaata ccactatatg atgcaatcaa gtgtatgaga      960
acattctttg gatggaaaga acccactgtt gtcaagccac acgagaaggg aataaatccg     1020
aattatctgc tgtcgtggaa gcaggtgttg aagagctgc aggacattga gagtgaggag     1080
aagattccaa gaacaaaaaa catgaaaaaa acgagtcagt taaagtgggc acttggtgag     1140
aacatggcac cagagaaggt ggattttgat gactgtaaag atataagcga tttgaagcaa     1200
```

-continued

```
tatgatagtg acgaacctga attaaggtca ttttcaagtt ggatccagaa tgagttcaac      1260
aaggcatgcg agctgaccga ttcaatctgg atagagctcg atgagattgg agaagatgtg      1320
gccccgattg aacacattgc aagcatgaga agaaattact tcacagctga ggtgtcccat      1380
tgcagagcca ctgaatatat aatgaaaggg gtatacatta atactgcttt gcttaatgca      1440
tcctgtgcag caatggatga tttccaacta attcctatga taagcaaatg tagaactaaa      1500
gagggaagga gaaagaccaa tttgtacggc ttcatcataa aaggaagatc tcacttaagg      1560
aatgataccg atgtggtaaa ctttgtgagc atggagtttt ccctcactga cccaagactt      1620
gagccacaca aatgggagaa gtactgtgtt cttgagatag gagatatgct tctaaggagt      1680
gcaataggcc aagtgtcaag gcccatgttc ttgtatgtaa gaacaaatgg aacctcaaaa      1740
attaaaatga aatggggaat ggagatgagg cgttgcctcc tccaatccct ccaacaaata      1800
gagagcatga ttgaagctga gtcctctgtc aaggagaaag acatgacaaa agagtttttt      1860
gagaatagat cagaaacatg gcccattgga gagtcaccaa aaggagtgga agaaggttcc      1920
attgggaaag tatgcaggac actattggct aaatcagtat tcaatagtct gtatgcatct      1980
ccacaattag aaggattttc agctgagtca agaaagttgc tccttattgt tcaggctctt      2040
agggacaatc tggaacctgg gacctttgat cttgggggac tatatgaagc aattgaggag      2100
tgcctgatta atgatccctg ggttttgctt aatgcttctt ggttcaactc cttcctaaaa      2160
catgcattga gatagctgag gcaatgctac tatttgttat ccatactgtc caaaaaagta      2220
```

```
<210> SEQ ID NO 10
<211> LENGTH: 2341
<212> TYPE: DNA
<213> ORGANISM: Influenza 105p30

<400> SEQUENCE: 10
```

```
agcgaaagca ggcaaaccat ttgaatggat gtcaatccga cattactttt cttaaaagtg        60
ccagcacaaa atgctataag cacaacttt ccttatactg gtgaccctcc ttacagccat       120
ggaacaggaa caggatacac catggataca gtcaacagga cacatcagta ctcagaaaga       180
ggaagatgga cgaaaaatac cgaaactgga gcaccgcaac tcaacccaat tgatgggcca       240
ctaccagaag acaatgaacc aagtggctat gcccaaacag attgtgtatt agaggcaatg       300
gctttccttg aagaatccca tcctggtatt tttgaaaact cttgtattga aacaatggag       360
gttgttcagc aaacaagggt ggacaaactg acacaaggca gacaaaccta tgactggact       420
ctaaatagga accagcctgc tgccacagca ttggcaaaca ccatagaagt attcagatca       480
aatggcctca tagcaaatga atctggaagg ctaatagact tccttaaaga tgtaatggag       540
tcgatggaca gagcgaagt agaggtcaca actcattttc aaagaaagag gagagtgaga       600
gacaatgtaa ctaaaaaaat ggtgacccaa agaacaatag gaaaaaagaa acataaatta       660
gacaaaagaa gttacctaat tagggcatta accctgaaca caatgaccaa agatgctgag       720 aggggggaaac taaaacgcag agcaattgca accccaggaa tgcaaataag ggggtttgta       780
tactttgttg agacactggc aagaagcata tgtgaaaagc ttgaacaatc agggttgcca       840 gttgaggaa atgagaagaa agcaaagtta gcaaatgttg taaggaagat gatgaccaac       900
tcccaggaca ctgaaatttc ttttaccatc actggagata acacaaatg gaacgaaaat       960 caaaacccta gaatgttctt ggccatgatc acatatataa ccaaagatca gcctgaatgg      1020
ttcagaaata ttctaagtat tgctccaata atgttttcaa acaaaatggc gagactaggt      1080 aggggggtata tgtttgaaag caagagtatg aaactgagaa cccaaatacc tgcagagatg      1140
```

-continued

```
ctagccaaca tagatttgaa atatttcaat gattcaacta aaaagaaaat tgaaaaaatt      1200
cgaccattat taatagatgg aactgcatca ttgagtcctg aatgatgat gggcatgttc       1260 aatatgttaa gcaccgtctt gggcgtttcc attctgaatc ttgggcaaaa aagatacacc      1320
aagactactc actggtggga tggtcttcaa tcgtctgatg attttgcttt gattgtgaat      1380
gcacccaatt atgcaggaat tcaagctgga gttgacaggt tttatcgaac ctgtaagctg      1440
ctcggaatta atatgagcaa aaagaagtct tacataaaca gaacaggtac ctttgaattc      1500
acgagctttt tctatcgtta tgggtttgtt gccaatttca gcatggagct tcctagtttt      1560
ggggtgtctg gggtcaatga atctgcagac atgagtattg gagtcactgt catcaaaaac      1620
aatatgataa acaatgacct tggcccagca actgctcaaa tggcccttca gttatttata      1680
aaagattaca ggtacactta tcgatgccac agaggtgaca cacaaataca aacccggaga      1740
tcatttgaaa taaagaaact atgggaccaa acccgctcca aagctgggct gttggtctct      1800
gatggaggcc ccaatttata taacattagg aatctacata ttcctgaagt ctgcttgaaa      1860
tgggagttga tggatgagga ttaccagggg cgtttatgca acccattgaa cccgtttgtc      1920
agccataaag agattgaatc agtgaacaat gcagtgataa tgccggcaca tggtccagcc      1980
aaaaatatgg agtatgacgc tgttgcaaca acacactctt gggtccccaa aagaaatcga      2040
tccattttaa acacgagcca aagagggata cttgaagatg agcaaatgta ccaaaggtgc      2100
tgcaatttat ttgaaaaatt cttcccaagt agctcataca gaagaccagt tggaatatcc      2160
agtatggtag aggctatggt ttcaagagcc cgaattgatg cacggattga tttcgaatct      2220
ggaaggataa agaaagagga attcgctgag atcatgaaga cctgttccac cattgaagac      2280
ctcagacggc aaaaataggg aatttggctt gtccttcatg aaaaaatgcc ttgtttctac      2340
t                                                                       2341
```

```
<210> SEQ ID NO 11
<211> LENGTH: 2341
<212> TYPE: DNA
<213> ORGANISM: Influenza 105p30

<400> SEQUENCE: 11
```

```
agcgaaagca ggtcaattat attcaatatg gaaagaataa aagagctaag gaatctgatg        60
tcacaatctc gcactcgcga gatacttacc aaaactactg tagaccacat ggccataata       120
aagaaataca catcaggaag acaggagaaa aacccatcac ttaggatgaa atggatgatg       180
gcaatgaaat acccaattac agctgataaa aggataacgg aaatgattcc tgaaagaaat       240
gagcaaggac agacactatg gagtaaagtg aatgatgccg gatcagaccg agtgatgata       300
tcacccctag ctgtgacatg gtggaacaga aatggaccat ggcaaacac tatccactat        360 ccaaaaatct acaaaactta ctttgaaaag gttgaaaggt aaaacatgg aaccttttggc        420 cctgtacact ttagaaacca agtcaaaata cgccgaagag tcgacataaa tcctggtcat       480
gcagacctca gcgccaagga ggcacaggat gtaattatgg aagttgtttt ccctaatgaa       540
gtgggagcca gaatactaac atcagaatcg caattaacga taactaagga gaaaaaagag       600
gaactccaga attgcaaaat ttccccttttg atggttgcat acatgttaga gagggaactt      660
gtccgcaaaa caagatttct cccggttgca ggtggaacaa gcagtgtgta cattgaagtt       720
ttgcatttaa cacaggggac atgctgggag cagatgtaca ctccaggtgg ggaggtgagg       780
aatgatgatg ttgatcaaag cctaattatt gctgctagga acatagtgag aagagctgca       840
```

-continued

```
gtatcagcag atccactagc atctttatta gaaatgtgcc atagcacaca gattggtgga      900
acaaggatgg tggatattct caggcaaaat ccaacagaag aacaagctgt ggacatatgc      960
aaagcagcaa tggggctgag aatcagttca tccttcagtt ttggcggatt cacatttaag     1020
agaacaagtg gatcgtcagt caaaagggag gaagaagtgc taacgggcaa tctgcaaaca     1080
ttgaagctaa ctgtgcatga gggatatgaa gaattcacaa tagttgggaa aaaggcaaca     1140
gctatactca gaaaagcaac caggagattg attcaactaa tagtgagtgg aagagacgaa     1200
cagtcaatag tcgaagcaat agttgtagca atggtattct cacaagaaga ttgcatggta     1260
aaagcggtta gaggtgatct gaatttcgtt aatagagcga atcagcggtt gaatcccatg     1320
catcaacttt tgagacattt tcagaaggat gctaaagtac ttttcctaaa ttggggaatt     1380
gaacatattg acaatgtgat gggaatgatt gggatattac ctgatatgac tccaagtacc     1440
gagatgtcaa tgagaggagt gagagtcagc aaaatgggtg tagatgaata ctccaatgct     1500
gaaagggtag tggtaagcat tgaccgtttt ttgagggtcc gggaccaaag aggaaatgta     1560
ttactgtctc cagaggaagt cagtgaaaca caaggaacag agaaactgac aataacttac     1620
tcttcatcat tgatgtggga gattaatggc cctgagtcag tgttgatcaa tacctaccaa     1680
tggatcatca gaaactggga gactgttaaa attcagtggt ctcagaaccc tacaatgcta     1740
tacaataaaa tggaatttga gccatttcaa tctctagtcc ccaaggccat tagaggccaa     1800
tacagtgggt ttgttagaac tctatttcaa caaatgaggg atgtgctcgg gacctttgac     1860
acaactcaga taataaaact tcttcccttt gcagccgctc caccaaagca aagtagaatg     1920
caattctcgt cattaactgt gaatgtgagg ggatcaggaa tgagaatact tgtaaggggt     1980
aattctccag tattcaacta caacaagacc actaagagac tcacaatcct cggaaaggat     2040
gctggcactt taactgaaga cccagatgaa ggcacagctg gagtggaatc tgctgtttta     2100
aggggattcc tcattctagg caaagaagat agaagatatg gccagcatt aagcatcagt      2160 gaattgagca accttgcgaa aggggagaaa gctaatgtgc taattgggca aggggatgta     2220
gtgttggtaa tgaaacgaaa acgggactct agcatactta ctgacagcca gacagcgacc     2280
aaaagaattc ggatggccat caattaattt cgaataattt aaaaacgacc ttgtttctac     2340
t                                                                      2341
```

```
<210> SEQ ID NO 12
<211> LENGTH: 1565
<212> TYPE: DNA
<213> ORGANISM: Influenza 105p30

<400> SEQUENCE: 12
```

```
agcaaaagca gggtagataa tcactcactg agtgacatca aagtcatggc gtcccaaggc       60
accaaacggt cttacgaaca gatggagact gatgggggaac gccagaatgc aactgaaatc      120
agagcatccg tcggaagaat gattggggga attgggcgat ctacatcca aatgtgcacc        180 gagcttaagc tcaatgatta tgaggacga ctgatccaga acagcttaac aatagagaga        240
atggtgcttt ctgcttttga tgagaggaga aataaatatc tggaagaaca tcccagcgca       300
gggaaagatc ctaagaaaac tggaggaccc atatacaaga gagtagatgg aaagtgggtg       360
agggaactcg tcctttatga caaagaagaa ataaggcgga tttggcgcca agccaacaat       420
ggtgatgatg caacagctgg tttgactcac attatgatct ggcattctaa tttgaatgat       480
acaacttacc agaggacaag agctcttgtc cgcaccggaa tggatcccag gatgtgctct       540
ttgatgcaag gttcaactct ccctagaaga tctggagcag caggcgctgc agtcaaagga       600
```

-continued

```
gttgggacaa tggtattgga gttaatcagg atgatcaaac gtgggatcaa cgaccgaaac      660
ttctggaggg gtgagaatgg gagaaaaaca aggattgctt atgagagaat gtgcaacatt      720
ctcaaaggaa aatttcaaac agctgcacaa aaagcaatga tggatcaagt gagagaaagc      780
cggaacccag gaaatgctga gatcgaagat ctcactttt tggcacggtc tgcactcata      840
ttgagaggat cagttgctca caagtcttgc ctgcctgctt gtgtgtatgg accagccgta      900
gccagtgggt atgacttcga aaaagaggga tactctttgg tgggagtaga cccttcaaa      960 ctgcttcaaa ccagtcaggt atacagccta attagaccaa acgagaatcc cgcacacaag     1020
agccagttgg tgtggatggc atgcaattct gctgcatttg aagatctaag agtgtcaagc     1080
ttcatcagag ggacaagagt acttccaagg gggaagctct ccactagagg agtacaaatt     1140
gcttcaaatg aaaacatgga tgctattgtc tcaagtactc ttgaactgag aagcagatac     1200
tgggccataa gaaccagaag tggagggaac accaatcaac aaagggcctc tgcgggccaa     1260
atcagcacac aacctacgtt ttctgtgcag agaaacctcc catttgacaa aacaaccatc     1320
atggcagcat tcactgggaa tacagaggga agaacatcag acatgcgggc agaaatcata     1380
aagatgatgg aaagtgcaag accagaagaa gtgtccttcc agggacgggg agtctttgag     1440
ctctcggacg aaaggggcaac gaacccgatc gtgccctcct ttgacatgag taatgaagga     1500
tcttatttct tcggagacaa tgcagaggag tacgacaatt aatgaaaaat acccttgttt     1560
ctact                                                                  1565

<210> SEQ ID NO 13
<211> LENGTH: 1027
<212> TYPE: DNA
<213> ORGANISM: Influenza 105p30

<400> SEQUENCE: 13
agcaaaagca ggtagatatt gaaagatgag tcttctaacc gaggtcgaaa cgtacgttct       60
ctctatcgtc ccatcaggcc ccctcaaagc cgagatcgca cagagacttg aagatgtatt      120
tgctggaaag aataccgatc ttgaggctct catggaatgg ctaaagacaa gaccaatcct      180
gtcacctctg actaaggggg ttttaggatt tgtgttcacg ctcaccgtgc ccagtgagcg      240
aggactgcag cgtagacgct ttgtccaaaa tgcccttaat gggaatgggg atccaaataa      300 tatgacaag gctgtcaaac tgtatcgaaa gcttaagagg gagataacat tccatgtgggc      360 caaagaaata gcactcagtt attctgctgg agcacttgcc agttgtatgg gactcatata      420
caacaggatg ggggctgtga ccaccgaatc agcatttggc cttatatgtg caacctgtga      480
acagattgcc gactcccagc ataagtctca taggcaaatg gtaacaacaa ccaatccatt      540
aataagacat gagaacagaa tggttctggc cagcactaca gctaaggcta tggagcaaat      600
ggctggatcg agtgaacaag cagctgaggc catggaggtt gctagtcagg ccaggcagat      660
ggtgcaggca atgagagcca ttgggactca tcctagctct agcactggtc tgaaaaatga      720
tctccttgaa aatttgcagg cctatcagaa acgaatgggg gtgcagatgc aacgattcaa      780
gtgatcctct tgttgttgcc gcaagtataa ttgggattgt gcacctgata ttgtggatta      840
ttgatcgcct ttttttccaaa agcatttatc gtattttaa acacggttta aaaagagggc      900
cttctacgga aggagtaccg gagtctatga gggaagaata tcgagaggaa cagcagaatg      960
ctgtggatgc tgacgatggt cattttgtca gcatagagct agagtaaaaa actaccttgt     1020
ttctact                                                                1027
```

-continued

```
<210> SEQ ID NO 14
<211> LENGTH: 889
<212> TYPE: DNA
<213> ORGANISM: Influenza 105p30

<400> SEQUENCE: 14
agcaaaagca gggtggcaaa gacataatgg attcccacac tgtgtcaagc tttcaggtag      60
attgtttcct ttggcatgtc cgcaaacaag ttgcagacca agatctaggc gatgcccct      120 tccttgatcg gcttcgccga gatcagaagt ctctaaaggg acgaggcaac actctcggtc     180
tgaacatcga aacagccact tgtgttggaa agcaaatagt agagaggatt ctgaaagaag     240
aatccgatga gacatttaga atgaccatgg cctccgcact tgcttcgcgg tacctaactg     300
acatgactgt tgaagaaatg tcaagggact ggttcatgct catgcccaag cagaaagtgg     360
ctggccctct ttgtgtcaga atggaccagg cgataatgga taagaacatc atactgaaag     420
cgaacttcag tgtgattttt gaccggttgg agaatctgac attactaagg gctttcaccg     480
aagagggagc aattgttggc gaaatttcac cattgccttc ttttccagga catactaatg     540
aggatgtcaa aaatgcaatt ggggtcctca tcgggggact tgaatggaat gataacacag     600
ttcgagtctc tgaagctcta cagagattcg cttggagaag cagtaatgag actgggggac     660
ctccattcac tacaacacag aaacggaaaa tggcgggaac aattaggtca gaagtttgaa     720
gaaataagat ggctgattga agaagtgagg cataaattga gacgacagag gagtagtttt     780
gaacaaataa catttatgca agcattacag ctattgtttg aagtggaaca agagattaga     840
acgttctcgt ttcagcttat ttaatgataa aaacacccct gtttctact              889

<210> SEQ ID NO 15
<211> LENGTH: 1775
<212> TYPE: DNA
<213> ORGANISM: Influenza 105p30

<400> SEQUENCE: 15
agcgaaagca ggggaaaata aaagcaacca aaatgaaagt aaaactactg gttctgttat       60
gtacatttac agctacatat gcagacacaa tatgtatagg ctaccatgcc aacaactcaa      120
ccgacactgt tgacacagta cttgagaaga atgtaacagt gacacactct gtcaacctac      180
ttgaggacag tcacaatgga aaactatgtc tactaaaagg aatagcccca ctacaattgg      240
gtaattgcag cgttgccgga tggatcttag aaacccagaa tgcgaatta ctgatttcca       300 aggaatcatg gtcctacatt gtagaaacac caaatcctga aatggaaca tgttacccag        360 ggtatttcgc cgactatgag gaactgaggg agcaattgag ttcagtatct tcatttgaaa      420
ggttcgaaat attccccaaa gagagctcat ggcccaacca caccgtaacc ggagtatcag       480
catcatgctc ccataacggg aaaagcagtt tttacagaaa tttgctatgg ctgacgggga      540
agaatggttt gtacccaaac ctgagcaagt cctatgcaaa caacaaagag aaagaagtcc      600
ttgtactatg gggtgttcat cacccgccta acatagggga ccaaagggcc ctctatcata     660
cagaaaatgc ttatgtctct gtagtgtctt cacattatag cagaagattc accccagaaa      720
tagccaaaag acccaaggtg agagaccagg aaggaagaat caactactac tggactctgc      780
tggaacccgg ggatacaata atatttgagg caaatggaaa tctaatagcg ccaaggtatg      840
ctttcgcact gagtagaggc ttgggatcag gaatcatcac ctcaaatgca ccaatggatg      900
aatgtgatgc aaagtgtcaa acacctcagg agctataaa cagcagtctt cctttccaga       960
atgtacaccc agtcacaata ggagagtgtc caaagtatgt caggagtgca aaattaagga     1020
```

-continued

```
tggttacagg actaaggaac atcccatcca ttcaatccag aggtttgttt ggagcaattg    1080
ccggtttcat tgaaggggggg tggactggaa tggtagatgg ttggtatggt tatcatcatc    1140
agaatgagca aggatctggg tatgctgcag atcaaaaaag cacacaaaat gccattaacg    1200
ggattacaaa caaggtgaat tctgtaattg agaaaatgaa cactcaattc acagctgtgg    1260
gcaaagaatt caacaaattg gaaagaagga tggaaaactt aaataaaaaa gttgatgatg    1320
ggtttctaga catttggacc tataatgcag aattgttggt tctactggaa aatgaaagga    1380
ctttggattt ccatgactcc aacgtgaaga atctgtatga gaaagtaaaa agccaattaa    1440
agaataatgc caaagaaata ggaaacgggt gttttgaatt ctatcacaag tgtaacgatg    1500
aatgcatgga gagtgtgaaa atggaactt atgactatcc aaaatattcc gaagaatcaa    1560
agttaaacag agagaaaatt gatggagtga aattggaatc aatgggagtc tatcagattc    1620
tggcgatcta ctcaacagtc gccagttccc tggttctttt ggtctccctg ggggcaatca    1680
gcttctggat gtgttccaat gggtctttgc agtgtagaat atgcatctaa gaccagaatt    1740
tcagaaatat aaggaaaaac acccttgttt ctact                               1775
```

```
<210> SEQ ID NO 16
<211> LENGTH: 1462
<212> TYPE: DNA
<213> ORGANISM: Influenza 105p30

<400> SEQUENCE: 16
agcaaaagca ggagtttaaa atgaatccaa atcaaaaaat aataaccatt ggatcaatca      60
gtatagcaat cggaataatt agtctaatgt tgcaaatagg aaatattatt tcaatatggg     120
ctagtcactc aatccaaact ggaagtcaaa accacactgg aatatgcaac caaaaaatca     180
tcacatatga aaacagcacc tgggtgaatc acacatatgt taatattaac aacactaatg     240
ttgttgctgg aaaggacaaa acttcagtga cactggccgg caattcatct ctttgtccta     300
tcagtggatg ggctatatac acaaaagaca acagcataag aattggctcc aaaggagatg     360
tttttgtcat aagagaacct ttcatatcat gttctcactt ggaatgcaga acctttttc      420 tgacccaagg tgctctatta aatgacaaac attcaaatgg aaccgttaag gacagaagtc     480
cttatagggc cttaatgagc tgtcctctag gtgaagcccc gtcaccatac aattcaaagt     540
ttgaatcagt tgcatggtca gcaagcgcat gccatgatgg caagggctgg ttaacaatcg     600
gaatttctgg tccagacaat ggagctgtgg ctgtactaaa atacaacgga ataataactg     660
aaaccataaa aagttgggaa aagcgaatat tgagaacaca agagtctgaa tgtgtttgtg     720
tgaacgggtc atgtttcacc ataatgaccg atggcccgag taatgggccc gcctcgtaca     780
aaatcttcaa gatcgaaaag gggaaggtta ctaaatcaac agagttgaat gcacccaatt     840
ttcattatga ggaatgttcc tgttacccag acactggcac agtgatgtgt gtatgcaggg     900
acaactggca tggttcaaat cgaccttggg tatcttttaa tcaaaacttg gattatcaaa     960
taggatacat ctgcagtgga gtgttcggtg acaatccgcg tcccaaagat gggaagggca    1020
gctgtaatcc agtgactgtt gatggagcag acggagttaa ggggtttttca tacaaatatg    1080 gtaatggtgt ttggatagga aggactaaaa gtaacagact tagaaagggg tttgagatga    1140
tttgggatcc taatggatgg acagataccg acagtgattt ctcagtgaaa caggatgttg    1200
tggcaataac tgattggtca gggtacagcg gaagtttcgt ccaacatcct gagttaacag    1260
gattggactg tataagacct tgcttctggg ttgagttagt cagaggactg cctagagaaa    1320
```

-continued

```
atacaacaat ctggactagt gggagcagca tttctttttg tggcgttgat agtgatactg    1380
caaattggtc ttggccagac ggtgctgagt tgccgttcac cattgacaag tagctcgttg    1440
aaaaaaactc cttgtttcta ct                                            1462
```